US008815872B2

(12) United States Patent
Yu et al.

(10) Patent No.: US 8,815,872 B2
(45) Date of Patent: Aug. 26, 2014

(54) MACROCYCLICS PYRIMIDINES AS AURORA KINASE INHIBITORS

(75) Inventors: Henry Yu, Wellesley, MA (US); Lizbeth Celeste De Selm, Melrose, MA (US); Xuliang Jiang, Braintree, MA (US); Benny C. Askew, Jr., Marshfield, MA (US); Srinivasa R. Karra, Pembroke, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/062,413

(22) PCT Filed: Sep. 3, 2009

(86) PCT No.: PCT/US2009/055841
§ 371 (c)(1),
(2), (4) Date: Mar. 30, 2011

(87) PCT Pub. No.: WO2010/028116
PCT Pub. Date: Mar. 11, 2010

(65) Prior Publication Data
US 2011/0294801 A1  Dec. 1, 2011

Related U.S. Application Data

(60) Provisional application No. 61/191,505, filed on Sep. 8, 2008.

(51) Int. Cl.
*A61K 31/529* (2006.01)
*C07D 239/42* (2006.01)
*C07D 487/08* (2006.01)
*C07D 487/18* (2006.01)
*C07D 498/08* (2006.01)
*C07D 498/18* (2006.01)
*C07D 513/08* (2006.01)
*C07D 513/18* (2006.01)
*C07D 515/08* (2006.01)

(52) U.S. Cl.
CPC ............ *C07D 498/08* (2013.01); *C07D 513/08* (2013.01); *C07D 498/18* (2013.01); *C07D 515/08* (2013.01); *C07D 487/08* (2013.01); *C07D 513/18* (2013.01); *C07D 487/18* (2013.01)
USPC ........... 514/257; 540/456; 540/461; 540/469; 540/471

(58) Field of Classification Search
USPC ................... 540/456, 461, 469, 472; 514/257
See application file for complete search history.

(56) References Cited

U.S. PATENT DOCUMENTS

2005/0215556 A1   9/2005 Lin

FOREIGN PATENT DOCUMENTS

| EP | 1803723 A1 | 7/2007 |
|---|---|---|
| WO | 03/076424 A1 | 9/2003 |
| WO | 2004/026881 A1 | 4/2004 |
| WO | 2004/078682 A3 | 9/2004 |
| WO | 2005/047294 A1 | 5/2005 |
| WO | 2006/061415 A1 | 6/2006 |
| WO | 2007/079982 A3 | 7/2007 |
| WO | 2009/132202 A3 | 10/2009 |

OTHER PUBLICATIONS

Sausville, Nat. Med., vol. 10; pp. 234-235 (2004).
Warner, Molecular Cancer Theraputics, vol. 2; pp. 589-595 (2003).
Mountzios, Cancer Treatment Reviews, vol. 34; pp. 175-182 (2008).
Gautschi, Clin. Cancer Res., vol. 14, Issue 6; pp. 1639-1648 (2008).
Mortlock, Current Topics in Medicinal Chemistry, vol. 5; pp. 807-821 (2005).
Qin, J. Biol. Chem. vol. 279(25); pp. 26748-26753 (2004).
Berge, J. Pharma. Science, vol. 66; pp. 1-19 (1977).
The Science and Practice of Pharmacy 21st Ed., pp. 1660-1675 (1995).
Khwaja, EMBO, vol. 16; pp. 2783-2793 (1997).
White, Oncogene, vol. 20; pp. 7064-7072 (2001).
Stephens, Biochemical J., vol. 351; pp. 95-105 (2000).
Alessi, FEBS Lett. vol. 399, Issue 3; pp. 333-338 (1996).
Campos-Gonzalez, J. Biol. Chem., vol. 267; pp. 14535-14538 (1992).
Sorg, J. of. Biomolecular Screening, vol. 7; pp. 11-19 (2002).
Sato, Nature, vol. 376(6535); pp. 70-74 (2004).
Nicalou, Chem. Int. Ed., vol. 44; pp. 4490-4527 (2005).
Lucking, Chem. Med. Chem., vol. 2; pp. 63-77 (2007).
Waser, J. Am. Chem. Soc., vol. 128, 11693-11712 (2006).

*Primary Examiner* — Bruck Kifle
(74) *Attorney, Agent, or Firm* — EMD Serono Research Institute; Thomas W. Brown

(57) ABSTRACT

Macrocyclic derivative compounds that inhibit protein kinase enzymes are disclosed along with pharmaceutical compositions comprising these compounds and methods for synthesizing the same. Such compounds have utility in the treatment of proliferative diseases resulting from unregulated and/or disturbed kinase activity such as cancers, psoriasis, viral and bacterial infections, inflammatory and autoimmune diseases.

5 Claims, 7 Drawing Sheets

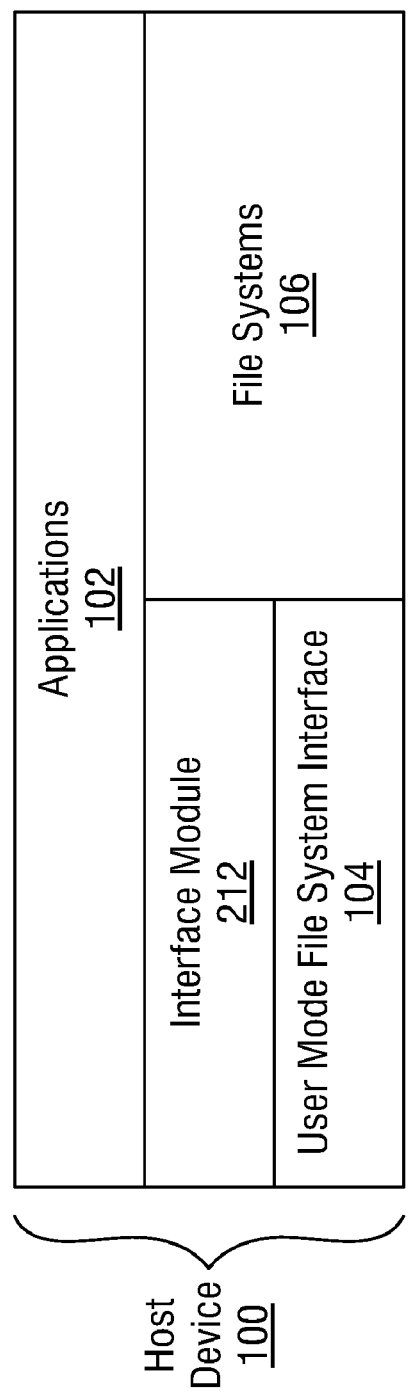

MACROCYCLICS PYRIMIDINES AS AURORA KINASE INHIBITORS

FIELD OF THE INVENTION

Figure 1B:
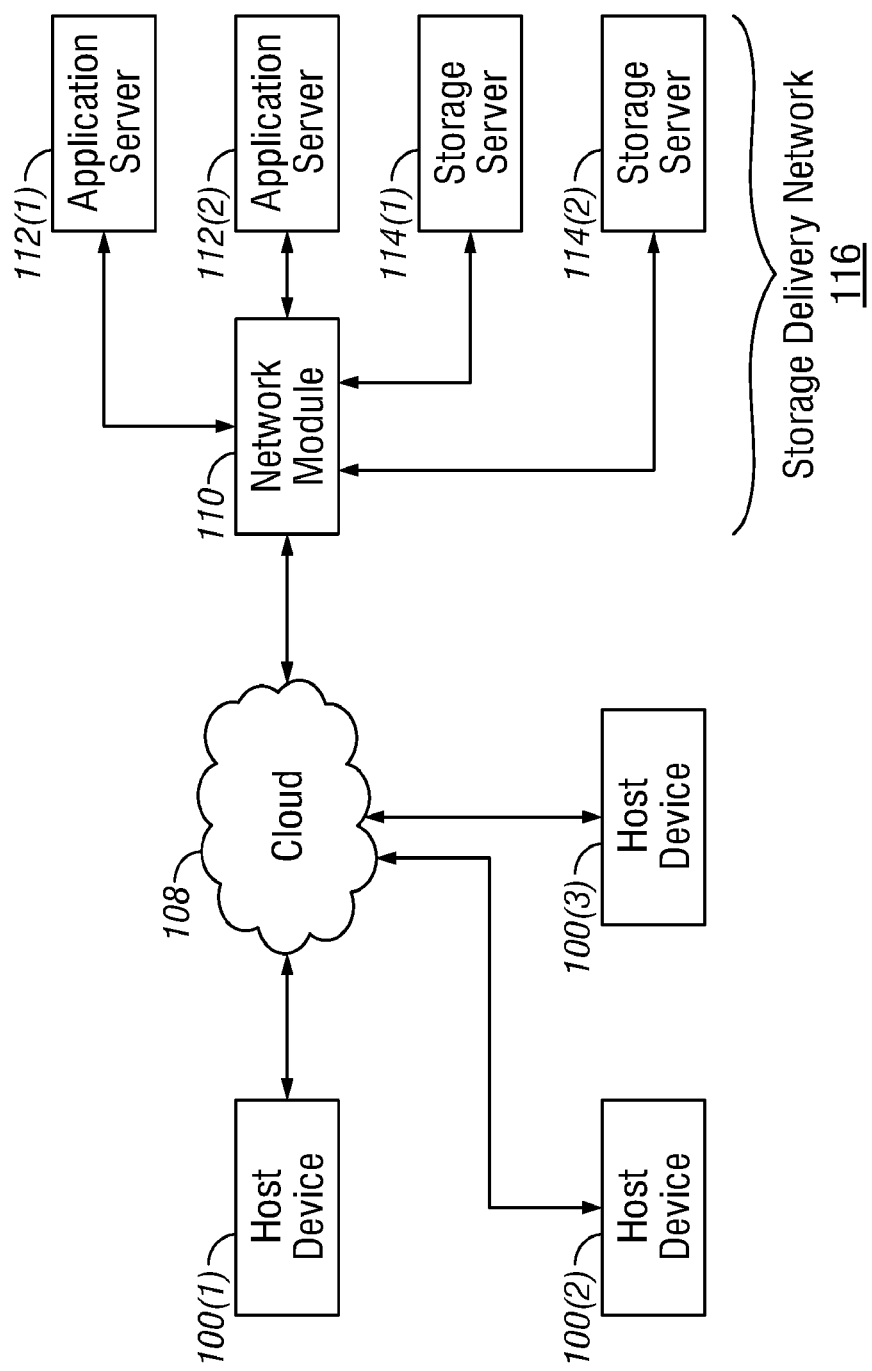
Figure 2A:
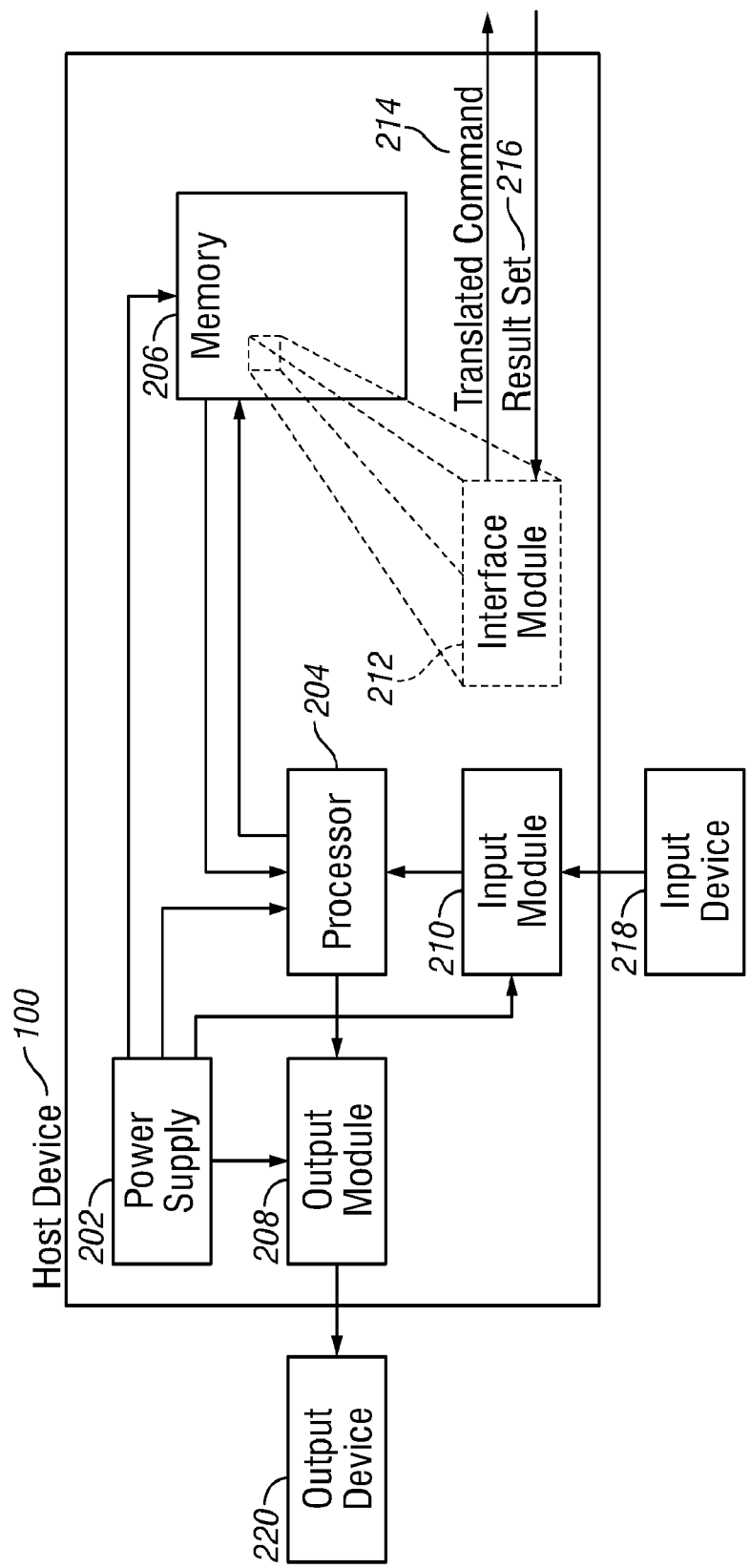
Figure 2B:
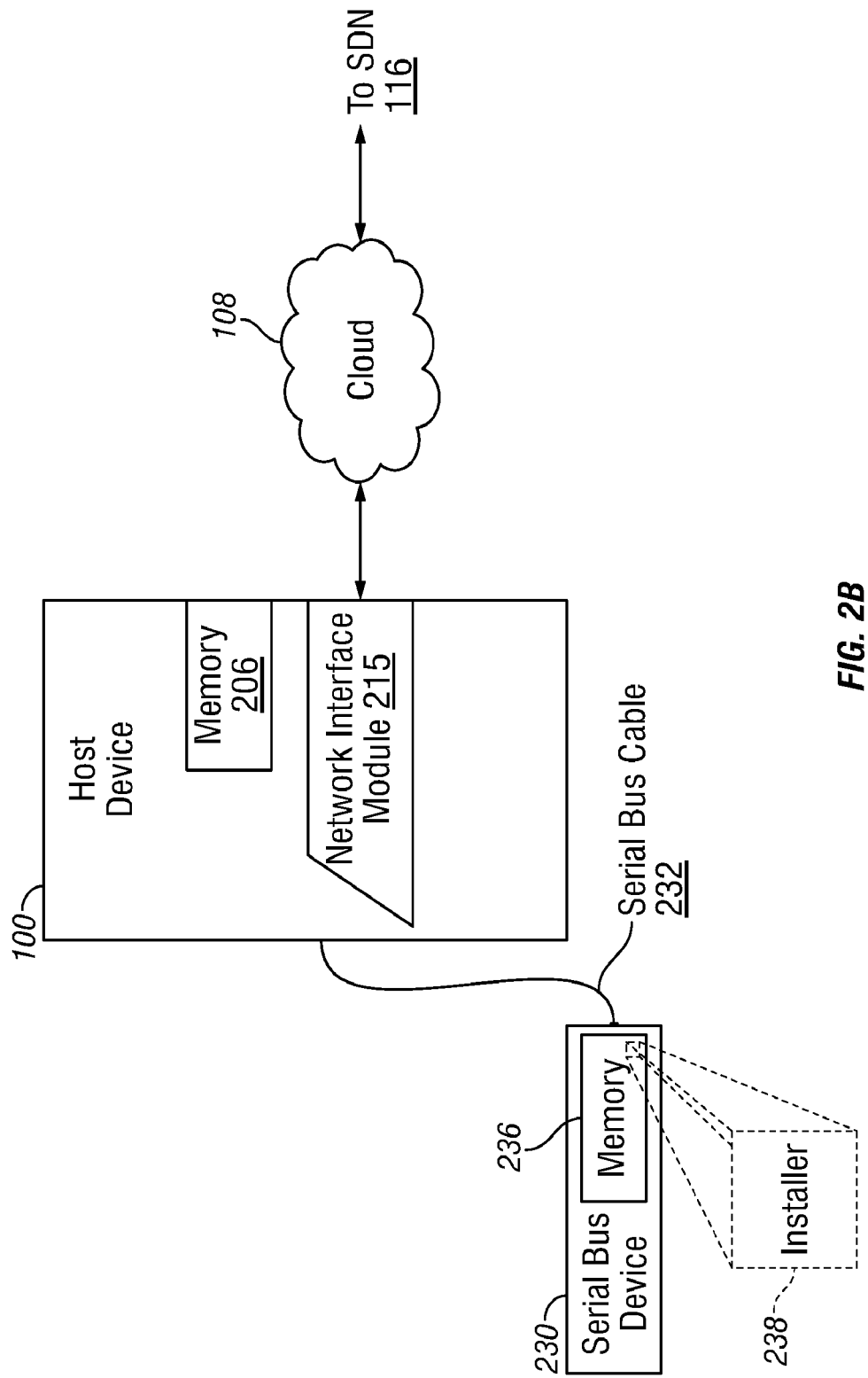
Figure 3:
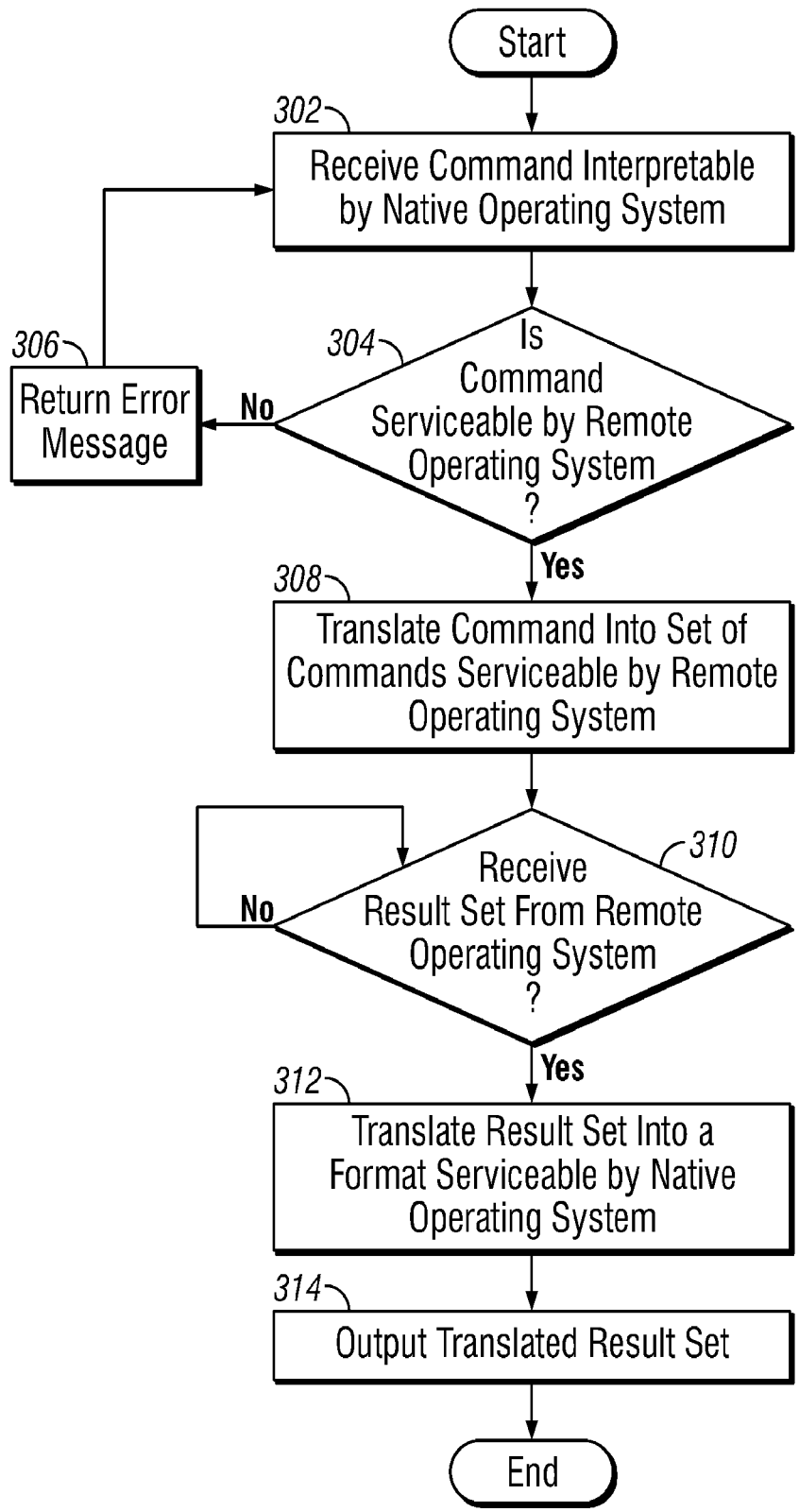
Figure 4:
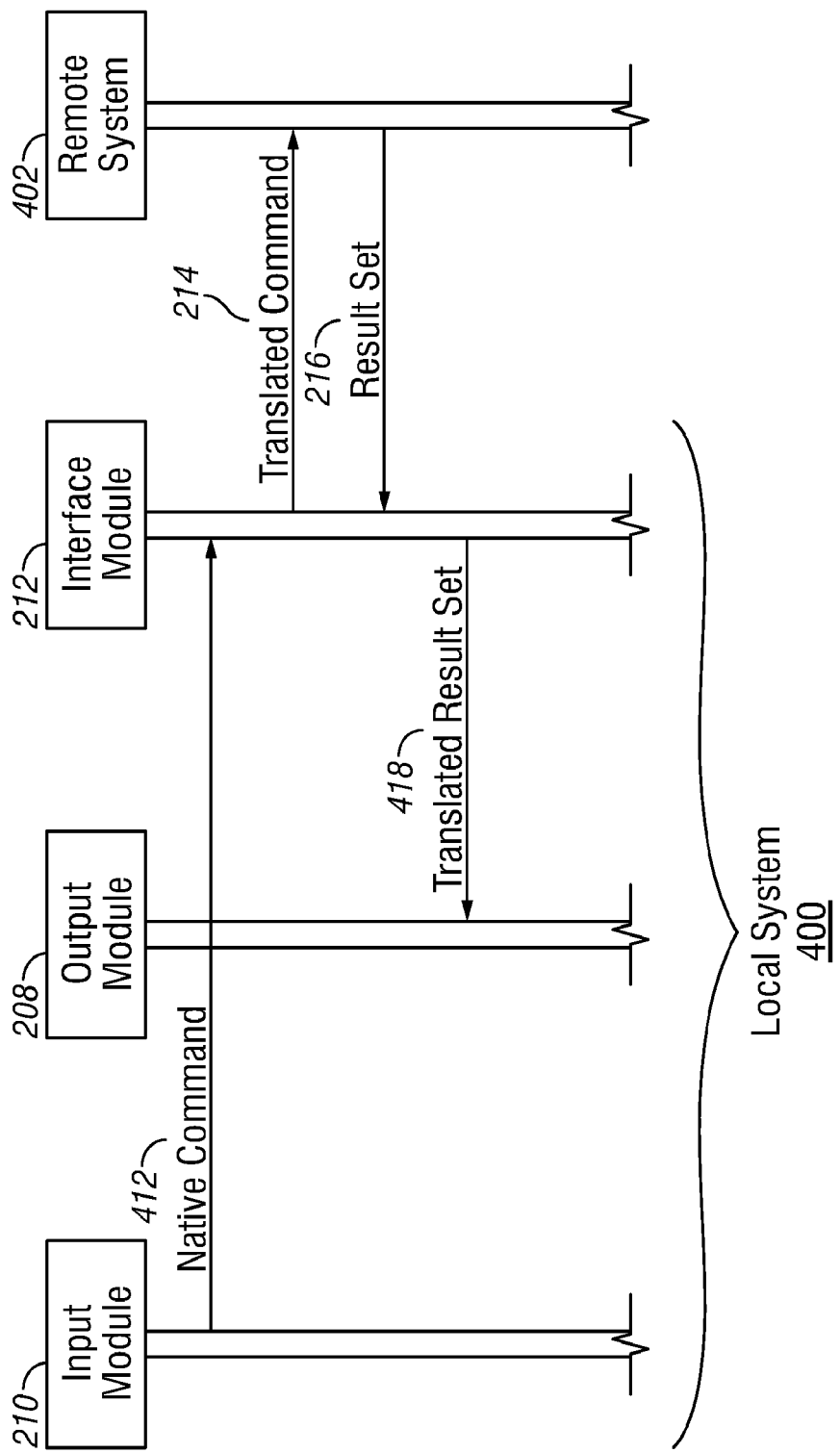
Figure 5:
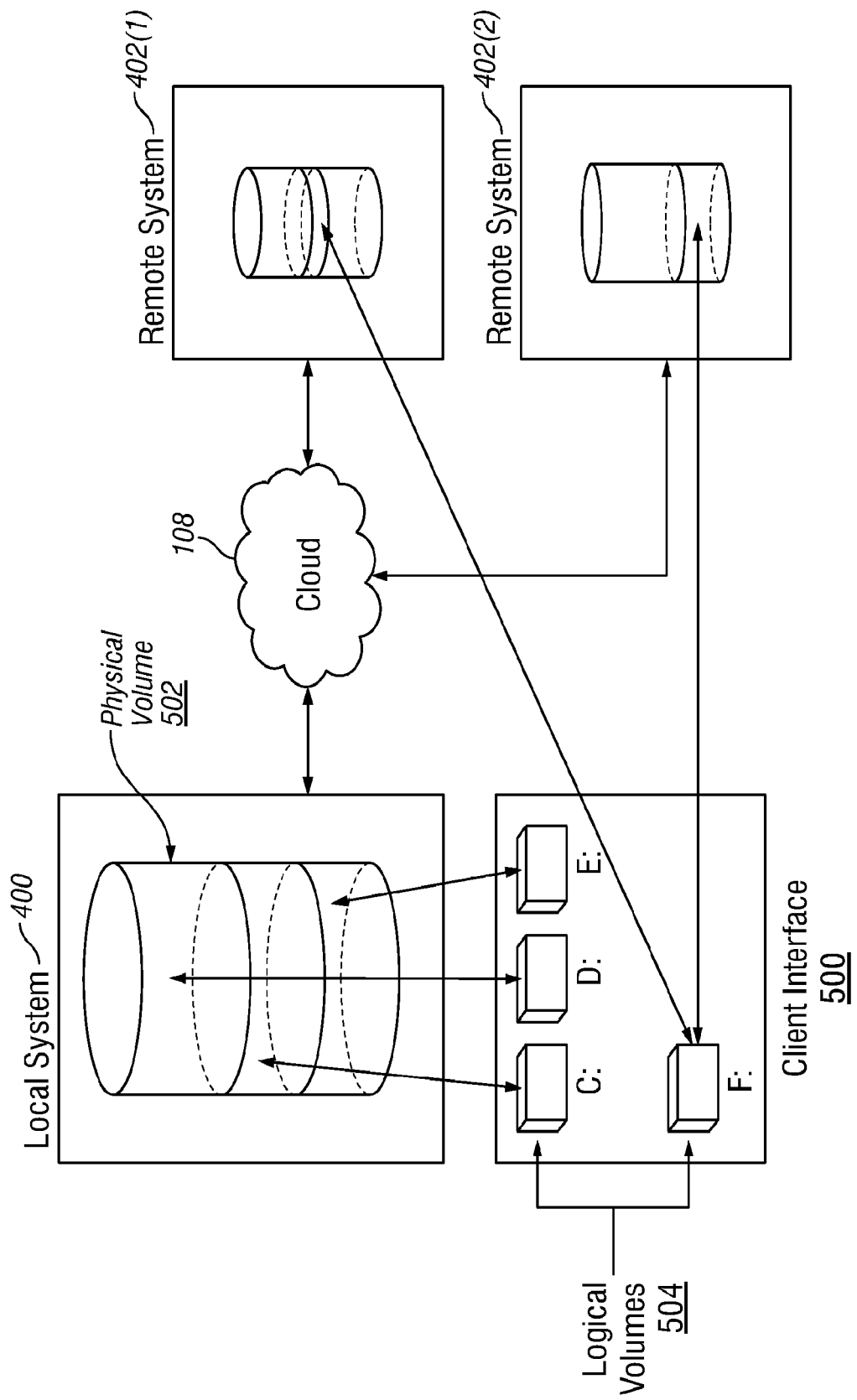

The present invention relates to macrocyclic pyrimidine compounds and their use as pharmacologically active agents capable of inhibiting protein kinases and aurora kinases in particular, thereby inhibiting abnormal cellular proliferation and growth.

BACKGROUND OF THE INVENTION

Protein kinases represent a large family of proteins, which play a central role in the regulation of a wide variety of cellular processes, and so maintain control over cellular function. These kinases includes Akt, Axl, Aurora A, Aurora B, Aurora C, dyrk2, epha2, fgfr3, flt-3, vegfr3, igf1r, IKK2, JNK3, Vegfr2, MEK1, MET, P70s6K, Plk1, RSK1, Src, TrkA, Zap70, cKit, bRaf, EGFR, Jak2, PI3K, NPM-Alk, c-Abl, BTK, FAK, PDGFR, TAK1, LimK, Flt3, Flt1, PDK1 and Erk, among others. Inhibition of such kinases has become an important therapeutic targeting tool.

Many diseases are associated with abnormal cellular responses triggered by protein kinase-mediated events. These diseases include cancers, autoimmune, inflammatory, cardiovascular, neurological and neurodegenerative diseases, allergies and asthma, Alzheimer's disease and hormone-related diseases. Accordingly, there has been a substantial effort in medicinal chemistry to find protein kinase inhibitors that are effective as therapeutic agents.

The compounds of the present invention are novel, selective, and highly potent ATP-competitive inhibitors of Aurora kinases (A, B and C), and protein kinases TrkA, TrkB, Flt3 (D835Y)(h), Ret(h), IRAK4(h), FAK(h), KDR9H0, PYK(2)(h) and Tie2(K849w). The Aurora family of conserved serine/threonine kinases perform essential functions during cell division. The three mammalian paralogues are very similar in sequence, but differ significantly in their localization, function, substrates and regulatory partners.

Aurora A is mainly associated with the spindle poles during mitosis, where it is required for centrosome separation and maturation (Sausville E A. *Nat. Med.*, (2004) 10:234-235). Aurora A also functions in meiosis by promoting oocyte maturation, polar-body extrusion, spindle positioning and exit from metaphase I. Aurora B is a chromosomal-passenger protein with multiple functions in mitosis. It is required for phosphorylating histone H3, targeting condensing, and compacting normal chromosomes. It has also been recently shown to be essential for chromosome biorientation, kinetochore-microtubule interactions and the spindle-assembly checkpoint. Aurora B is essential for completion of cytokinesis. Much less is known about Aurora C kinase, other than that it seems to be preferentially expressed in meiotic cells. Aurora kinases appear to provide an additional level of regulation that might be essential for the choreography of mitotic events.

Aurora kinases are overexpressed in certain types of cancers, including colon, breast, pancreatic, ovarian and other solid-tumor cancers. The genes encoding the Aurora A and B kinases tend to be amplified in certain types of cancers, while the gene encoding the Aurora C kinase resides in a region of the chromosome that is subject to rearrangement and deletion. Aurora A has been associated with a variety of malignancies, including primary colon, colorectal, breast, stomach, ovarian, prostate, and cervical cancer, neuroblastoma, and other solid-tumor cancers (Warner et al. (2003) *Molecular Cancer Therapeutics* 2:589-95). Since Aurora A and B kinases are frequently elevated or overexpressed in human cancers makes them attractive targets for therapeutic intervention (Mountzios et al., *Cancer Treatment Reviews* (2008) 34:175-82; Gautschi et al., *Clin. Cancer Res.* (2008), 14(6): 1639-48; Mortlock et al., *Current Topics in Medicinal Chemistry* (2005), 5:807-21).

TrkA, or Tropomycin-related kinase A, TrkB and TrkC are all members of a sub-family of protein kinases important for neuronal growth and differentiation. TrkA is a high affinity receptor kinase for Nerve Growth Factor (NGF), and so plays a vital role in neuronal differentiation and survival. It is believed to be important in cancers, mental retardation, and insensitivity to pain. TrkB is activated by "Brain Derived Neurotrophic Factor" of "BDNF", and likewise is important in cancers and conditions involving neuronal survival.

Flt3 is a receptor tyrosine kinase that is expressed on hematopoietic progenitors, B-cell precursor cells, and macrophage precursor cells. Thus, Flt3 has important functions in hematopoietic progenitor proliferation and survival, macrophage cellular differentiation, and dendritic cell differentiation. It is overexpressed in acute myeloid leukaemia (AML), and has been shown to be mutated in other hematopoietic diseases.

Ret(h) is a receptor tyrosine kinase for glial cell line-derived neurotrophic factors of extracellular signalling molecules. Loss of function mutations associated with this family of kinases are related to development of Hirschsprung's disease, while overexpression of Ret(h) is associated with cancers, including medullar thyroid carcinoma, parathyroid tumors, endocrine neoplasias types II and III, and phaeochromocytoma.

IRAK4(h), interleukin-1-receptor-associated kinase-4, is one member of the IRAK family needed for activation of the Interleukin-1 (IL-1) pathway. Qin et al. have shown that kinase activity of IRAK and IRAK4 are redundant for IL-1 mediated signalling, but IRAK4 is required for the efficient recruitment of IRAK to the IL-1 receptor complex (Qin et al., *J. Biol. Chem.*, 279(25):26748-53 (Jun. 18, 2004). Malfunctioning of the IL-1 pathway can result in problems with fever and inflammation, immune system deficiencies and infections via non-functioning lymphocytes, rheumatoid arthritis, degenerative bone disease, and Alzheimer's disease.

The Focal Adhesion Kinase, FAK, acts in cellular adhesion, motility and survival. It is a non-receptor tyrosine kinase that was identified originally as a substrate for the oncogene protein tyrosine kinase, v-src, but is now believed also to play a role in anchoring cytoskeletons, and hence its association with cancers. PYK-2 also is a member of the FAK family, and is named for being a proline-rich tyrosine kinase. Also called "related adhesion focal tyrosine kinase", "cell adhesion kinase" and "calcium-dependent tyrosine kinase", PYK-2 is found in fewer types of cells compared to FAK, but its expression is high in neural, epithelial and hematopoietic cells, in natural killer cells, B and T lymphocytes, and megakaryocytes. Thus, it plays an important role in immune and inflammatory responses and in cellular polarization via cytoskeletal reorganization in lymphocytes; 15 Aug. 8).

KDR or or "kinase insert domain receptor" is a type III receptor tyrosine kinase, and is ubiquitous throughout the body. Hence, its overexpression is associated with cancers of various types, rheumatoid arthritis, bone and mental diseases among others.

Tie-2 along with the co-member of its family, Tie-1, is a receptor protein kinase that is expressed in developing vascular endothelial cells. Tie-2 is especially important in angiogenesis for development of vascular networks among endothelial cells, while Tie-1 is more important in establishing vascular structural integrity, the loss of which results in hemorrhage and edema (Sato et al., *Nature*, 1995, 376(6535):70-74).

A limited number of macrocyclic compound inhibitors of protein kinases have been reported. For example, Schering AG teaches macrocyclic anilino-pyrimidine compounds that have a substituted sulfoximine moiety and that selectively inhibit type 2 cell kinases like Aurora kinases while also acting as selective inhibitors of type 1 cell kinases such as cyclin-dependent kinases (WO 2007/079982). Eisai Co., Ltd., claims marcrocyclic compounds having an optionally substituted benzoyl moiety that are useful in the treatment of malignancies, angiogenesis, inflammatory and autoimmune disorders (WO 03/076424). Cyclin-dependent protein kinases such as CDK2 and CKD5 are inhibitied by macrocyclic pyridyl-pyrimidineamine derivatives, as taught by IRM LLC (WO 04/078682). Abbott Laboratories teaches cancer-treating protein kinase inhibitors that are benzodioxatriazacycloheptadecine carbonitrile derivatives (US 2005/0215556; WO 05/047294), Bayer Schering Pharma AG describes pyrimidine benzenecyclonaphthanlenylsulfoximide derivatives that are selective inhibitors of Aurora kinases (EP 1 803 723), and Janssen Pharmaceutica N.V. teaches 2,4 (4,6) pyrimidine macrocycles for the treatment of cancers, diabetes, inflammation and arthritis (WO 06/061415).

Thus, the identification of additional and more effective macrocyclic inhibitors of protein kinases and Aurora kinases in particular is a goal of the present invention. Another goal is to provide derivatives that actively inhibit disturbed, uncontrolled or unregulated Aurora kinase activity.

These compounds and pharmaceutical compositions comprising them are presented either individually or in kit form. Also contained herein are methods for using the same for treating proliferative disorders, such as cancers, psoriasis, viral and bacterial infections, vascular restinosis, inflammatory and autoimmune diseases, that result from unregulated and uncontrolled cellular proliferation.

Included in this invention are processes for preparing the macrocyclic derivative compounds that actively inhibit unregulated Aurora kinase activity.

Additional objects, features and advantages of the present invention will become apparent to those skilled in the art from the following description and claims.

SUMMARY OF THE INVENTION

The present invention relates to compounds that inhibit, regulate and/or modulate signal transduction by Aurora kinase. The invention also relates to compositions that comprise these compounds, and to methods for using the compounds in the treatment of Aurora kinase-related diseases and complaints. In a first aspect, the present invention provides a compound having a structure according to Formula I:

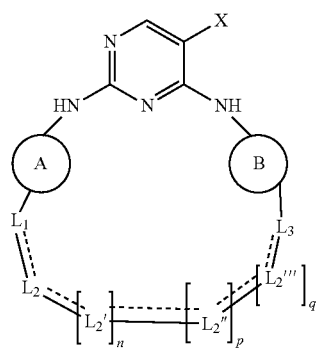

wherein:

X is H; halogen, preferably F; $CF_3$; CN, $NO_2$, N(RR'); C(O)N(RR'); C(O)OR; C(O)H; $S(O)_2$; S(OH); S(O); or S(O)NRR';

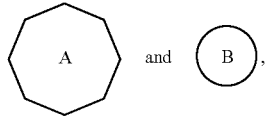

each independently, is aryl, a saturated or unsaturated heterocycle, or a saturated or unsaturated, bridged or non-bridged uni-, bi- or tri-carbocycle, any of which optionally may be substituted;

- - - represents the presence or absence of a double bond;

$L_1$, $L_2$, $L_{2'}$, $L_{2''}$, $L_{2'''}$, and $L_3$, each independently, is $CH_2$, CH, CH(OH), C(=O), O, S, S(O), S(OH), $S(O)_2$, $NR^2$ or NH;

R and R' each independently is H, $C_1$-$C_6$ alkyl; $C_1$-$C_6$ heteroalkyl; aryl; heteroaryl; heterocycle; $(CH_2)_2OH$; $(CH_2)_2$—O—$(CH_2)_2$;

$R^2$ is aryl, heteroaryl or alkyl;

$(CH_2)_2$—$NH_2$; $(CH_2)_2$—$NR_x$ or $(CH_2)_2$—$R_y$, where $R_x$ and $R_y$, each independently, is $CH_3$ or $C_2H_5$;

n, p and q, each independently, is 0 or 1;

r is 0, 1, 2, 3, or 4; or a pharmaceutically acceptable salt, prodrug, hydrate, solvate, tautomer, enantiomer or racemic mix thereof.

In a preferred embodiment, the compound according to Formula I is incorporated into a pharmaceutical formulation along with one or more pharmaceutically acceptable diluent, excipient, carrier, etc. Those of skill in the art will recognize the overlap in the terms "diluent", "excipient" and "carrier".

In a preferred aspect of the present invention,

is substituted or unsubstituted phenyl. The phenyl group may also be joined to a carbocycle, heterocycle or aryl in order to form a bicyclic structure. A particularly preferred meaning of

is phenyl, which is unsubstituted or substituted by CN, OH, F or 4-methyl-piperazine.

In another preferred aspect of the present invention,

is optionally substituted norbornanyl, norbornenyl, cyclopropyl, cyclobutyl, cyclopentanyl, or cyclohexanyl. A particularly preferred meaning of

is bicyclo[2.2.1]heptane-2-carboxamide.

In still another preferred aspect of the present invention, X is H+, CN, $NO_2$, OH, $OR_x$, $OR_y$, $CF_3$, N(RR'); C(O)N(RR'); C(O)OR; C(O)H; $S(O)_2$; S(OH); S(O); S(O)NRR', or halo, and F in particular, where R and R' each independently is H, and $R_x$ and $R_y$ are as defined above.

In yet another preferred aspect of the present invention, $L_1$ and $L_3$ each independently is $CH_2$, O, S(O), $SO_2$, NH or S: $L_2$ is $CH_2$; and n, p and q all are 0.

In still another preferred aspect of the present invention, $L_1$ and $L_3$ each independently is $CH_2$, O, NH or S: $L_2$ is $CH_2$, CH(OH), S(O), $SO_2$ or C(=O); $L_{2'}$, $L_{2''}$, and $L_{2'''}$ each independently is $CH_2$ or CH; and n, p and q all are 1.

Also encompassed by the present invention are methods of treating a subject in need of inhibiting a kinase protein comprising administering to the subject an effective amount of a kinase inhibitor according to Formula I.

In a preferred embodiment, the compound according to Formula I, is incorporated into a pharmaceutical formulation along with one or more pharmaceutically acceptable diluent, excipient, or carrier, and which further optionally may be packaged as a kit.

In a further aspect the invention provides a method for treating or preventing a disease or condition that is a member selected from cancers, tumor formation, angiogenesis, arteriosclerosis, ocular diseases, inflammatory diseases, arthritis, and restinosis, among others. The method includes administering to a subject in need thereof a therapeutically effective amount of a compound of Formula I or a pharmaceutically acceptable salt, prodrug, enantiomer, tautomer, hydrate, solvate or racemic mixture thereof.

Also included within the scope of the invention are preparative compounds I-XX, final product compounds I-39, and a pharmaceutically acceptable salt, prodrug, hydrate, solvate, tautomer, enantiomer or racemic mix thereof.

Additional embodiments of the present invention include: a compound according to Formula I for use as a medicament; use of the compound according to Formula I for the preparation of a medicament for the treatment of a subject in need of inhibiting a kinase protein; and use of the compound according to Formula I for the preparation of a medicament for the suppression or reduction of cellular proliferation in single-site or metastatic cancers.

The present invention also encompasses a compound according to Formula I, or pharmaceutically acceptable derivatives, solvates, salts, tautomers and stereoisomers thereof, including mixtures thereof in all ratios, for use in therapy, such as treating a subject in need of inhibiting a kinase protein, wherein the subject has a proliferative or an inflammatory disease.

A method of synthesizing the compounds of the present invention also is encompassed within the present invention.

Moreover, the present invention is related to the combined use of a compound of Formula I together with further medicament active ingredient for the treatment of a subject in need of treatment for a kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases, autoimmune diseases, cirrhosis, diabetes and vascular and immune diseases in mammals.

The compounds of the present invention especially are useful as Aurora kinase inhibitors for the treatment of solid tumors characterized by having Aurora kinases that are strongly expressed or overexpressed. Such solid tumors include, among others, monocytic leukaemia, brain, breast, pancreatic, ovarian, urogenital, lymphatic system, stomach, laryngeal and lung carcinoma, including lung adenocarcinoma and small-cell lung carcinoma.

The present invention provides pharmaceutical compositions and methods of modulating and/or inhibiting unregulated or disturbed Aurora kinase activity in order to treat or cure proliferative diseases including all types of cancers comprising administering to a subject in need thereof an effective amount of a kinase inhibitor according to Formula I. In particular, the compounds of the Formula I are useful in the treatment of certain forms of cancer. The compounds of Formula I furthermore can be used to provide additive or synergistic effects in certain existing cancer chemotherapies, and/or can be used to restore the efficacy of certain existing cancer chemotherapies and radiotherapies.

The compounds of the present invention have an antiproliferative action in vivo in a xenotransplant tumor model by their inhibitory action on cell division. Thus, when they are administered to a patient having a hyperproliferative disease, these compounds inhibit tumor growth, reduce inflammation associated with a lymphoproliferative disease, inhibit transplant rejection, inhibit neurological damage due to tissue repair, etc. The present compounds are suitable for prophylactic or therapeutic purposes. The prevention of proliferation is achieved by administration of the compounds according to the invention prior to the development of overt disease, for example to prevent the growth of tumors, prevent metastatic growth, diminish restenosis associated with cardiovascular surgery, etc. Alternatively, the compounds are used for the treatment of ongoing diseases by stabilizing or improving the clinical symptoms of the patient.

DETAILED DESCRIPTION OF THE INVENTION

The present invention relates to compounds that inhibit, regulate and/or modulate signal transduction by protein kinases, and by Aurora, TrkA, TrkB, Flt3(D835Y)(h), Ret(h), IRAK4(h), FAK(h), KDR9H0, PYK(2)(h) and Tie2(K849w) in particular. The invention also relates to pharmaceutical compositions that comprise these compounds, and to methods for using the compounds in the treatment of kinase-related diseases and complaints. In a first aspect, the present invention provides a compound having a structure according to Formula I:

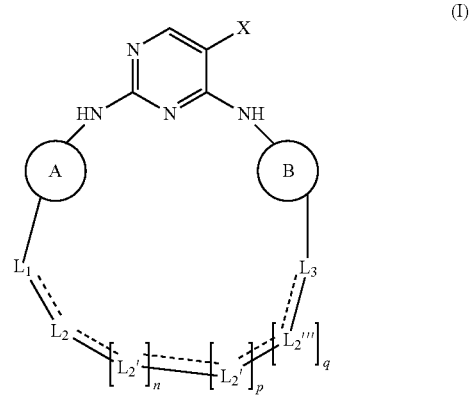

(I)

wherein:

X is H; halogen, preferably F; OH; $OR_x$; $OR_y$; $CF_3$; CN, $NO_2$, N(RR'); C(O)N(RR'); C(O)OR; C(O)H; $S(O)_2$; S(OH); S(O); or S(O)NRR';

$R_x$ and $R_y$, each independently, is $CH_3$ or $C_2H_5$;

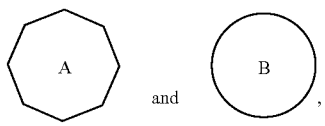

each independently, is aryl, a saturated or unsaturated heterocycle, or a saturated or unsaturated, bridged or non-bridged uni-, bi- or tri-carbocycle, any of which optionally may be substituted;

- - - represents the presence or absence of a double bond;

$L_1$, $L_2$, $L_2'$, $L_2''$, $L_2'''$, and $L_3$, each independently, is $CH_2$, CH, CH(OH), C(=O), O, S, S(O), S(OH), S(O)$_2$, or NH;

R and R' each independently is H, $C_1$-$C_6$ alkyl; $C_1$-$C_6$ heteroalkyl; aryl; heteroaryl; heterocycle; $(CH_2)_2OH$; $(CH_2)_2$—O—$(CH_2)_2$; $(CH_2)_2$—$NH_2$; $(CH_2)_2$—$NR_x$ or $(CH_2)_2$—$R_y$;

n, p and q, each independently, is 0 or 1;

r is 0, 1, 2, 3 or 4; or a pharmaceutically acceptable salt, prodrug, hydrate, solvate, tautomer, enantiomer or racemic mix thereof.

In a preferred embodiment, the compound according to Formula I is incorporated into a pharmaceutical formulation along with one or more pharmaceutically acceptable diluent, excipient, carrier, etc. Those of skill in the art will recognize the overlap in the terms "diluent", "excipient" and "carrier".

In a preferred aspect of the present invention,

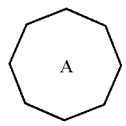

is substituted or unsubstituted phenyl. When substituted, preferred substituents are CN, $CH_3$—C(=O)—NH—, or an optionally substituted, saturated or unsaturated heterocycle. The phenyl group may also be joined to a carbocycle, heterocycle or aryl in order to form a bicyclic or tricyclic structure.

In another preferred aspect of the present invention,

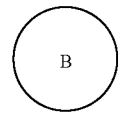

is optionally substituted norbornanyl, norbornenyl, cyclopropyl, cyclobutyl, cyclopentanyl, or cyclohexanyl. Optional substituents include carboxylic acid, carboxylic acid amide, ethane, ethylene, and (2-hydroxy)-ethoxy.

In a first embodiment of the invention,

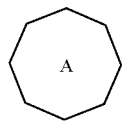

is phenyl;

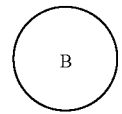

is norbornane substituted by carboxylic acid amide; X is F; $L_1$ is O; $L_2$ is $CH_2$; $L_3$ is S; n is 1; p and q both are 0.

In a first subembodiment of the first embodiment, $L_1$ is NH; $L_2$ is C(=O); $L_2$ is $CH_2$; $L_3$ is S; n is 1; p and q are 0.

In a second subembodiment of the first embodiment, $L_1$ is $CH_2$; $L_2$ is $CH_2$; $L_3$ is S; n, p and q are 0.

In a third subembodiment of the first embodiment, $L_1$ is CH(OH); $L_2$ is $CH_2$; $L_3$ is S; n, p and q are 0.

In a fourth subembodiment of the first embodiment, $L_1$ is $CH_2$; $L_2$ is S; $L_3$ is S; n, p and q are 0.

In a fifth subembodiment of the first embodiment, $L_1$ is $CH_2$; $L_2$ is $CH_2$; $L_3$ is S(O); n, p and q are 0.

In a sixth subembodiment of the first embodiment, $L_1$ is $CH_2$; $L_2$ is $CH_2$; $L_3$ is S(=O)(=O); n, p and q are 0.

In a seventh subembodiment of the first embodiment,

is phenyl;

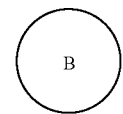

is norbornane substituted by carboxylic acid; X is F; $L_1$ is O; $L_2$ is $CH_2$; $L_2$ is $CH_2$; $L_3$ is S; n is 1; p and q both are 0.

In an eighth subembodiment of the first embodiment, $L_1$ and $L_2$ are both CH; $L_3$ is S; and n, p and q all are 0.

In a second embodiment of the invention,

is phenyl substituted by CN;

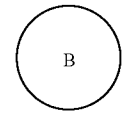

is norbornane substituted by carboxylic acid amide; X is F; $L_1$ is NH; $L_2$ is C(=O); $L_2$ is $CH_2$; $L_3$ is S; n is 1; p and q both are 0.

In a third embodiment of the invention,

is phenyl substituted by methyl-piperazine;

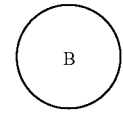

is norbornane substituted by carboxylic acid amide; X is F; $L_1$ is NH; $L_2$ is C(=O); $L_{2'}$ is $CH_2$; $L_3$ is S; n is 1; p and q both are 0.

In a first subembodiment of the third embodiment, $L_1$ is O, $L_2$ is $CH_2$; $L_{2'}$ is $CH_2$; $L_3$ is S; n is 1; p and q both are 0.

In a fourth embodiment of the invention,

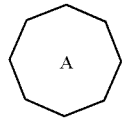

is quinoline;

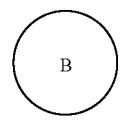

is norbornane substituted by carboxylic acid amide; X is F; $L_1$ is C(=O); $L_2$ is $CH_2$; $L_3$ is S; n, p and q are 0.

In a first subembodiment of the fourth embodiment of the invention,

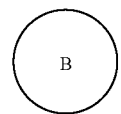

is indole.

In a fifth embodiment of the invention,

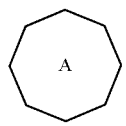

is phenyl;

is cyclopentane disubstituted by a carboxylic acid amide and ethane, ethene, or (2-hydroxy)ethoxy; X is F; $L_1$ is O; $L_2$ is $CH_2$; $L_{2'}$ is $CH_2$; $L_3$ is $CH_2$; n is 1; p and q both are 0.

In a first subembodiment of the fifth embodiment, $L_1$ is O; $L_2$ is $CH_2$; $L_{2'}$ is CH; and $L_3$ is CH; cyclopentane is ortho-disubstituted by carboxylic acid amide and ethanyl; n is 1; p and q are both 0.

In a second subembodiment of the fifth embodiment, $L_1$ is O; $L_2$ is $CH_2$; $L_{2'}$ and $L_3$ both are CH(OH); cyclopentane is ortho-disubstituted by carboxylic acid amide and ethenyl; n is 1; p and q are both 0.

In a third subembodiment of the fifth embodiment, $L_1$ is O; $L_2$ is $CH_2$; $L_{2'}$ and $L_3$ are both CH(OH); cyclopentane is ortho-disubstituted by carboxylic acid amide and (2-hydroxy)ethoxy; n is 1; p and q are both 0.

In a sixth embodiment of the invention,

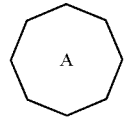

is phenyl;

is cyclohexane; X is F; $L_1$ and $L_3$ are both O; $L_2$ and $L_{2'}$ are both CH; $L_{2'''}$ is $CH_2$; n and p are both 1; and q is 0.

In a first subembodiment of the sixth embodiment of the invention, $L_2$ and $L_{2'''}$ are both $CH_2$; $L_{2'}$ and $L_{2''}$ are both CH(OH); and $L_1$ and $L_3$ are both O.

In a second subembodiment of the sixth embodiment of the invention, $L_1$ and $L_3$ are both O; $L_2$ and $L_{2'''}$ are both $CH_2$; and $L_{2'}$ and $L_{2''}$ are both CH.

In a third subembodiment of the sixth embodiment of the invention, $L_1$ and $L_3$ are both O; $L_2$, $L_{2'}$, $L_{2''}$ and $L_{2'''}$ all are $CH_2$.

In a seventh embodiment of the invention,

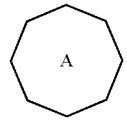

is phenyl substituted by methyl carboxylic acid amide;

is norbornane substituted by carboxylic acid amide; X is F; $L_1$ is CH(OH); $L_2$ is $CH_2$; $L_3$ is S; n, p and q all are 0.

In a first subembodiment of the seventh embodiment of the invention,

is phenyl,

is norbornane substituted by 6-amino1-phenylethenyl-carboxylic acid amide; X is F; $L_1$ is C(=O); $L_2$ is $CH_2$; $L_3$ is S; n, p and q all are 0.

In an eighth embodiment of the invention,

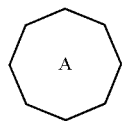

is phenyl;

is norbornane substituted by amino; X is F; $L_1$ is CH(OH); $L_2$ is $CH_2$; $L_3$ is S; n, p and q all are 0.

Also encompassed by the present invention are methods of treating a subject in need of inhibiting a kinase protein comprising administering to the subject an effective amount of a kinase inhibitor according to Formula I.

In a preferred embodiment, the compound according to Formula I, is incorporated into a pharmaceutical formulation along with one or more pharmaceutically acceptable diluent, excipient, or carrier, and which further optionally may be packaged as a kit. The present invention also encompasses a compound according to Formula I, or pharmaceutically acceptable derivatives, solvates, salts, tautomers and stereoisomers thereof, including mixtures thereof in all ratios, for use in therapy, such as treating a subject in need of inhibiting a kinase protein, wherein the subject has a proliferative or an inflammatory disease.

Methods for treating or preventing a disease or condition that is a member selected from cancers, tumor formation, angiogenesis, arteriosclerosis, ocular diseases, inflammatory diseases, arthritis, edema, and restinosis, among others, are included here. A method includes administering to a subject in need thereof a therapeutically effective amount of a compound of Formula I or a pharmaceutically acceptable salt, prodrug, hydrate, solvate, tautomer, enantiomer or racemic mix thereof.

Additional embodiments of the present invention include: a compound according to Formula I for use as a medicament; use of the compound according to Formula I for the preparation of a medicament for the treatment of a subject in need of inhibiting a kinase protein; and use of the compound according to Formula I for the preparation of a medicament for the suppression or reduction of cellular proliferation in single-site or metastatic cancers.

Also included within the scope of the invention are preparative compounds I-21, final product compounds I-33, and a pharmaceutically acceptable salt, prodrug, hydrate, solvate, tautomer, enantiomer or racemic mix thereof.

A method of synthesizing the compounds of the present invention also is encompassed within the present invention.

The present invention also is related to the combined use of a compound of Formula I together with further medicament active ingredient for the treatment of a subject in need of treatment for a kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory and hematological diseases, arthritis, thrombosis, fibrosis, glomerulonephritis, neurodegeneration, psoriasis, restenosis, wound healing, transplant rejection, metabolic diseases, autoimmune diseases, cirrhosis, diabetes and vascular and immune diseases in mammals.

The compounds of the present invention especially are useful as ATP-inhibitors of Aurora, TrkA, TrkB, Flt3(D835Y)(h), Ret(h), IRAK4(h), FAK(h), KDR9H0, PYK(2)(h) and Tie2(K849w) kineases for the treatment of solid tumors characterized by having the kinase strongly expressed or overexpressed. Such solid tumors include, among others, monocytic and acute myeloid leukaemia, brain, breast, pancreatic, ovarian, urogenital, lymphatic system, stomach, laryngeal and lung carcinoma, including lung adenocarcinoma and small-cell lung carcinoma.

Furthermore, the present invention provides pharmaceutical compositions and methods of modulating and/or inhibiting unregulated or disturbed Aurora, TrkA, TrkB, Flt3 (D835Y)(h), Ret(h), IRAK4(h), FAK(h), KDR9H0, PYK(2) (h) and/or Tie2(K849w) kinase activity in order to treat or cure proliferative diseases including all types of cancers comprising administering to a subject in need thereof an effective amount of a kinase inhibitor according to Formula I. In particular, the compounds of the Formula I are useful in the treatment of certain forms of cancer. The compounds of Formula I furthermore can be used to provide additive or synergistic effects in certain existing cancer chemotherapies, and/or can be used to restore the efficacy of certain existing cancer chemotherapies and radiotherapies.

The compounds of the present invention especially are useful as kinase inhibitors for the treatment of solid tumors characterized by having kinases that are strongly expressed or overexpressed. Such solid tumours include, among others, monocytic or acute myeloid leukaemia, brain, breast, pancreatic, ovarian, urogenital, thyroid and parathyroid, lymphatic system, stomach, laryngeal and lung carcinoma, including lung adenocarcinoma and small-cell lung carcinoma.

The compounds of the present invention have an antiproliferative action in vivo in a xenotransplant tumor model by their inhibitory action on cell division. Thus, when they are administered to a patient having a hyperproliferative disease, these compounds inhibit tumor growth, reduce inflammation associated with a lymphoproliferative disease, inhibit transplant rejection, inhibit neurological damage due to tissue repair, etc. The present compounds are suitable for prophylactic or therapeutic purposes. The prevention of proliferation is achieved by administration of the compounds according to the invention prior to the development of overt disease, for example to prevent the growth of tumors, prevent metastatic growth, diminish restenosis associated with cardiovascular surgery, etc. Alternatively, the compounds are used for the treatment of ongoing diseases by stabilizing or improving the clinical symptoms of the patient.

I. Definitions

As used herein, a description of the compounds of the invention in every case includes a pharmaceutically acceptable salt, solvate, hydrate, prodrug, tautomer, enantiomer, stereoisomer, analog or derivative thereof, including mixtures thereof in any ratios.

Where substituent groups are specified by their conventional chemical formulae, written from left to right, they optionally encompass substituents resulting from writing the structure from right to left, e.g., —$CH_2O$— optionally also recites —$OCH_2$—.

The term "alkyl", by itself or as part of another substituent, unless otherwise stated means an unbranched (linear) or branched chain, or a cyclic hydrocarbon radical, or combination thereof, having 1, 2, 3, 4, 5, 6, 7, 8, 9 or 10 C atoms. The term preferably denotes methyl, ethyl, propyl, isopropyl, butyl, isobutyl, sec-butyl or tert-butyl, pentyl, or hexyl, and includes cycloalkyl and bicycloalkyl, e.g. cyclopropyl, cyclobutyl, cyclopentyl, cyclohexyl, cycloheptyl, norbornene, and the like. One to seven hydrogen atoms in an alkyl chain as defined may be replaced by F, Cl and/or Br, and/or one or two $CH_2$ groups may be replaced by O, S, SO, $SO_2$ and/or CH=CH groups.

The term "alkylene" denotes an optionally substituted, unbranched (linear) or branched chain that by itself or as part of another substituent means a divalent radical derived from an alkane, as exemplified by —$CH_2CH_2CH_2$—. "Alkylene" preferably denotes methylene, ethylene, propylene, isopropylene, butylene, isobutylene, sec-butylene or tert-butylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, or difluoromethylene. Especially preferred is an alkylene having 1, 2, 3, 4, 5 or 6 C atoms, preferably methylene, ethylene, propylene, isopropylene, butylene, isobutylene, sec-butylene, tert-butylene, pentylene, hexylene, difluoromethylene, tetrafluoroethylene or 1,1-difluoroethylene.

A "cyclic alkylene" ("cycloalkylene") preferably denotes cyclopropylene, cyclobutylene, cyclopentylene, cyclohexylene or cycloheptylene.

The term "aryl" means, unless otherwise stated, means a polyunsaturated, aromatic, single ring or multiple rings, preferably from 1 to 3 rings, the latter of which are fused together or linked covalently. The term "aryl" denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino) phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl including difluorophenyl, o-, m- or p-bromophenyl including dibromophenyl, o-, m- or p-chlorophenyl including dichlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl) phenyl, o-, m- or p-[2-(morpholin-4-yl)ethoxy]phenyl, o-, m- or p-[3-(N,N-diethylamino)propoxy]phenyl, o-, m- or p-(3-(3-diethylamino-propyl)ureidolphenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N, N-dimethylamino- or 3-nitro-4-N,N-dimethyl-aminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

In a preferred embodiment, "aryl" preferably denotes a phenyl that is unsubstituted or mono-, di- or trisubstituted independently by one or more halogens, OR, CN, $CONH_2$ or a heterocycle, where R is H, alkyl or alkyl chain comprising one or more heteroatoms; or where the substituents join with the carbon atoms of the phenyl to which they are bound to form a second ring, thereby providing a bicyclic structure.

The term "heteroaryl" refers to an aryl ring that contains from one to four heteroatoms selected from N, O, S, Si, P and B, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 7-azaindole, 1-isoquinolyl, 5-isoquinolyl, 2-quinoxalinyl, 5-quinoxalinyl, 3-quinolyl, 6-quinolyl, 1-piperidinyl, 3-benzofuranyl, and 4-benzodioxinyl. Substituents for each of the above noted aryl and heteroaryl ring systems are selected from the group of acceptable substituents described below.

For brevity, the term "aryl" when used in combination with other terms, such as for example, aryloxy, arylthioxy, or arylalkyl, optionally includes both aryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Each of the terms "alkyl," "heteroalkyl," "aryl" and "heteroaryl" optionally include unsubstituted, mono-, di- or tri-unsubstituted forms of the indicated radical.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Substituents for the alkyl and heteroalkyl radicals, including those groups often referred to as alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, and —$R_1$, wherein $R_1$ is —OH, O-alkyl, —CN, -halo, —C(O)OH, —C(O)O(alkyl), —C(O)$NH_2$, —C(O)NH (alkyl), —C(O)N(alkyl)$_2$, —$CH_2OH$, —$CH_2O$(alkyl), —$CH_2NH_2$, —$CH_2NH$(alkyl), —CH—$_2$N(alkyl)$_2$, —$SO_2OH$, —$SO_2O$(alkyl), —$SO_2NH_2$, —$SO_2NH$(alkyl), and —$SO_2N$(alkyl)$_2$. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O) $CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OH, —O-alkyl, —CN, -halo, —C(O)OH, —C(O)O(alkyl), —C(O)NH$_2$,
—C(O)NH(alkyl), —C(O)N(alkyl)$_2$, —CH$_2$OH, —CH$_2$O (alkyl), —CH$_2$NH$_2$, —CH$_2$NH(alkyl),
—CH$_2$N(alkyl)$_2$, —SO$_2$OH, —SO$_2$O(alkyl), —SO$_2$NH$_2$, —SO$_2$NH(alkyl), and —SO$_2$N(alkyl)$_2$ As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes, norbornanes, and the like.

The term "treatment" as used herein refers both to prevention of a particular disease or treatment of a pre-existing condition.

The phrase "therapeutically effective amount" as used herein means that amount of a compound, material, or composition comprising a compound of the present invention which is effective for producing some desired therapeutic effect by simultaneous blocking or inhibiting of Aurora kinase receptors in a mammal, thereby blocking the biological consequences of that pathway in the treated cells, at a reasonable benefit/risk ratio applicable to any medical treatment. A typical therapeutically effective amount ranges between of from about 0.1-1000 mg, preferably 0.1-500 mg.

The term "pharmaceutically acceptable salts" includes salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *J. Pharma. Science* 1977, 66: 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. For instance, prodrugs for carboxylic acid analogs of the invention include a variety of esters. In an exemplary embodiment, the pharmaceutical compositions of the invention include a carboxylic acid ester. In another exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

As used herein, the term "heteroatom" includes oxygen (O), nitrogen (N), sulfur (S), silicon (Si), boron (B), and phosphorus (P).

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$-O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$-S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$-S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent may be attached to the remainder of the molecule directly or through a linker, wherein the linker is preferably alkyl. Examples of cycloalkyl include, but are not limited to, cyclopentyl, cyclohexyl, 1-cyclohexenyl, 3-cyclohexenyl, cycloheptyl, norbornanyl, norbornene, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, difluoromethyl, fluoromethyl, 2,2,2-trifluoroethyl, 4-chlorobutyl, 3-bromopropyl, and the like.

The terms "TEA", "DMF", "LDA", "DCM" and "TFA" used herein as reagents in the syntheses of compounds of the invention mean "tetraethylammonia", "N,N-dimethylformamide", "lithium diisopropylamine", "dichloromethane" and "trifluoroacetic acid", respectively.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The term "host" or "patient in need thereof" as used herein may be any mammalian species, for example a primate species, particularly humans; rodents; rabbits; horses, cows, sheep, dogs, cats, etc. Animal models are of interest for veterinary treatment and for experimental investigations, providing a model for treatment of human disease.

The susceptibility of a particular cell to treatment with the compounds according to the invention was determined by in vitro tests. Typically, a culture of the cell was combined with a compound according to the invention at various concentrations for a period of time that was sufficient to allow the active agents to induce cell death or to inhibit migration, usually between about one hour and one week. In vitro testing was carried out using cultivated cells from a biopsy sample. The viable cells remaining after the treatment then were counted.

Drug dosage depends upon the specific compound used, the specific disease, the patient status, etc. A therapeutic dose is typically sufficient considerably to reduce the undesired cell population in the target tissue while the viability of the patient is maintained. The treatment is generally continued until a reduction in cell population has occurred, for example, at least about 50% reduction in the cell burden, and may be continued until essentially no more undesired cells are detected in the body.

II. Pharmaceutical Compositions

While compounds of the present invention can be administered as the raw chemical, it is preferable to present them as a pharmaceutical composition. According to a further aspect, the present invention provides a pharmaceutical composition comprising a compound of Formula I or Formula Ia, or a pharmaceutically acceptable salt, hydrate or solvate thereof, together with one or more pharmaceutical carrier and optionally one or more other therapeutic ingredients. The carrier(s) are "acceptable" in the sense of being compatible with the other ingredients of the formulation and not deleterious to the recipient thereof. The term "pharmaceutically acceptable carrier" includes vehicles, diluents, excipients and other elements appropriate for incorporation into a pharmaceutical formulation.

A formulation of the compound or composition includes any suitable for parenteral (including subcutaneous, intradermal, intramuscular, intravenous, peritoneal and intraarticular), rectal, ionotophoretic, intranasal, inhalation, and oral (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof ("active ingredient") with the carrier that constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: *The Science and Practice of Pharmacy.*, A. R. Gennaro, ed. (1995), the entire disclosure of which is incorporated herein by reference.

Pharmaceutical compositions containing compounds of Formula I or Formula Ia may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 0.1 mg per day to about 7000 mg per day, preferably about 1 mg per day to about 100 mg per day, and more preferably, about 25 mg per day to about 50 mg per day, in single or divided doses. In some embodiments, the total daily dose may range from about 50 mg to about 500 mg per day, and preferably, about 100 mg to about 500 mg per day. It is further recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compressing or molding the compound of Formula I, optionally using one or more additional ingredient. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: *The Science and Practice of Pharmacy*, pages 1660-1675 (1995). It should be understood that in addition to the ingredients particularly mentioned above, the formulations of this invention may include other agents conventional in the art having regard to the type of formulation in question, for example those suitable for oral administration may include flavoring agents.

Formulations for parenteral administration include aqueous and non-aqueous sterile injection solutions that may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents, while formulations for oral administration also may include flavoring agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The pharmaceutically acceptable carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Exemplary formulations, are well known to those skilled in the art, and general methods for preparing them are found in any standard pharmacy school textbook, for example, Remington, *The Science and Practice of Pharmacy*, 21st Ed., (1995) Lippincott.

One aspect of the present invention contemplates the treatment of the disease/condition with the pharmaceutically active agent that may be sold in kit form. The kit comprises a compound of the present invention contained within a syringe, box, bag, and the like. Typically, the kit comprises directions for the administration of the compound. The kit form is particularly advantageous when different dosage concentrations and/or forms (e.g., oral and parenteral) are sold, or when titration of the individual components of the combination is desired by the prescribing physician, or when a compound of the present invention is to be administered with in combination with a further pharmaceutically active ingredient.

An example of such a kit is a so-called blister pack. Blister packs are well known in the packaging industry and are being widely used for the packaging of pharmaceutical unit dosage forms (tablets, capsules, and the like). They generally consist of a sheet of relatively stiff material covered with a foil of a preferably transparent plastic material. During the packaging process recesses are formed in the plastic foil. The recesses have the size and shape of the tablets or capsules to be packed. The tablets or capsules are placed in the recesses and the sheet of relatively stiff material is sealed against the plastic foil at the face of the foil which is opposite from the direction in which the recesses were formed. Particular dosage information normally is stamped onto each blister pack.

In another specific embodiment of the invention, a dispenser designed to dispense the daily doses one at a time in the order of their intended use is provided.

III. Methods Of Treatment Or Prevention

In a further aspect the invention provides a method for treating or preventing a disease or condition that is a member selected from kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases, autoimmune diseases, haematological diseases, cirrhosis, diabetes and vascular and immune diseases in mammals. The method includes administering to a subject in need thereof a therapeutically effective amount of a compound of Formula I or a pharmaceutically acceptable salt, hydrate, prodrug, tautormer, enantiomer, or racemic mix thereof:

Subjects for treatment according to the present invention include humans (patients) and other mammals in need of therapy for the stated condition.

Compounds of the invention possess unique pharmacological characteristics with respect to inhibition of cellular division and influence the activity of the Aurora kinase enzymes in cells. Therefore, these compounds are effective in treating conditions and disorders, especially cancer-related tumors and disorders, which are modulated by Aurora kinase activity. In one embodiment, compounds of the invention are associated with diminished side effects compared to other current standards of treatment.

Compounds of the invention are typically more selective than known anti-cancer drugs, and demonstrate higher selectivity for inhibiting Aurora kinase activity. The compounds also exhibit an advantageous profile of activity including good bioavailability. Accordingly, they offer advantages over many art-known methods for treating disorders associated with unregulated or disturbed Aurora kinase activity.

IV. General Syntheses

The compounds of the invention are prepared in general by methods known to those of skill in the art for synthesizing analogous compounds. These are illustrated by the general schemes indicated below, and the preparative examples that follow. Most starting materials are commercially available from supply companies like Aldrich Chemicals Co. or Sigma Chemical Company, as examples. Compounds that are not commercially available may be synthesized by those of skill in the art by following procedures given in references such as "Organic Reactions," Volumes 1-40, John Wiley & Sons (1991); "Rodd's Chemistry of Carbon Compounds," Volumes 1-5 and Suppl., Elsevier Science Publishers (1989); "Fieser and Fieser's Reagents for Organic Synthesis," Volume 1-15, John Wiley & Sons (1991); "Advanced Organic Chemistry," Jerry March, John Wiley & Sons, 4$^{th}$ Ed. (1992); Lücking et al, ChemMedChem 2007, 2, 63-77; and Nicolaou. et al. Agew. Chem. Int. Ed. 2005, 44, 4490-4527. All macrocyclic compounds of the present invention were synthesized by processes developed by the inventors.

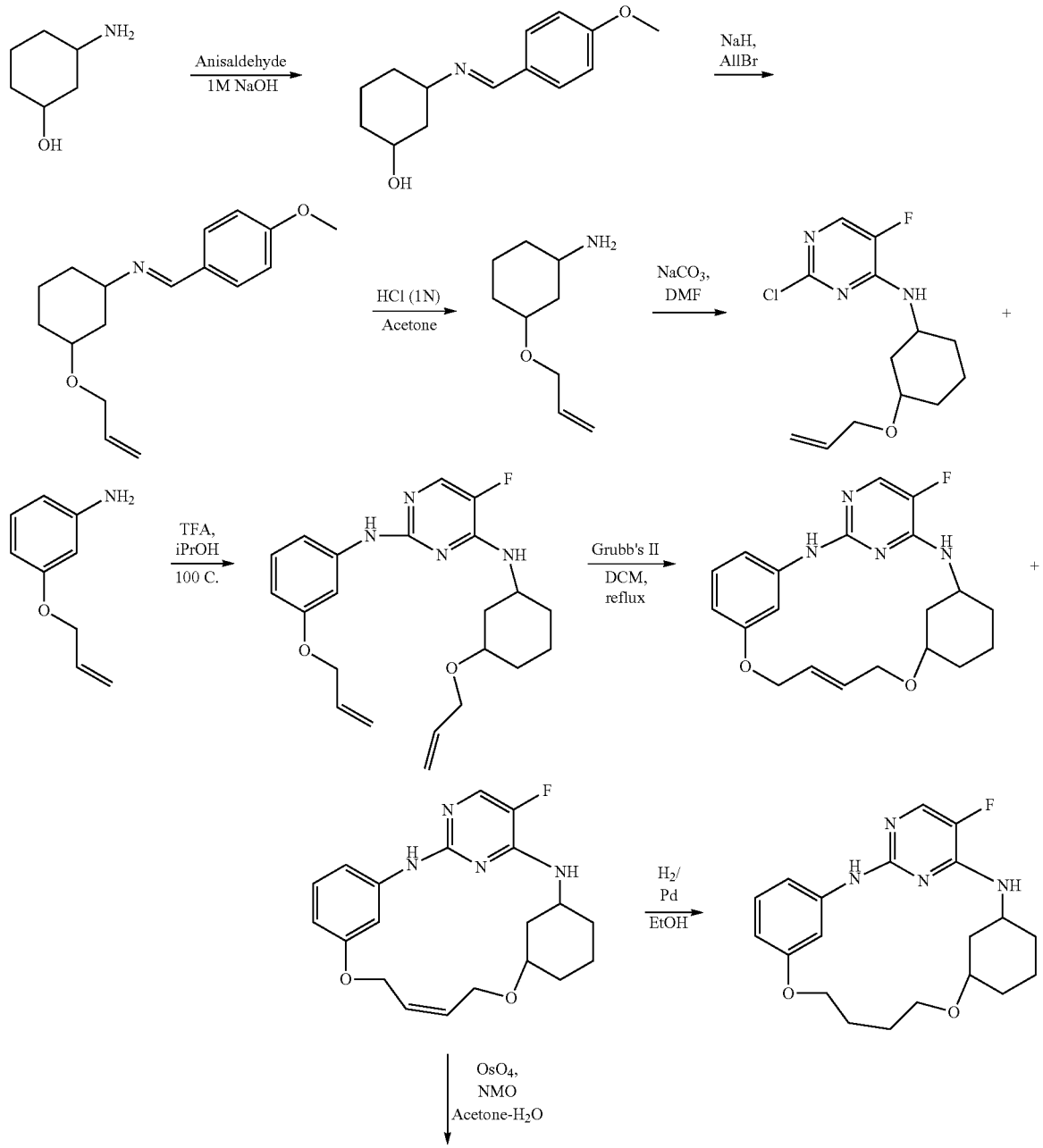

Scheme 1

23
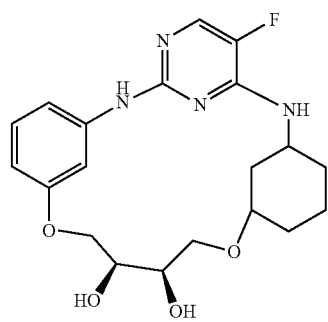
24
-continued
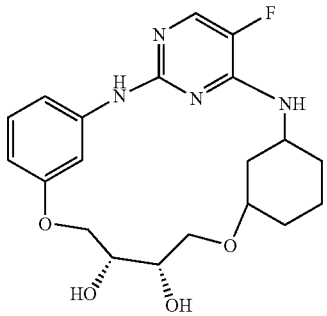
Scheme 2
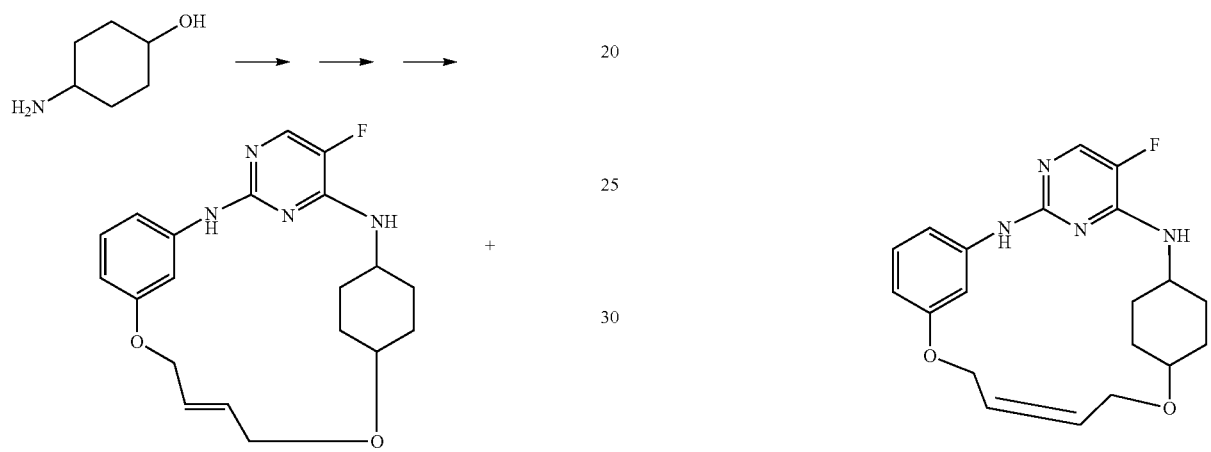
Scheme 3
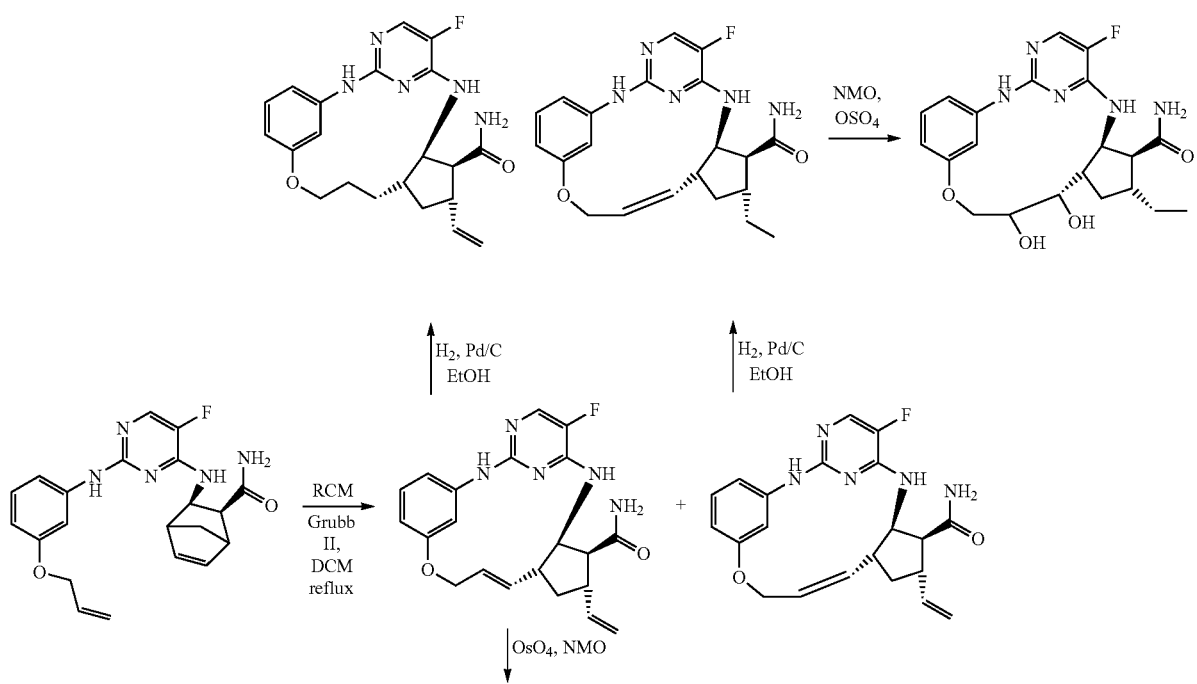

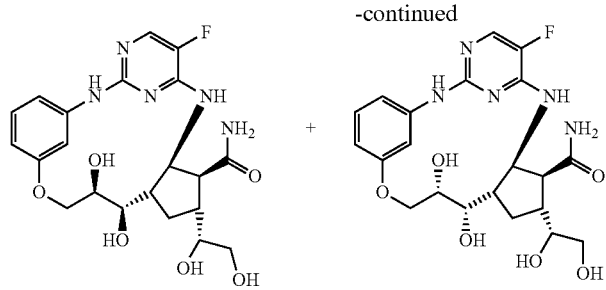
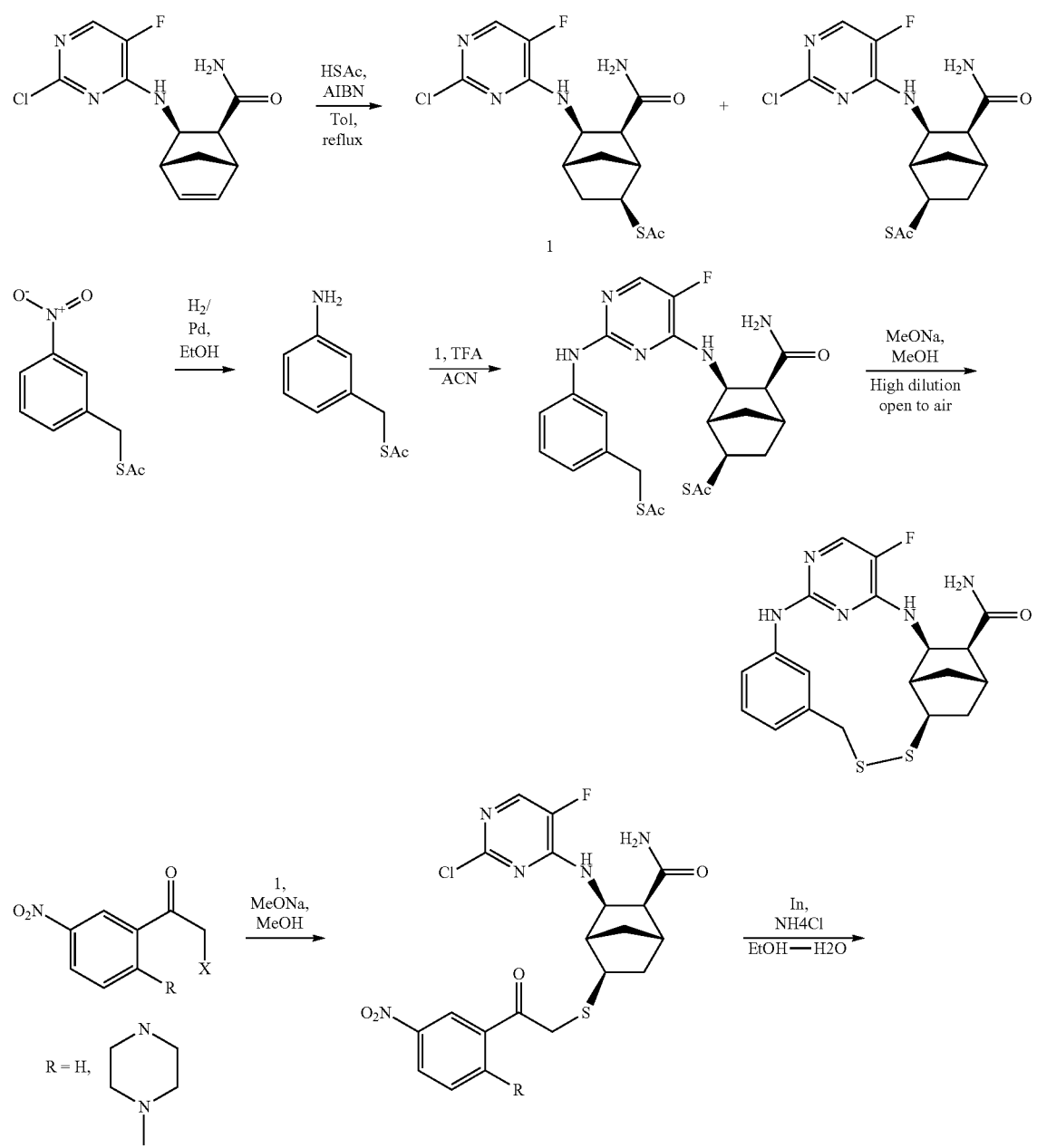

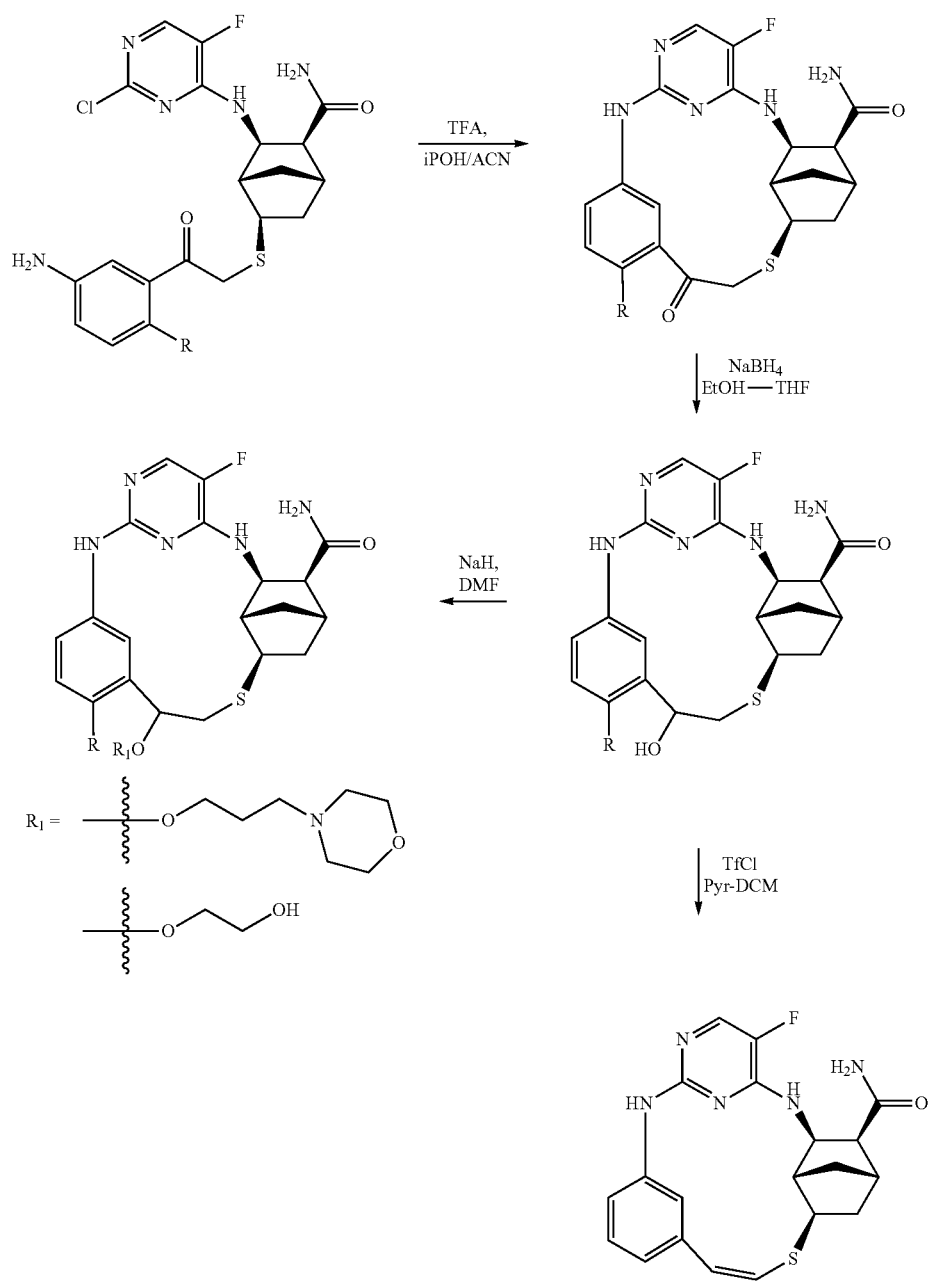
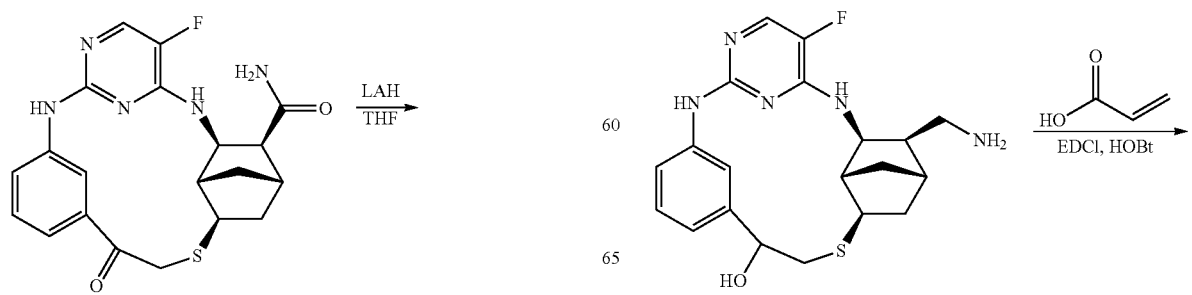

29
-continued
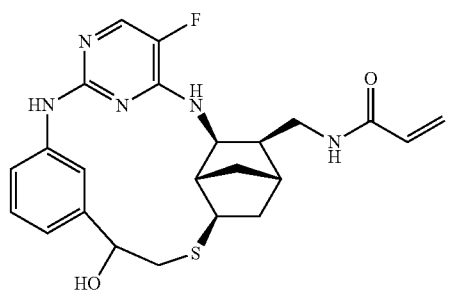
30
-continued
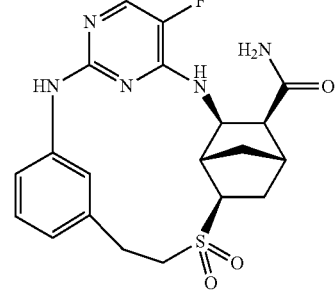
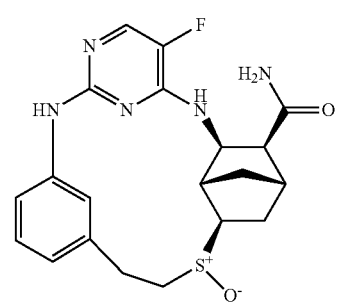
Scheme 5a
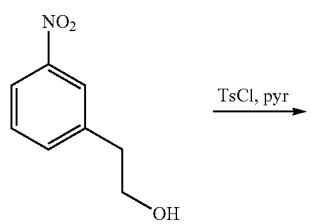
Scheme 5b
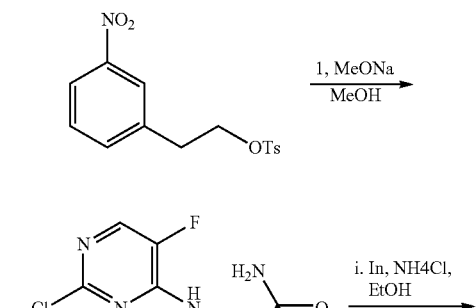
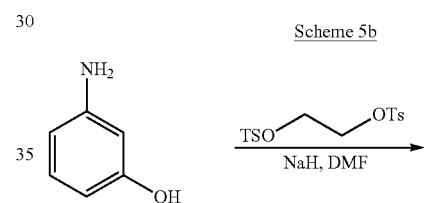
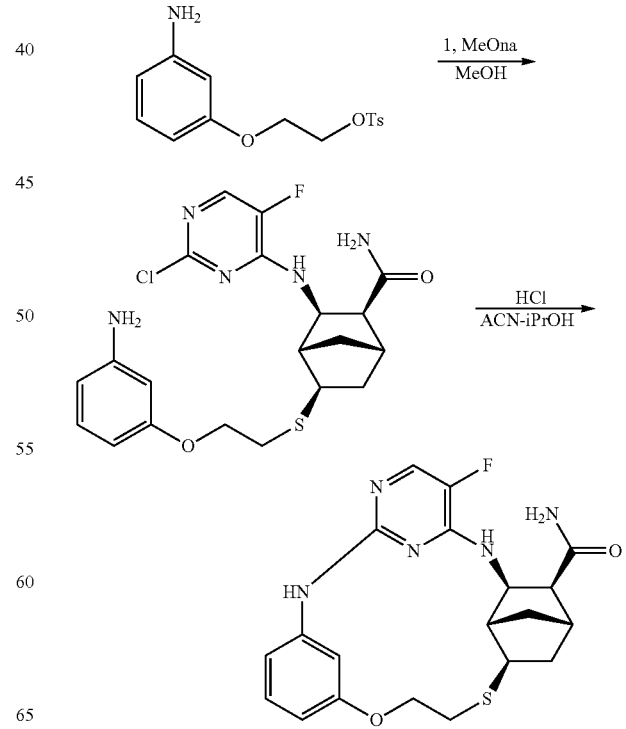

Scheme 5c
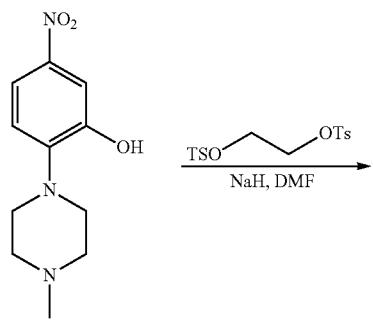
↓ TsO⌢OTs, NaH, DMF
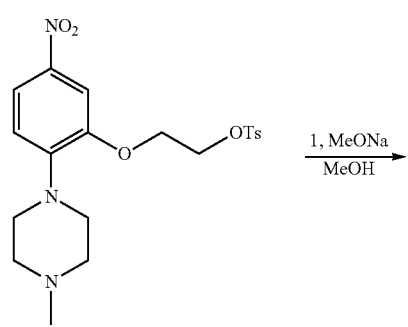
↓ 1, MeONa, MeOH
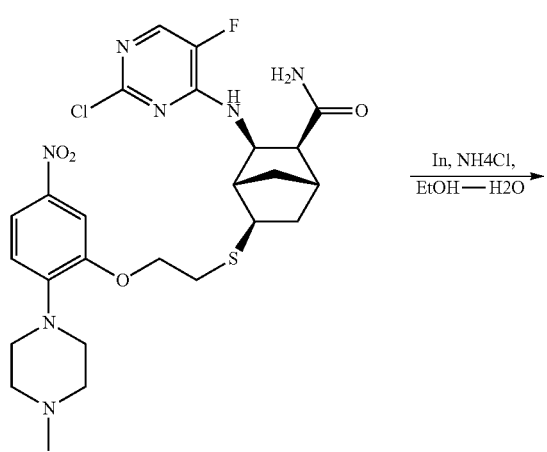
↓ In, NH4Cl, EtOH—H2O
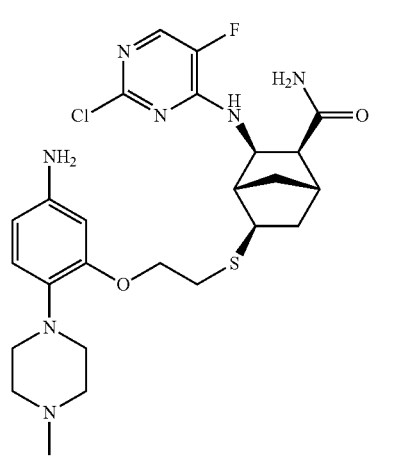
↓ TFA, ACN-iPrOH
Scheme 5d
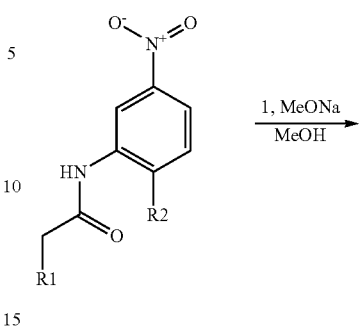
↓ 1, MeONa, MeOH
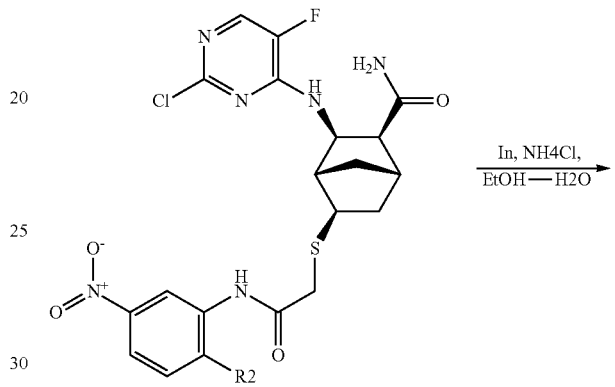
↓ In, NH4Cl, EtOH—H2O
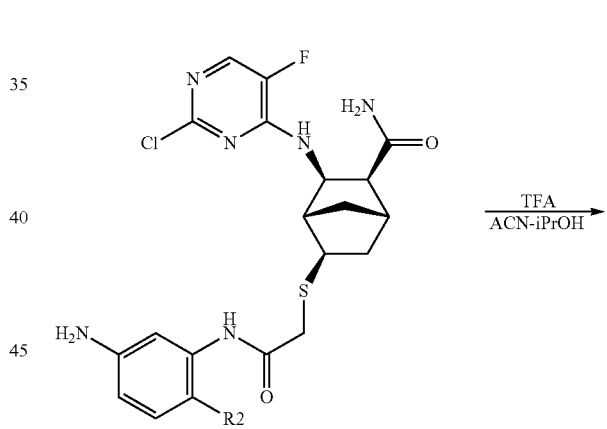
↓ TFA, ACN-iPrOH
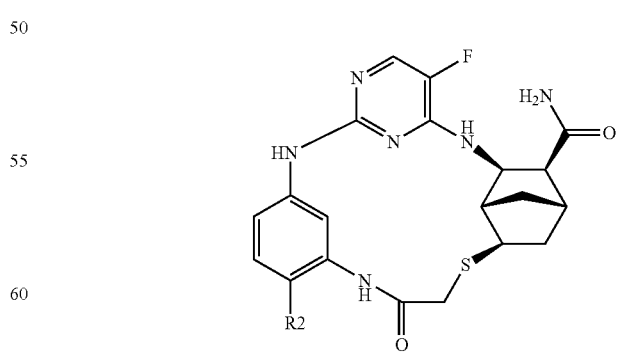
R1 = Cl, R2 = H
R1 = Br, R2 = 4-methyl piperazine
R1 = Br, R2 = CN Scheme 5e
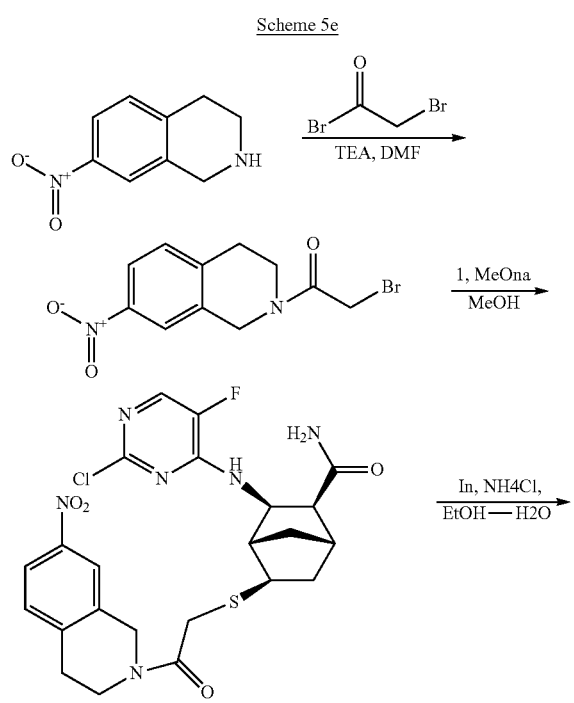
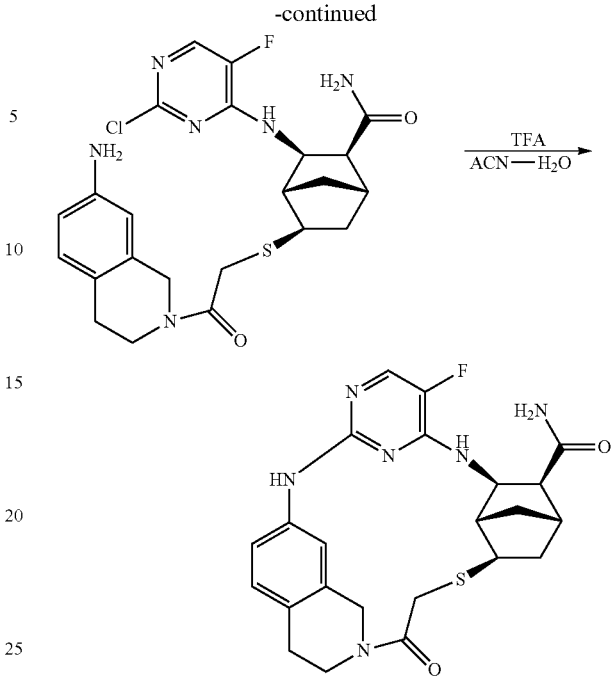
Scheme 6
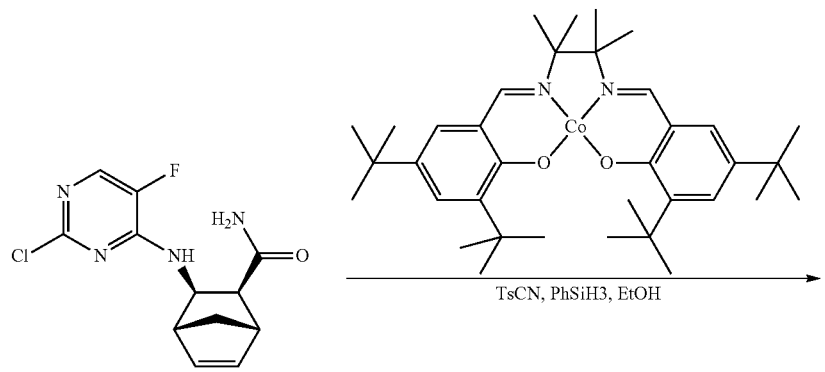
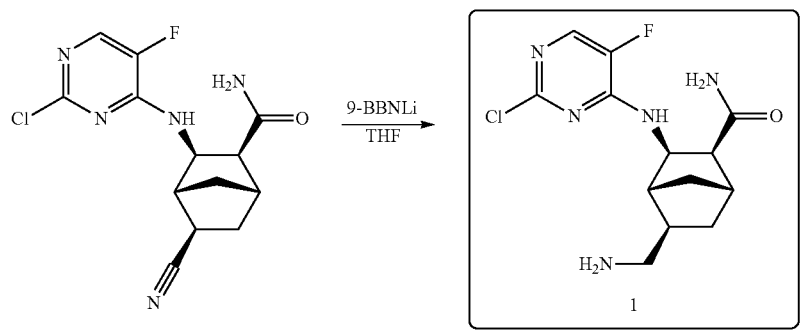

-continued
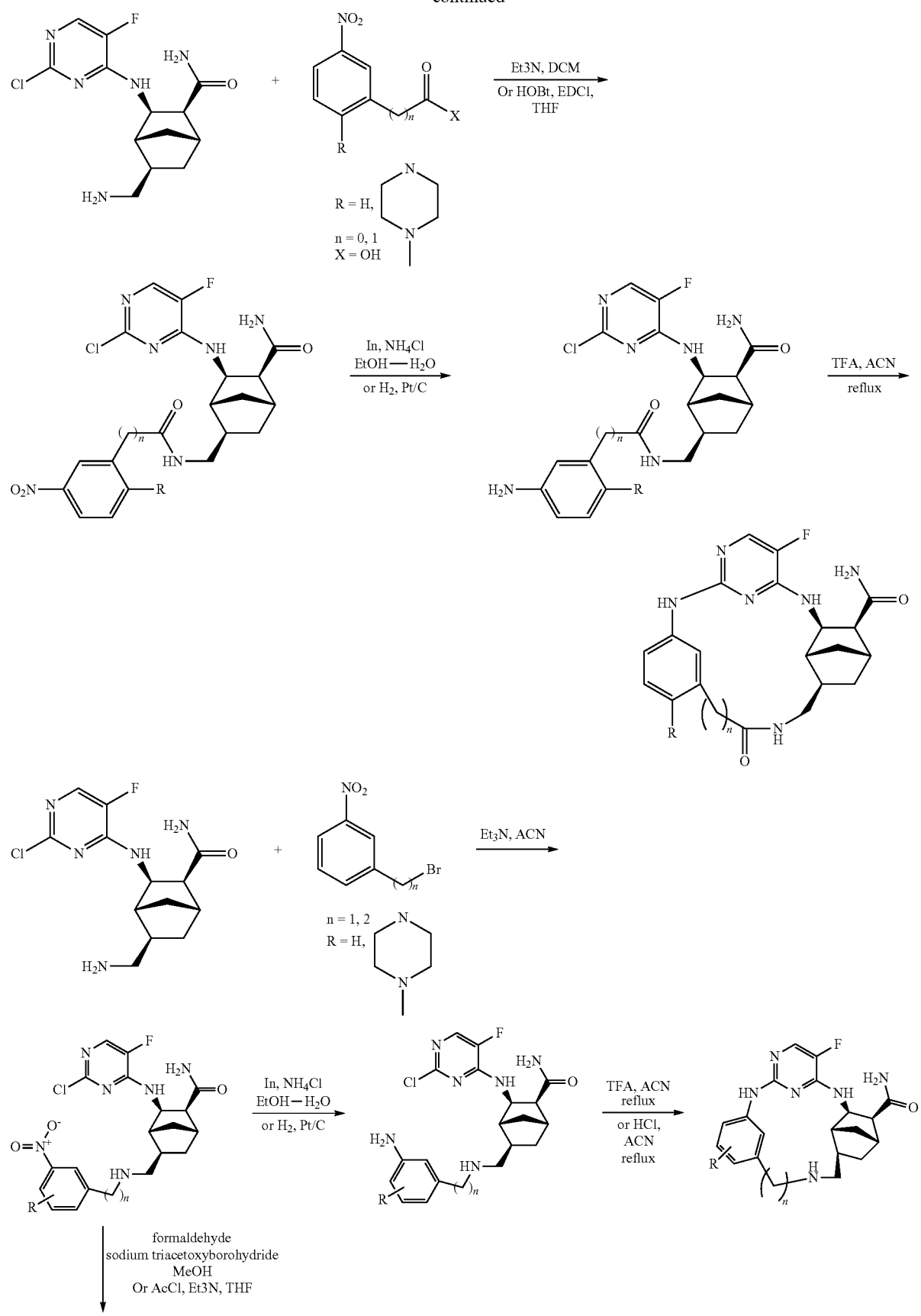

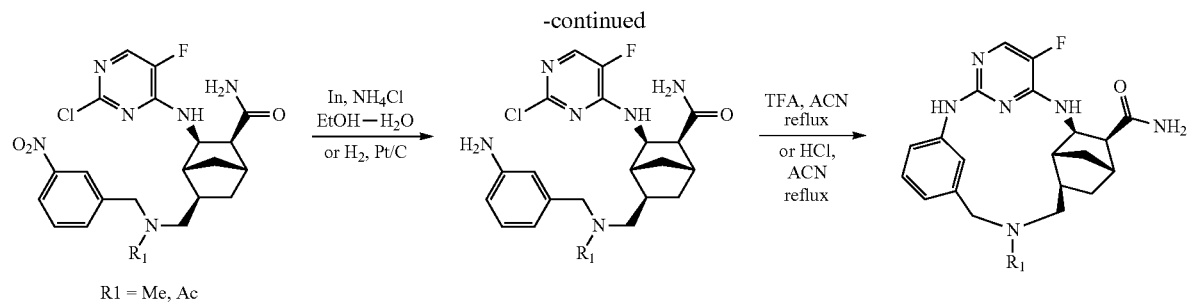
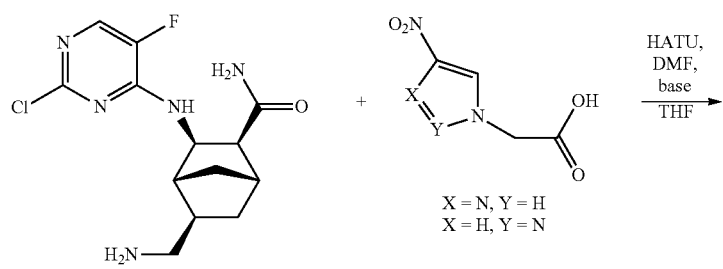
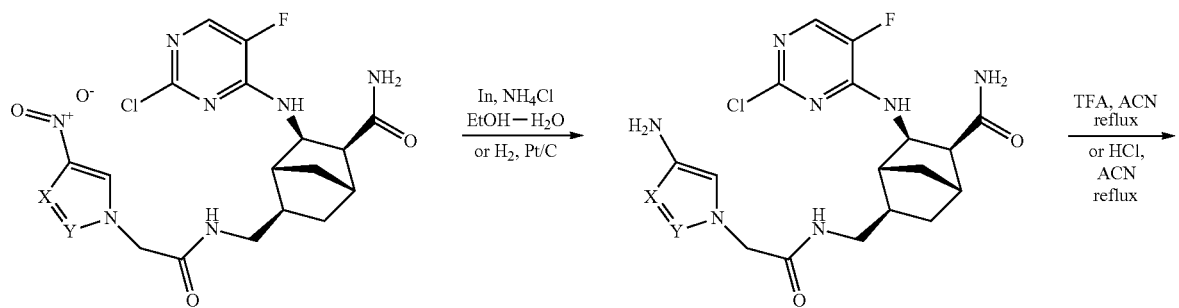
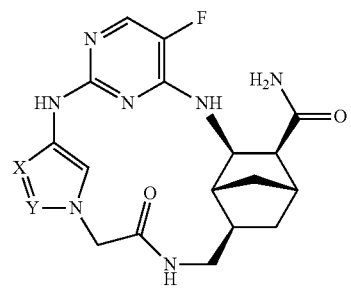
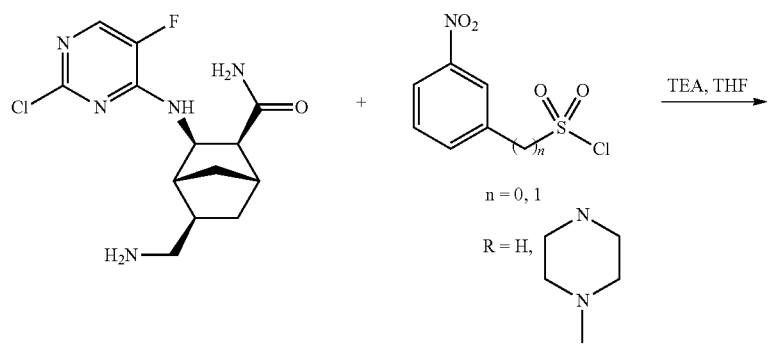

-continued
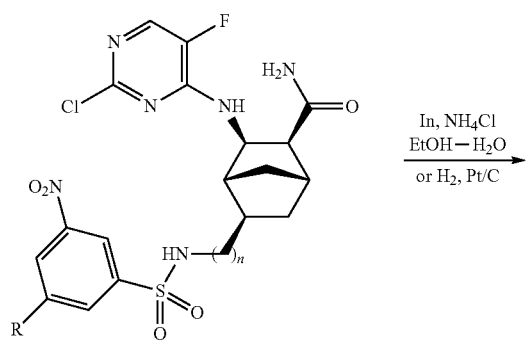
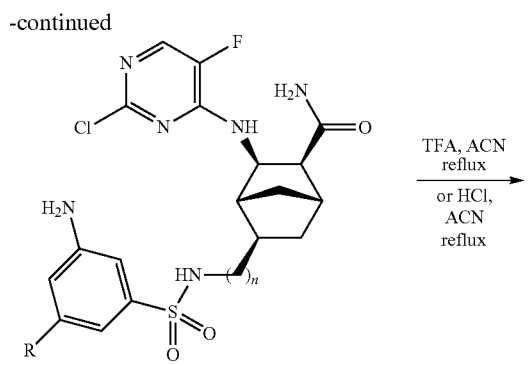
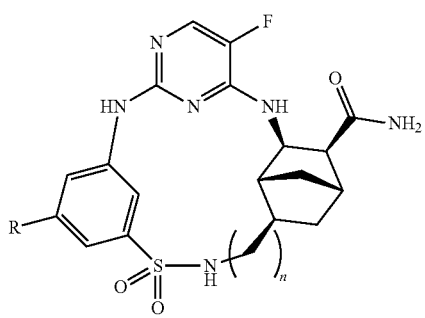
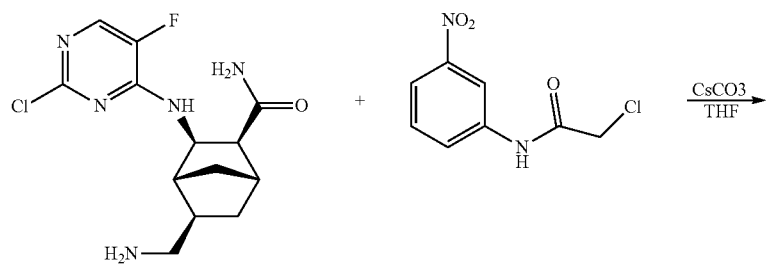
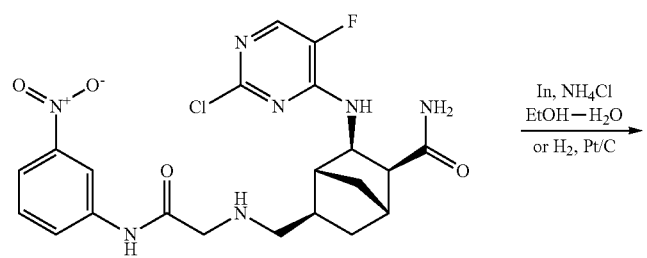
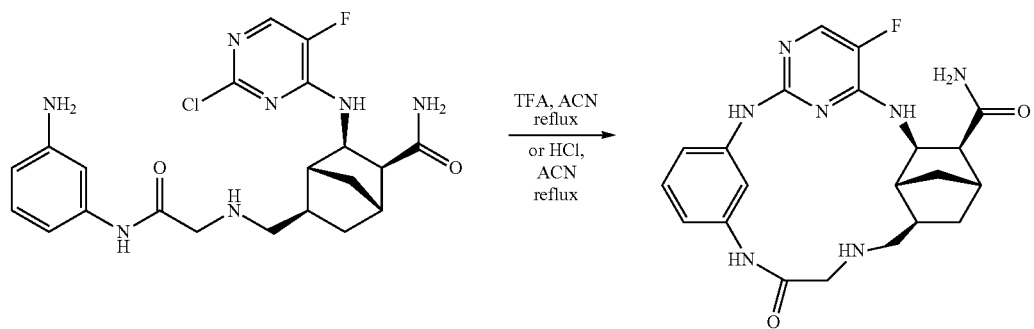

-continued
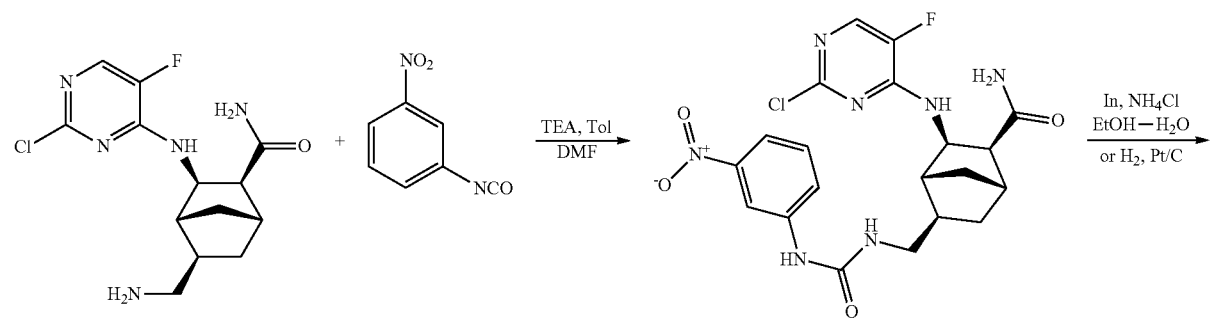
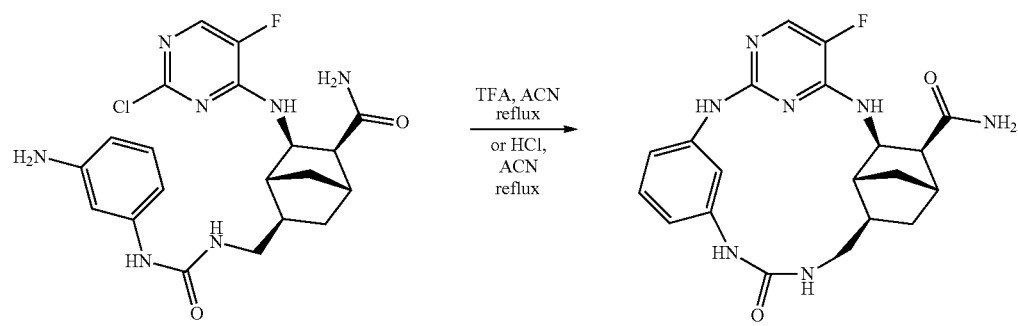
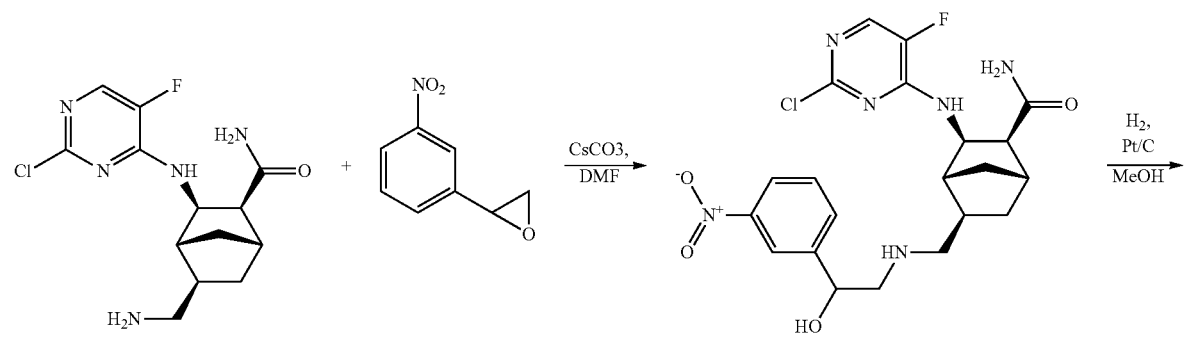
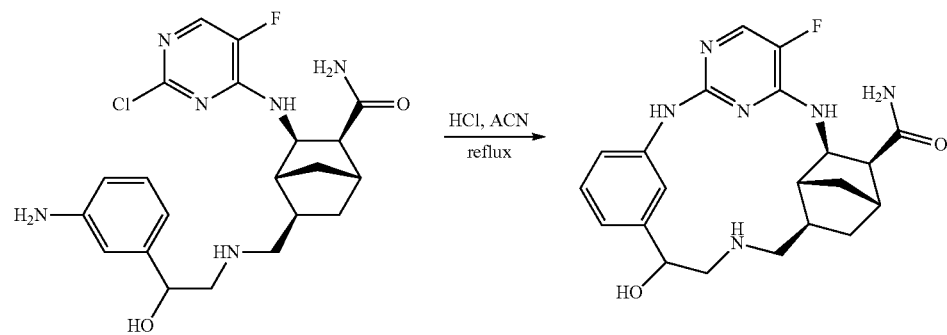

Scheme 7
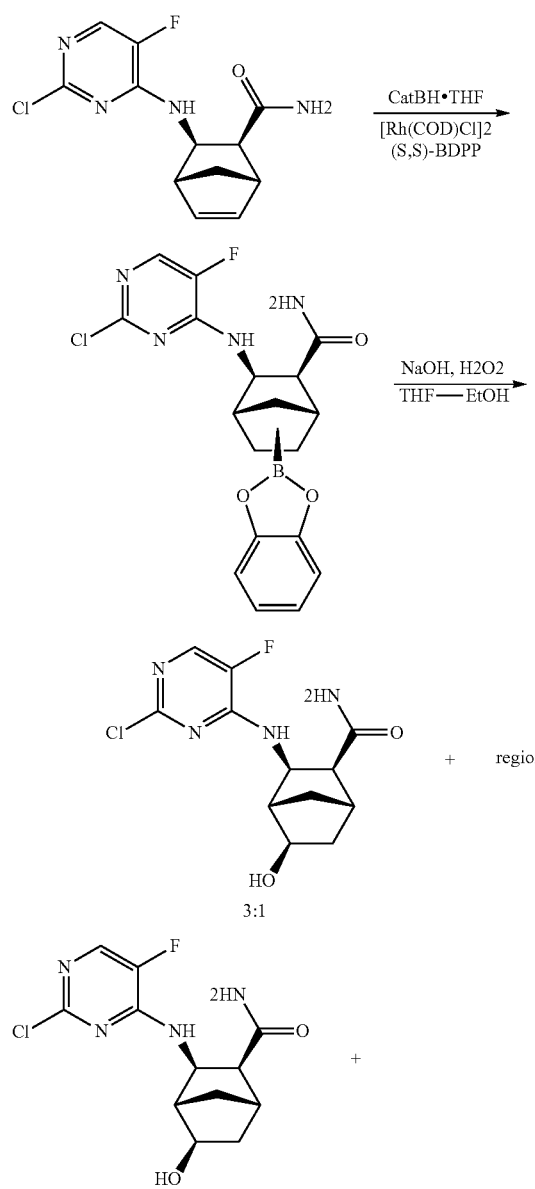
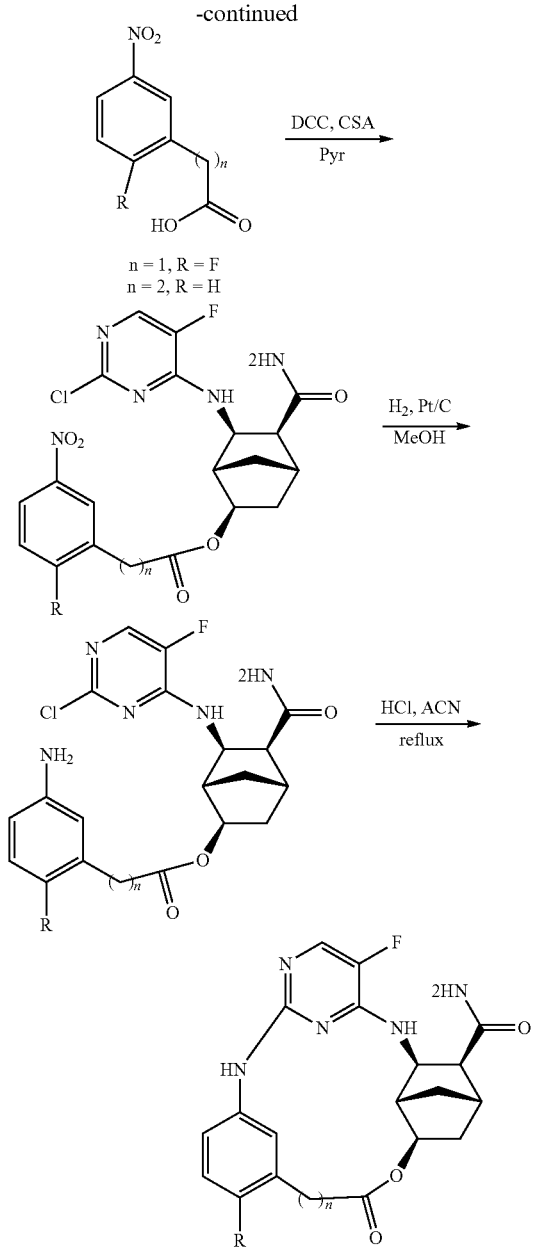
Scheme 8
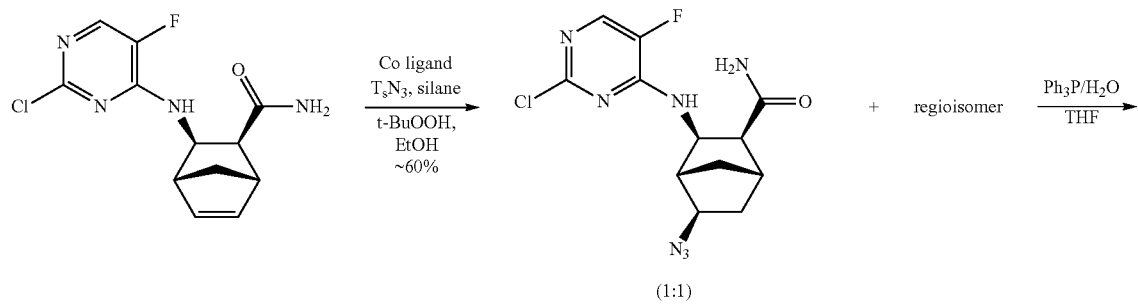

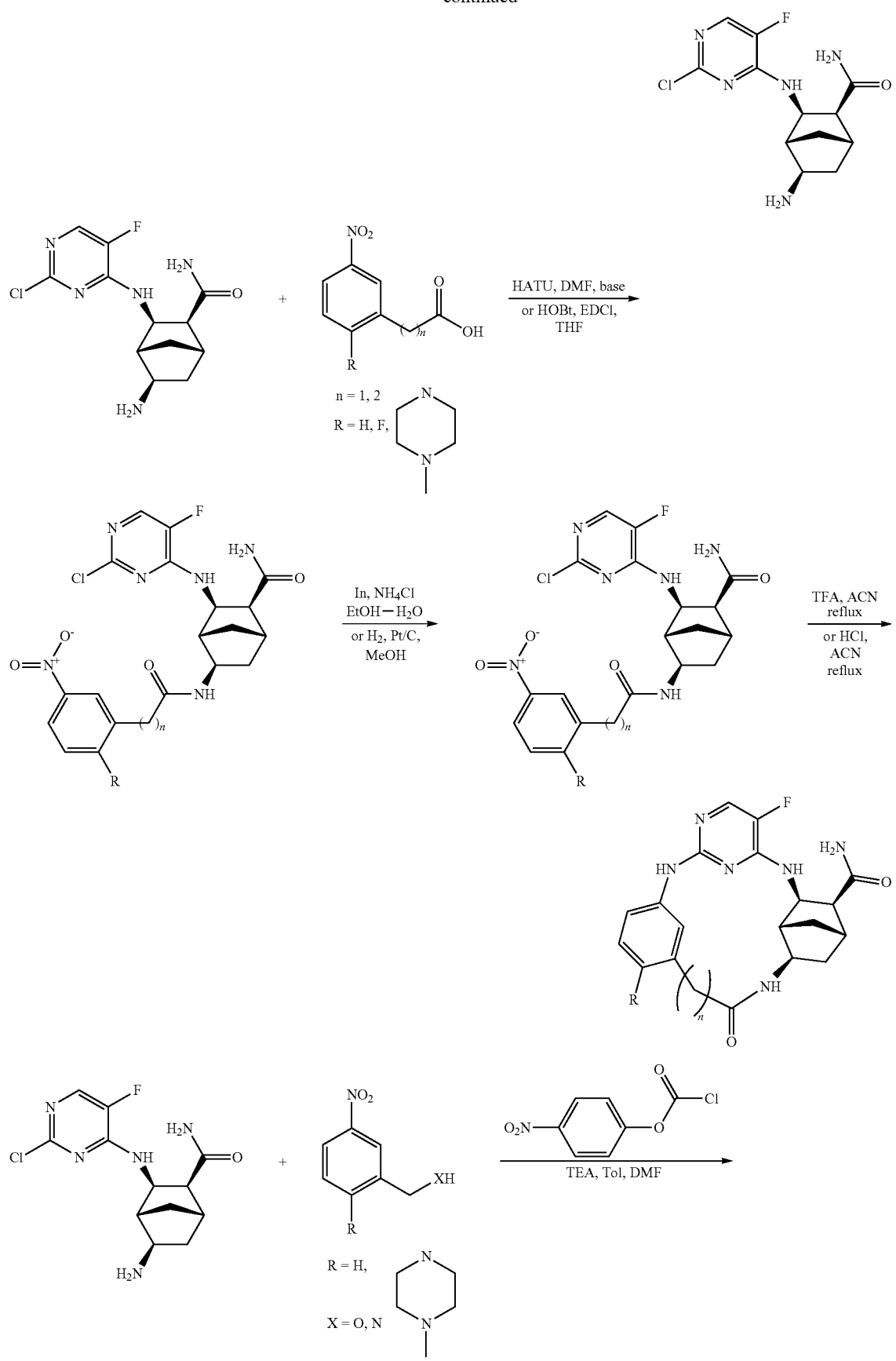

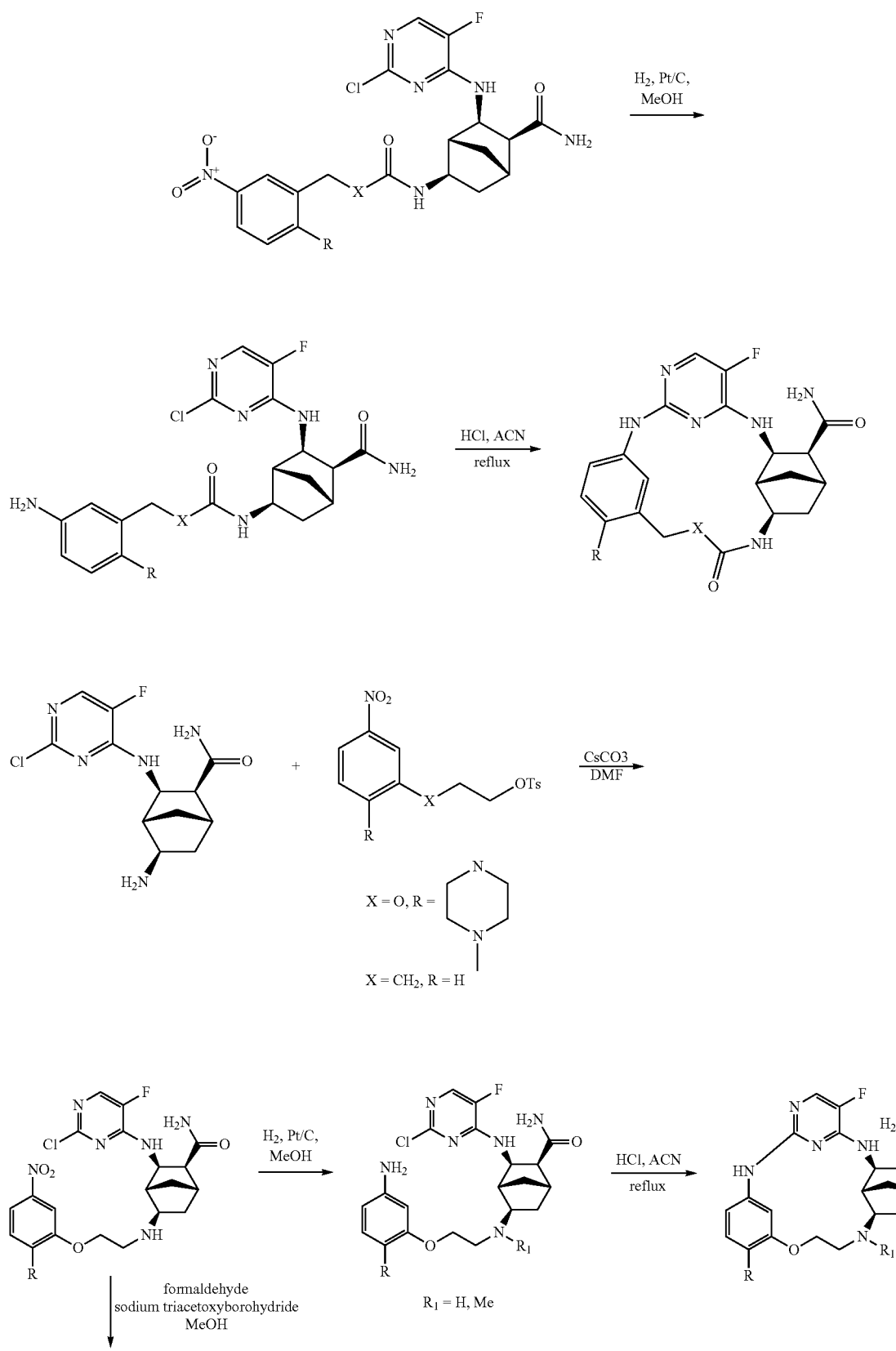

-continued
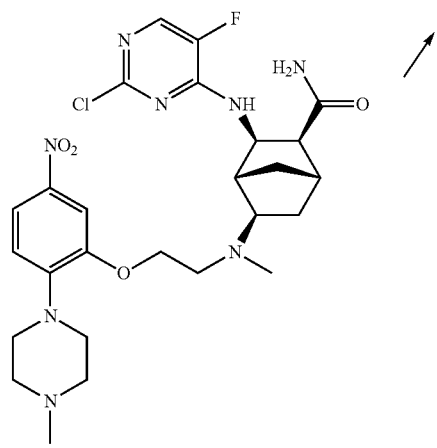
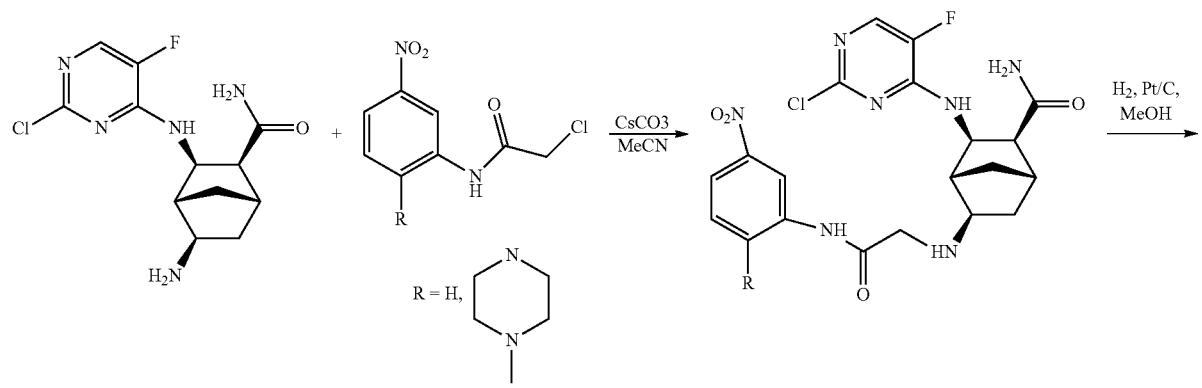
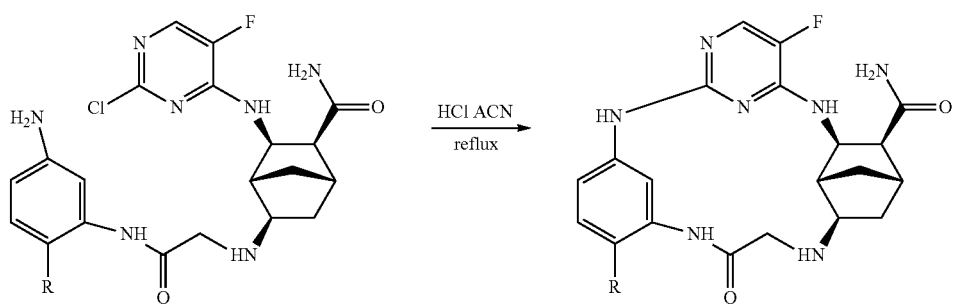
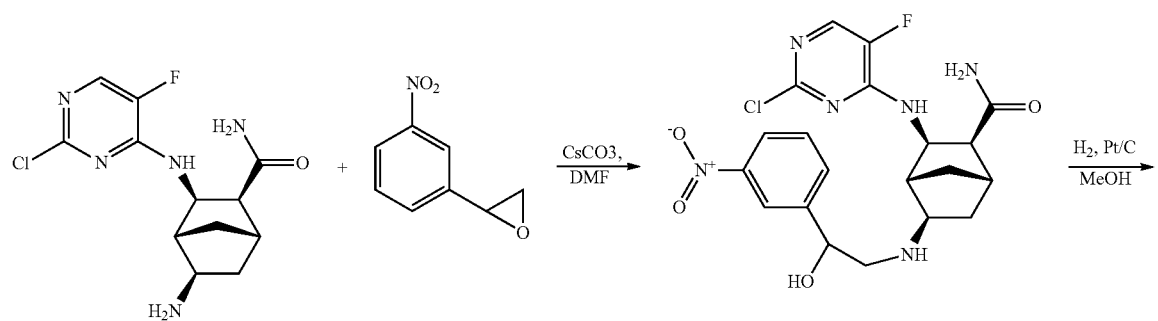

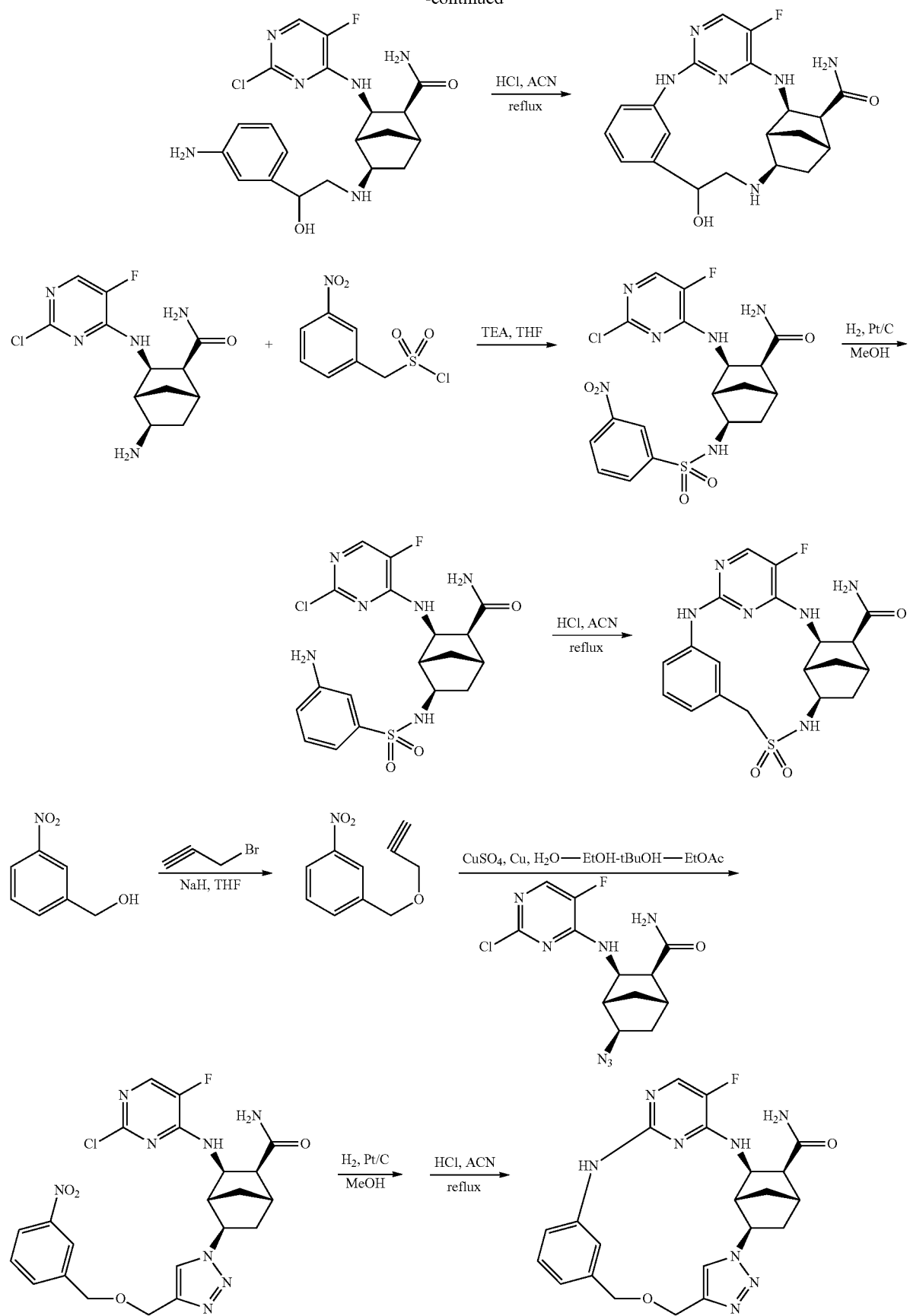

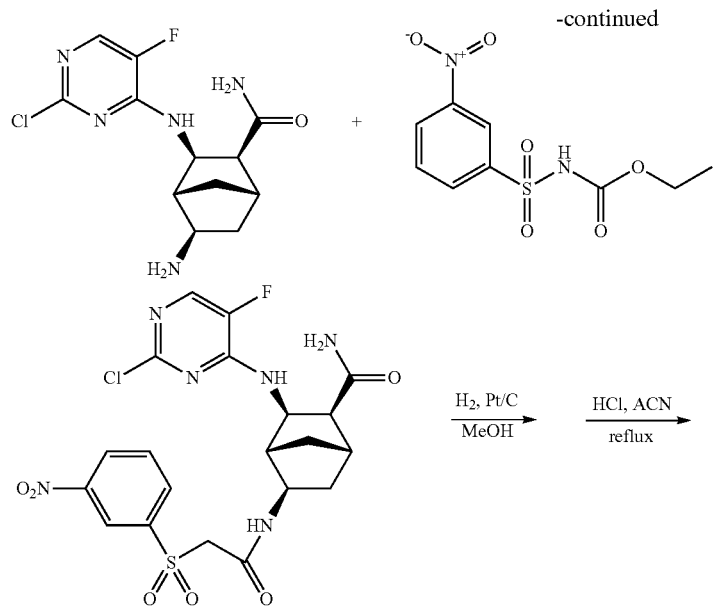

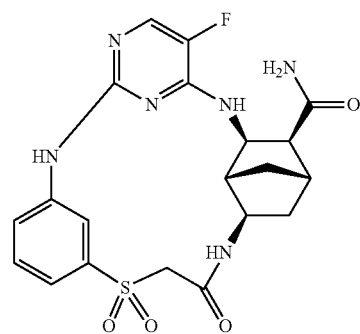

Procedure A: Nitro Reduction to Aniline Via Indium Catalysis

A nitro aryl compound is dissolved in a mixture of 4:1 ethanol/water solution (10 mL). To this solution was added ammonium chloride, and indium (0) metal grains. The reaction flask was heated to reflux. Reactions were generally complete within 2-3 hours. Upon completion, the reaction mixture was filtered to remove insolubles, the concentrated. The crude mixture was set aside for cyclization without further purification.

Procedure B: Nitro Reduction to Aniline Via H-Cube Hydrogenater

A nitro aryl compound is dissolved in ~20 mL methanol, then passed through the H-Cube Hydrogenator at 45° C. using a 5% Pt/C cartridge at 1 mL/min The crude aniline was concentrated and used for cyclization without further purification.

Procedure C: Amidation Via HATU

Into a round bottom flask was added the amine (1 eq), carboxylic acid (1.5 eq), and N-[(1H-1,2,3-benzotriazol-1-yloxy)(dimethylamino)methylene]-N-methylmethanaminium hexafluorophosphate (HATU, 1.5 eq). This dry mixture was dissolved in dimethylformamide (3.00 ml), to which N-ethyl-N-isopropylpropan-2-amine (3 eq) was then added. The reaction mixture was allowed to stir overnight at room temperature for 15 hours. The desired product was purified by diluting the reaction mixture with ~50 mL ethyl acetate, extracting with 2:1 brine:water solution. Back extracted aqueous once, combined organic layers. The combined organic extracts were dried over magnesium sulfate, filtered and concentrate. The crude was further purified by flash chromatography with a hexane/ethylacetate/methanol gradient to afford the desired product.

Procedure D: Urea or Carbamate Formation Via 4-Nitrophenyl Chloridocarbonate

Into a clean dry vial with a stir bar was dissolved the alcohol/amine #1 (2 eq) in toluene (3.00 ml). To this mixture was added N,N-diethylethanamine (2 eq) followed by 4-nitrophenyl chloridocarbonate (2 eq) via syringe. The reaction mixture is allowed to stir at room temperature. After 30 minutes, a solution of amine #2 (1 eq) in 1 mL dimethylformamide is added to the reaction solution. The reaction mixture is allowed to stir at room temperature for 2 hours. The reaction mixture was then concentrated and purified by prep RP-HPLC to afford the desired product.

Analytical LC/MS

Analytical LC/MS was performed using the following two methods:

Method A: A Discovery® $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/Vis diode array detector G1315B (Agilent) and Finnigan LCQ Duo MS detector in ESI+ modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry® $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ modus with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Preparative HPLC

Preparative HPLC was performed using either a Waters Atlantis™ $dC_{18}$ OBD™ 10 μM (30×250 mm) column or a Waters Sunfire™ Prep $C_{18}$ OBD™ 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min)

The following examples are provided to illustrate selected embodiments of the invention and are not to be construed as limiting its scope.

PREPARATIVE EXAMPLES

Synthesis of Building Blocks

Example I

3-{[1-(4-Methoxy-phenyl)-meth-(E)-ylidene]-amino}-cyclohexanol

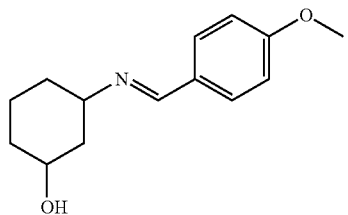 [SMILES: COc1ccc(/C=N/C2CCCC(O)C2)cc1]

To a vigorously stirred solution of 3-aminocyclohexanol (0.9 g, 7.81 mmol) in aqueous sodium hydroxide (1 mL, 1 M) at rt was added 4-methoxybenzaldehyde (1.12 g, 8.20 mmol). The reaction mixture was stirred for 30 min The solids were collected by vacuum filtration, washed with water, and then dried to afford crude 3-{[1-(4-Methoxy-phenyl)-meth-(E)-ylidene]-amino}-cyclohexanol which was used without further manipulation.

Example II (3-Allyloxy-cyclohexyl)-[1-(4-methoxy-phenyl)-meth-(E)-ylidene]-amine

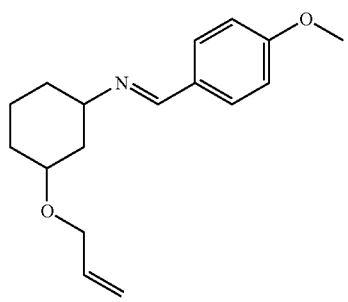 [SMILES: C=CCOC1CCCC(/N=C/c2ccc(OC)cc2)C1]

A suspension of 3-{[1-(4-Methoxy-phenyl)-meth-(E)-ylidene]-amino}-cyclohexanol (200 mg, 0.86), allyl bromide (149 L, 1.71 mmol), and sodium hydride, 60% dispersion in mineral oil (60%, 69 mg, 1.71 mmol) in DMF (4 mL) was stirred at rt. After 24 h, the reaction was quenched with MeOH, diluted with EtOAc and wash with H2O, brine. The organic layer was dried with solid sodium sulfate. It was then concentrated to afford (3-Allyloxy-cyclohexyl)-[1-(4-methoxy-phenyl)-meth-(E)-ylidene]-amine, which was used without further purification.

Example III

3-Allyloxy-cyclohexylamine

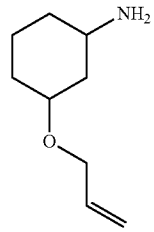

A solution of (3-Allyloxy-cyclohexyl)-[1-(4-methoxy-phenyl)-meth-(E)-ylidene]-amine (100 mg, 0.37 mmol) in acetone (2 mL) was heated to reflux. Aqueous hydrochloric acid (0.25 mL, 1 M) was then added and it was heated to reflux for another 30 min The reaction mixture was partitioned between aqueous hydrochloric acid (1 M) and ethyl acetate. The aqueous phase was treated with aqueous concentrated sodium hydroxide until basic, and then was extracted with ethyl acetate. The organic phase was concentrated under reduced pressure to afford 3-Allyloxy-cyclohexylamine.

Example IV (3-Allyloxy-cyclohexyl)-(2-chloro-5-fluoro-pyrimidin-4-yl)-amine

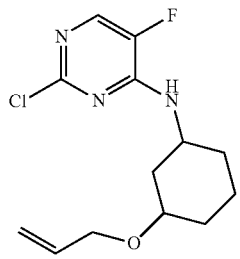 [SMILES: C=CCOC1CCCC(Nc2nc(Cl)ncc2F)C1]

A mixture of 3-Allyloxy-cyclohexylamine (200 mg, 1.29 mmol), sodium bicarbonate (216 mg, 2.58 mmol), and 2,4-dichloro-5-fluoropyrimidine (237 mg, 1.42 mmol)l) in EtOH-water (1:1, 4 mL) was stirred at 70° C. for 40 h. The reaction mixture was cooled, and small amount of iPOH was added. The product was crystallized and filtered to a crude product. The crude product was purified by flash column on silica gel to afford 260 mg product.

Example V

N*4*-(3-Allyloxy-cyclohexyl)-N*2*-(3-allyloxy-phenyl)-5-fluoro-pyrimidine-2,4-diamine

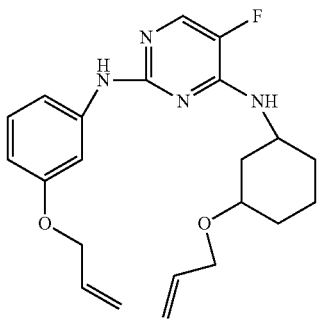 [SMILES: C=CCOc1cccc(Nc2ncc(F)c(NC3CCCC(OCC=C)C3)n2)c1]

A pressure vessel charged with a solution of (3-Allyloxy-cyclohexyl)-(2-chloro-5-fluoro-pyrimidin-4-yl)-amine 130 mg, 0.45 mmol), 3-(allyloxy)aniline (102 mg, 0.68 mmol), and TFA (84 μL, 1.14 mmol) in isopropanol (2 mL) was sealed and heated at 100° C. overnight. The reaction mixture was cooled and subjected to flash chromatography on silica gel to afford N*4*-(3-Allyloxy-cyclohexyl)-N*2*-(3-allyloxy-phenyl)-5-fluoro-pyrimidine-2,4-diamine (79 mg). LC/MS [method A, retention time 4.71 min; m/z 399.2 (M+1)].

Example VI 4-(4-methoxybenzylideneamino)cyclohexanol

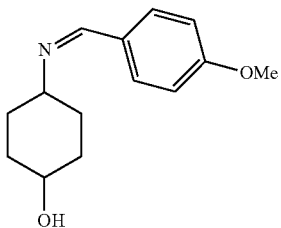 [SMILES: COc1ccc(/C=N\C2CCC(O)CC2)cc1]

To a vigorously stirred solution of 4-aminocyclohexanol (1 g, 8.68 mmol) in aqueous sodium hydroxide (1 mL, 1 M) at rt was added 4-methoxybenzaldehyde (1.24 g, 9.12 mmol). The reaction mixture was stirred for 30 min. The solids were collected by vacuum filtration, washed with water, and then dried to afford 4-(4-methoxybenzylideneamino)cyclohexanol (1.80 g) which was used without further manipulation.

Example VII (4-(allyloxy)-N-(4-methoxybenzylidene)cyclohexanamine

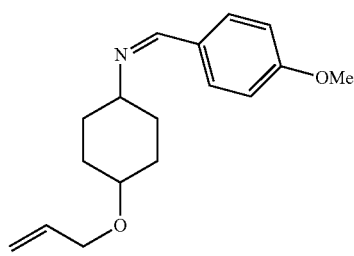 [SMILES: C=CCOC1CCC(/N=C\c2ccc(OC)cc2)CC1]

A suspension of 4-(4-methoxybenzylideneamino)cyclohexanol (1 g, 4.29 mmol), allyl bromide (1.87 mL, 21.4 mmol), and sodium hydride, 60% dispersion in mineral oil (857 mg, 21.4 mmol) in DMF (20 mL) was stirred at rt. After 3 d, the reaction was quenched with MeOH, diluted with EtOAc and wash with H2O, brine. The organic layer was dried with solid sodium sulfate. It was then concentrated to afford (4-(allyloxy)-N-(4-methoxybenzylidene)cyclohexanamine, which was used without further purification.

Example VIII 4-(allyloxy)cyclohexanamine

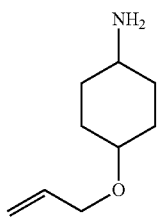

A solution of 4-(allyloxy)-N-(4-methoxybenzylidene)cyclohexanamine (1.20 g, 4.39 mmol) in acetone (20 mL) was heated to reflux. Aqueous hydrochloric acid (2.5 mL, 1 M) was then added and heating to reflux was continued for another 30 min The reaction mixture was partitioned between aqueous hydrochloric acid (1 M) and ethyl acetate. The aqueous phase was treated with aqueous concentrated sodium hydroxide until basic, and then was extracted with ethyl acetate. The organic phase was concentrated under reduced pressure to afford 4-(allyloxy)cyclohexanamine (630 mg).

Example IX

N-(4-(allyloxy)cyclohexyl)-2-chloro-5-fluoropyrimidin-4-amine

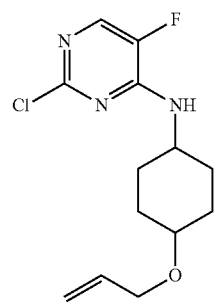 [SMILES: C=CCOC1CCC(Nc2nc(Cl)ncc2F)CC1]

A mixture of 4-(allyloxy)cyclohexanamine (500 mg, 2.58 mmol), sodium bicarbonate (433 mg, 5.15 mmol), and 2,4-dichloro-5-fluoropyrimidine (473 mg, 2.83 mmol) in DMF (13 mL) was stirred at 70° C. for 40 h. The reaction mixture was cooled, and small amount of iPOH was added. The product was crystallized and filtered.

Example X $N^4$-(4-(allyloxy)cyclohexyl)-$N^2$-(3-(allyloxy)phenyl)-5-fluoropyrimidine-2,4-diamine

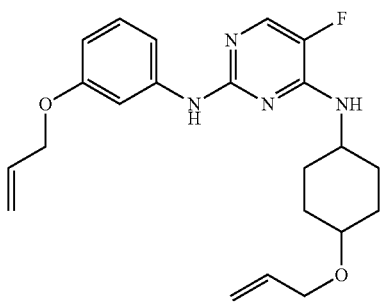 [SMILES: C=CCOc1cccc(Nc2ncc(F)c(NC3CCC(OCC=C)CC3)n2)c1]

A pressure vessel charged with a solution of N-(4-(allyloxy)cyclohexyl)-2-chloro-5-fluoropyrimidin-4-amine (300 mg, 1.05 mmol), 3-(allyloxy)aniline (235 mg, 1.57 mmol), and TFA (194 µL, 2.62 mmol) in isopropanol (5 mL) was sealed and heated at 100° C. overnight. The reaction mixture was cooled and subjected to flash chromatography on silica gel to afford $N^4$-(4-(allyloxy)cyclohexyl)-$N^2$-(3-(allyloxy)phenyl)-5-fluoropyrimidine-2,4-diamine (brown solid, 180 mg). LC/MS [method A, retention time 4.84 min; m/z 399.4 (M+1)].

Example XI (1S,2S,3R,4R)-3-(2-(3-(allyloxy)phenylamino)-5-fluoropyrimidin-4-ylamino)bicyclo[2.2.1]hept-5-ene-2-carboxamide

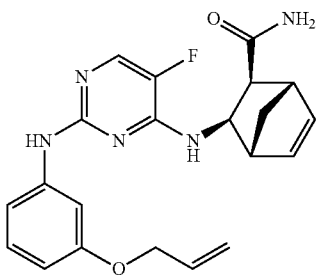 [SMILES: C=CCOc1cccc(Nc2ncc(F)c(N[C@H]3[C@@H](C(N)=O)[C@@H]4C=C[C@H]3C4)n2)c1]

A pressure vessel charged with a stir bar, (1S,2S,3R,4R)-3-(2-chloro-5-fluoropyrimidin-4-ylamino)bicyclo[2.2.1]hept-5-ene-2-carboxamide (500 mg, 1.77 mmol), 3-(vinyloxy)aniline (290 mg, 1.95 mmol), trifluoroacetic acid (327 µL, 4.42 mmol) and isopropanol (9 mL) was sealed and heated at 100° C. overnight. The solids were collected by vacuum filtration to afford (1S,2S,3R,4R)-3-(2-(3-(allyloxy)phenylamino)-5-fluoropyrimidin-4-ylamino)bicyclo[2.2.1]hept-5-ene-2-carboxamide (grey solid, 0.50 g). LC/MS [method A, retention time 4.49 min; m/z 396.1 (M+1)].

Example XII

S-(1S,2R,4S,5S,6S)-5-carbamoyl-6-(2-chloro-5-fluoropyrimidin-4-ylamino)bicyclo[2.2.1]heptan-2-ylethanethioate

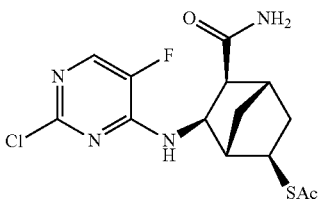

A mixture of (1S,2S,3R,4R)-3-[(2-chloro-5-fluoropyrimidin-4-yl)-amino]bicyclo[2.2.1]hept-5-ene-2-carboxamide (10 g, 35.37 mmol), thioacetic acid (2.77 mL, 38.9 mmol), and azobisisobutyronitrile (581 mg, 3.54 mmol) in toluene (180 mL) was heated to reflux overnight under nitrogen. The reaction mixture was then concentrated under reduced pressure and the residue was subjected to flash chromatography on silica gel using hexanes/ethyl acetate to separate the two regioisomeric products. 2.5 g of S-{(1S,2R,4S,5S,6S)-5-(aminocarbonyl)-6-[(2-chloro-5-fluoropyrimidin-4-yl)amino]bicyclo[2.2.1]hept-2-yl}ethanethioate was obtained. LC/MS [method B, retention time 5.31 min; m/z 359.0 (M+1)].

Example XIII

S-(1S,2S,3S,4S,5R)-3-[(2-chloro-5-fluoropyrimidin-4-yl)amino]-5-{[2-(3-nitrophenyl)-2-oxoethyl]thio}bicyclo[2.2.1]heptane-2-carboxamide

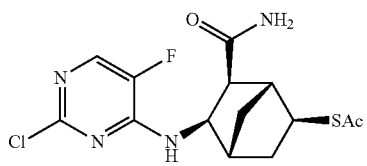

The above chromatography also afforded the 3.9 g of S-(1S,2S,3S,4S,5R)-3-[(2-chloro-5-fluoropyrimidin-4-yl)amino]-5-{[2-(3-nitrophenyl)-2-oxoethyl]thio}bicyclo[2.2.1]heptane-2-carboxamide. LC/MS [method B, retention time 5.15 min; m/z 359.0 (M+1)].

Example XIV

Thioacetic acid S-{3-[4-((1S,2S,3S,4S,6R)-6-acetylsulfanyl-3-carbamoyl-bicyclo[2.2.1]hept-2-ylamino)-5-fluoro-pyrimidin-2-ylamino]-benzyl}ester

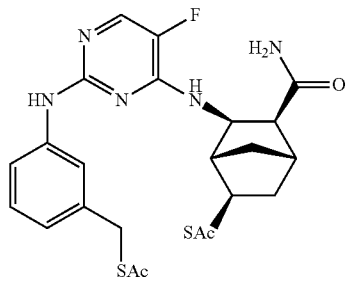

To a solution of thioacetic acid S-(3-nitro-benzyl) ester (1 g, 4.7 mmol) in EtOH (10 mL) was added Pd/C (10%, cat. Amount). The mixture was stirred under hydrogen (30 Psi). overnight. The mixture was filter and concentrated to afford thioacetic acid S-(3-amino-benzyl) ester in its crude form.

The crude thioacetic acid S-(3-amino-benzyl) ester was used to synthesize Thioacetic acid S-{3-[4-((1S,2S,3S,4S,6R)-6-acetylsulfanyl-3-carbamoyl-bicyclo[2.2.1]hept-2-ylamino)-5-fluoro-pyrimidin-2-ylamino]-benzyl}ester using the method described in Example 11.

Example XV (1S,2S,3S,4S,5R)-3-(2-chloro-5-fluoropyrimidin-4-ylamino)-5-(2-(3-nitrophenyl)-2-oxoethylthio)bicyclo[2.2.1]heptane-2-carboxamide

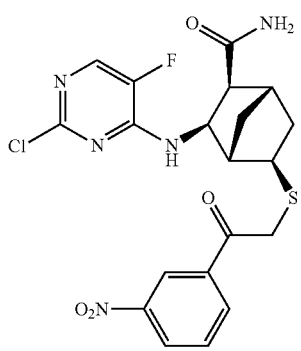 [SMILES: NC(=O)[C@H]1[C@H]2C[C@@H]([C@H]1Nc1nc(Cl)ncc1F)[C@H](SCC(=O)c1cccc([N+](=O)[O-])c1)C2]

To a suspension of S-{(1S,2R,4S,5S,6S)-5-(aminocarbonyl)-6-[(2-chloro-5-fluoropyrimidin-4-yl)amino]bicyclo[2.2.1]hept-2-yl}ethanethioate (300 mg, 0.84 mmol) in anhydrous methanol (5 mL) was added sodium methoxide solution (0.3 mL, ~30% in methanol) and the resulting mixture was stirred at rt for 30 min. The reaction mixture was then treated with 2-bromo-3'-nitroacetophenone (306 mg, 1.25 mmol) and stirring at rt overnight. The reaction mixture was diluted with methanol, neutralized by the addition of strongly acid cation-exchange resin (hydrogen form), filtered, and then concentrated under reduced pressure. The resultant residue was subjected to flash chromatography on silica gel to afford (1S,2S,3S,4S,5R)-3- [(2-chloro-5-fluoropyrimidin-4-yl)amino]-5-{[2-(3-nitrophenyl)-2-oxoethyl]thio}bicyclo[2.2.1]heptane-2-carboxamide (230 mg).

LC/MS [method A, retention time 5.69 min; m/z 480.0 (M+1)].

Example XVII

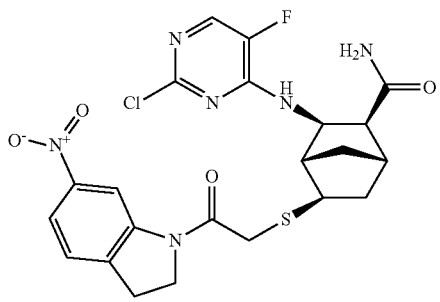 [SMILES: NC(=O)[C@H]1[C@H]2C[C@@H]([C@H]1Nc1nc(Cl)ncc1F)[C@H](SCC(=O)N1CCc3ccc([N+](=O)[O-])cc31)C2]

The compound was prepared in a similar procedure as described in Example 25 below. LC/MS [method A, retention time 4.99 min; m/z 521.1 (M+1)].

Example XVIII (1S,2S,3R,4R)-3-[(2-chloro-5-fluoropyrimidin-4-yl)amino]-5-cyanobicyclo[2.2.1]heptane-2-carboxamide

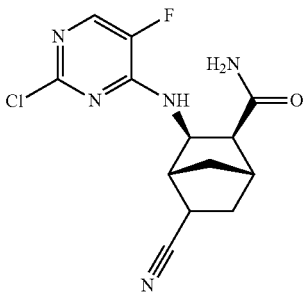 [SMILES: N#CC1C[C@@H]2C[C@H]1[C@@H](Nc1nc(Cl)ncc1F)[C@H]2C(N)=O]

Catalyst Cobalt ligand complex (43.00 mg; 0.07 mmol) (prepared as described in *J. Am. Chem. Soc.* 2006, 128, 11693-11712) was dissolved in ethanol (2 ml) at ambient temperature under nitrogen in a round bottom flask equipped with a stir bar. After 2 min, (1S,2S,3R,4R)-3-[(2-chloro-5-fluoropyrimidin-4-yl)amino]bicyclo[2.2.1]hept-5-ene-2-carboxamide (2.00 g; 7.07 mmol) was added to the stirring red solution followed by 4-methylbenzenesulfonyl cyanide (41 mg; 8.49 mmol). Phenylsilane (0.87 ml; 7.07 mmol; 1.00 eq.) was then added dropwise. The resulting red homogeneous mixture was stirred at room temperature for 45 minutes.

The reaction mixture was concentrated, taken up onto silica and loaded onto a silica column for flash chromatography, using a gradient of 0-80% ethyl acetate in hexanes, to give the desired product in 490 mg, 22% yield). LC/MS [method B, retention time 4.1 min; m/z 310.0 (M+1)].

Example XIX 1R,2S,3R,4R,5R)-5-(aminomethyl)-3-(2-chloro-5-fluoropyrimidin-4-ylamino)bicyclo[2.2.1]heptane-2-carboxamide

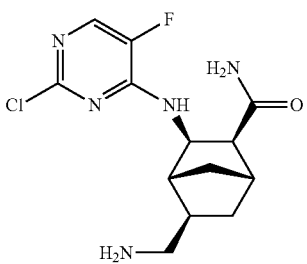 [SMILES: NC[C@@H]1C[C@@H]2C[C@H]1[C@@H](Nc1nc(Cl)ncc1F)[C@H]2C(N)=O]

To a stirring solution of (1S,2S,3R,4R)-3-[(2-chloro-5-fluoropyrimidin-4-yl)amino]-5-cyanobicyclo[2.2.1]heptane-2-carboxamide (0.98 g; 3.16 mmol) in tetrahydrofuran (15 ml) at 0° C., was added lithium 9-borabicyclo[3.3.1]nonan-9-uide (15.82 ml; 1.00 M in THF 15.82 mmol). At ten minutes, the reaction flask allowed to warm to room temperature and then heated to 66° C. for 1 hour. The reaction was quenched by slow addition of methanol. The mixture was concentrated en vacuo to a volume of ~10 mL, then silica powder (60 mesh) was added and the mixture dried overnight. The powder was then dry-loaded onto a silica column and subjected to flash chromatography, with a gradient of 1:1 chloroform:methanol with 1% triethylamine to afford desired product (0.297 mg, 30.1% yield). LC/MS [method B, retention time 0.59 min; m/z 314.3 (M+1)].

Example XX (1R,2S,3R,4R,5R)-3-(2-chloro-5-fluoropyrimidin-4-ylamino)-5-(2-(3-nitrophenyl)acetamido)methyl)bicyclo[2.2.1]heptane-2-carboxamide

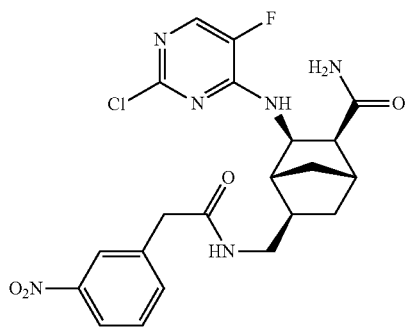

To a solution of 3-[tert-butoxycarbonyl)amino]benzoic acid (0.16 ml; 0.70 mmol) in DCM (5 ml), was added 1-chloro-N,N,2-trimethylprop-1-en-1-amine (592.81 mg; 0.59 mmol). The mixture was stirred for 1 hour at room temperature. The reaction mixture is concentrated en vacuo to afford crude acid chloride. It was used directly to the next step without further purification.

To a solution of (1R,2S,3R,4R)-5-(aminomethyl)-3-[(2-chloro-5-fluoropyrimidin-4-yl)amino]bicyclo[2.2.1]heptane-2-carboxamide (50.00 mg; 0.16 mmol) in DCM (2 ml), was added triethylamine (0.03 ml; 0.19 mmol) followed by the crude (3-nitrophenyl)acetyl chloride (0.70 ml; 0.25 M; 0.18 mmol). The reaction was stirred at room temperature for 16 hours. The reaction mixture was concentrated, and purified by flash chromatography using 0-100% ethyl acetate in hexane, followed by a 50% methanol-ethyl acetate flush to give 18.75 mg (24.7%) of pure product.

LC/MS [method B, retention time 5.2 min; m/z 477.3 (M+1)].

Synthesis of Macrocyclic Compounds

Example 1

(16Z)-4-fluoro-14,19-dioxa-2,6,8,26-tetraazatetracyclo[18.2.2.1~3,7~0.1~9,13~]hexacosa-3(26),4,6,9(25),10,12,16-heptaene

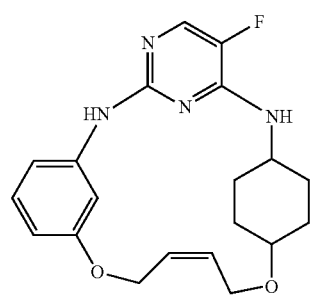 [SMILES: Fc1cnc2nc1NC1CCC(CC1)OC/C=C\COc1cccc(c1)N2]

To a solution of N$^4$-(4-(allyloxy)cyclohexyl)-N$^2$-(3-(allyloxy)phenyl)-5-fluoropyrimidine-2,4-diamine (100 mg, 0.25 mmol) in anhydrous dichloromethane was added a solution of Grubbs Catalyst, 2$^{nd}$ Generation (32 mg, 0.04 mmol) in anhydrous dichloromethane. The reaction mixture (total volume 125 mL) was heated to reflux for 3 d and then treated with Hoveyda-Grubbs Catalyst, 2$^{nd}$ Generation (23.6 mg, 0.0376 mmol). The reaction mixture was then heated to reflux for another 4 h. The reaction mixture was filtered and concentrated. The resulting residue was subjected to preparative, reverse-phase HPLC to separate the two major products, of which the faster-eluting compound was (16Z)-4-fluoro-14,19-dioxa-2,6,8,26-tetraazatetracyclo[18.2.2.1~3,7~0.1~9,13·]hexacosa-3(26),4,6,9(25),10,12,16-heptaene (white solid, 2.5 mg). LC/MS [method B, retention time 3.06 min; m/z 371.2 (M+1)].

Example 2

(16E)-4-fluoro-14,19-dioxa-2,6,8,26-tetraazatetracyclo[18.2.2.1~3,7~0.1~9,13·]hexacosa-3(26),4,6,9(25),10,12,16-heptaene

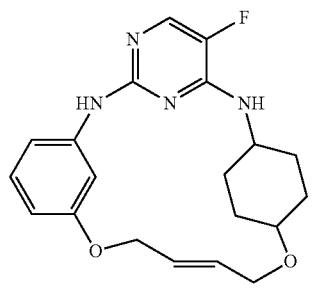 [SMILES: Fc1cnc2nc1NC1CCC(CC1)OC/C=C/COc1cccc(c1)N2]

Prepared by the same procedure used in Example 1 above. Preparative, reverse-phase HPLC separated the two major products, to afford (16E)-4-fluoro-14,19-dioxa-2,6,8,26-tetraazatetracyclo[18.2.2.1~3,7~0.1~9,13~]hexacosa-3(26),4,6,9(25),10,12,16-heptaene as the slower-eluting compound (white solid, 3 mg). LC/MS [method B, retention time 3.59 min; m/z 371.2 (M+1)].

Example 3

(15E,16aR,18S,19S,19aR)-3-fluoro-18-vinyl-14,16a,17,18,19,19a-hexahydro-1H,7H-6,2(azeno)-8,12-(metheno)cyclopenta[n][1,7,9,13]oxatriazacyclooctadecine-19-carboxamide

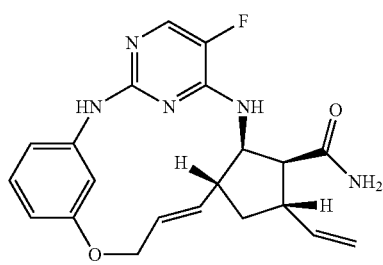 [SMILES: C=C[C@@H]1C[C@@H]2/C=C/COc3cccc(c3)Nc3ncc(F)c(n3)N[C@H]2[C@H]1C(N)=O]

To a stirred solution of (1S,2S,3R,4R)-3-(2-(3-(allyloxy)phenylamino)-5-fluoropyrimidin-4-ylamino)bicyclo[2.2.1]hept-5-ene-2-carboxamide (100 mg, 0.25 mmol) in anhydrous dichloromethane was added a solution of Grubbs catalyst, 2$^{nd}$ generation (32.2 mg, 0.04 mmol) in anhydrous dichloromethane. The reaction mixture (13 mL total volume) was then heated to reflux for 3 h under nitrogen, cooled, and concentrated under reduced pressure. The resultant residue was subjected to preparative reverse-phase (C-18) HPLC to separate the two major products, of which the faster eluting compound was (15E,16aR,18S,19S,19aR)-3-fluoro-18-vinyl-14,16a,17,18,19,19a-hexahydro-1H,7H-6,2-(azeno)-8,12-(metheno)cyclopenta[n][1,7,9,13]oxatriazacyclooctadecine-19-carboxamide (white solid, 15 mg). LC/MS [method A, retention time 4.04 min; m/z 396.2 (M+1)].

Example 4

(15Z,16aR,18S,19S,19aR)-3-fluoro-18-vinyl-14,16a,17,18,19,19a-hexahydro-1H,7H-6,2-(azeno)-8,12-(metheno)cyclopenta[n][1,7,9,13]oxatriazacyclooctadecine-19-carboxamide

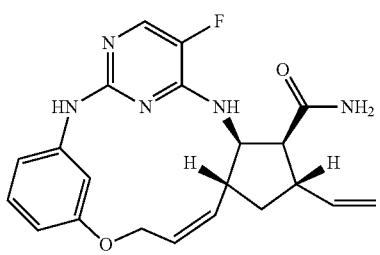 [SMILES: C=C[C@@H]1C[C@@H]2/C=C\COc3cccc(c3)Nc3ncc(F)c(n3)N[C@H]2[C@H]1C(N)=O]

Prepared by the same procedure used in Example 3 above. It was the slower-eluting of the two compounds afforded by preparative reverse-phase HPLC (15Z,16aR,18S,19S,19aR)-3-fluoro-18-vinyl-14,16a,17,18,19,19a-hexahydro-1H,7H-6,2-(azeno)-8,12-(metheno)cyclopenta[n][1,7,9,13]oxatriazacyclooctadecine-19-carboxamide was obtained as a grey solid (1.5 mg). LC/MS [method A, retention time 4.19 min m/z 396.2 (M+1)].

Example 5

(16aS,18R,19S,19aR)-18-ethyl-3-fluoro-14,15,16,16a,17,18,19,19a-octahydro-1H,7H-6,2-(azeno)-8,12-(metheno)cyclopenta[n][1,7,9,13]oxatriazacyclooctadecine-19-carboxamide

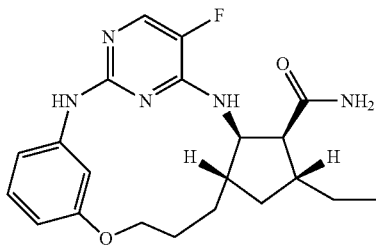 [SMILES: CC[C@@H]1C[C@@H]2CCCOc3cccc(c3)Nc3ncc(F)c(n3)N[C@H]2[C@H]1C(N)=O]

A mixture of the product compounds from Examples 3 and 4 (10 mg) was dissolved in methanol (5 mL) and then hydrogenated using an H-Cube Continuous-flow Hydrogenation Reactor equipped with catalyst 10% Pd/C cartridge. The reaction mixture was then concentrated under reduced pressure. The resultant residue was subjected to preparative, reverse-phase (C-18) HPLC to separate the two major products, of which the faster eluting product was (16aS,18R,19S,19aR)-18-ethyl-3-fluoro-14,15,16,16a,17,18,19,19a-octahydro-1H,7H-6,2-(azeno)-8,12-(metheno)cyclopenta[n][1,7,9,13]oxatriazacyclooctadecine-19-carboxamide (white solid, 1 mg). LC/MS [method A, retention time 4.54 min; m/z 400.3 (M+1)].

Example 6

(15Z,16aR,18R,19S,19aR)-18-ethyl-3-fluoro-14,16a,17,18,19,19a-hexahydro-1H,7H-6,2-(azeno)-8,12-(metheno)cyclopenta[n][1,7,9,13]oxatriazacyclooctadecine-19-carboxamide

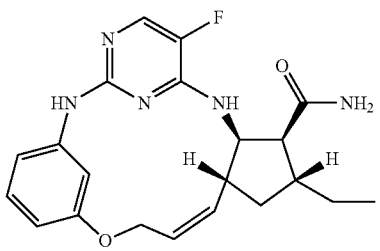 [SMILES: CC[C@@H]1C[C@@H]2/C=C\COc3cccc(c3)Nc3ncc(F)c(n3)N[C@H]2[C@H]1C(N)=O]

Prepared by the same procedure used to obtain the compound in preceding Example 5. It was the slower-eluting of the two compounds afforded by preparative reverse-phase HPLC. (15Z,16aR,18R,19S,19aR)-18-ethyl-3-fluoro-14,16a,17,18,19,19a-hexahydro-1H,7H-6,2-(azeno)-8,12-(metheno)cyclopenta[n][1,7,9,13]oxatriazacyclooctadecine-19-carboxamide was obtained as a white solid (1.7 mg). LC/MS [method A, retention time 4.63 min; m/z 398.3 (M+1)].

Example 7

(15R,16R,16aS,18R,19S,19aR)-18-(1,2-dihydroxyethyl)-3-fluoro-15,16-dihydroxy-14,15,16,16a,17,18,19,19a-octahydro-1H,7H-6,2-(azeno)-8,12-(metheno)cyclopenta[n][1,7,9,13]oxatriazacyclooctadecine-19-carboxamide

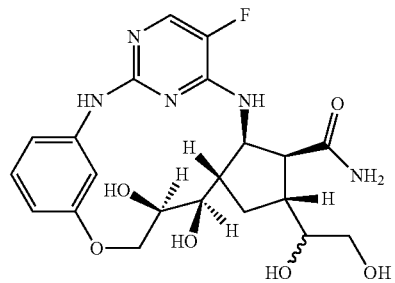 [SMILES: NC(=O)[C@@H]1[C@@H]2Nc3nc(ncc3F)Nc3cccc(c3)OC[C@@H](O)[C@H](O)[C@H]2C[C@H]1C(O)CO]

To a stirred suspension of the final product compound of Example 3 (10 mg, 0.03 mmol, 1 eq.) and 4-methylmorpholine-N-oxide (8.9 mg, 0.08 mmol) in acetone/water (4:1, 1 mL) at rt was added osmium tetroxide (0.19 mg, 0.007 mmol). The reaction mixture was stirred at rt for 2 h and then concentrated under reduced pressure. The residue was treated with saturated, aqueous sodium sulfite (1 mL) and then subjected to preparative HPLC to separate the mixture of products. (15R,16R,16aS,18R,19S,19aR)-18-(1,2-dihydroxyethyl)-3-fluoro-15,16-dihydroxy-14,15,16,16a,17,18,19,19a-octahydro-1H,7H-6,2-(azeno)-8,12-(metheno)cyclopenta[n][1,7,9,13]oxatriazacyclooctadecine-19-carboxamide was obtained (white solid, 1 mg) as the faster eluent. The stereochemistry of the hydroxyl groups was not determined. LC/MS [method B, retention time 1.01 min; m/z 464.5 (M+1)].

Example 8

(15S,16S,16aS,18R,19S,19aR)-18-(1,2-dihydroxy-ethyl)-3-fluoro-15,16-dihydroxy-14,15,16,16a,17,18,19,19a-octahydro-1H,7H-6,2-(azeno)-8,12-(metheno)cyclopenta[n][1,7,9,13]oxatriazacyclooctadecine-19-carboxamide

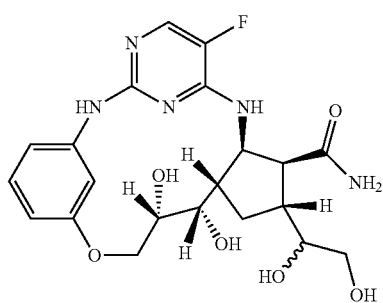 [SMILES: NC(=O)[C@@H]1[C@@H]2Nc3nc(ncc3F)Nc3cccc(c3)OC[C@H](O)[C@@H](O)[C@H]2C[C@H]1C(O)CO]

Prepared by the same procedure used to obtain the final product compound of Example 7. After preparative HPLC, (15S,16S,16aS,18R,19S,19aR)-18-(1,2-dihydroxyethyl)-3-fluoro-15,16-dihydroxy-14,15,16,16a,17,18,19,19a-octahydro-1H,7H-6,2-(azeno)-8,12-(metheno)cyclopenta[n][1,7,9,13]oxatriazacyclooctadecine-19-carboxamide was obtained (off-white solid, 1 mg) as the slower eluent. The stereochemistry of the hydroxyl groups was not determined. LC/MS [method B, retention time 1.20 min; m/z 464.5 (M+1)].

Example 9

(15RS,16SR,16aS,18R,19S,19aR)-18-ethyl-3-fluoro-15,16-dihydroxy-14,15,16,16a,17,18,19,19a-octahydro-1H,7H-6,2-(azeno)-8,12-(metheno)cyclopenta[n]1[1,7,9,13]oxatriazacyclooctadecine-19-carboxamide

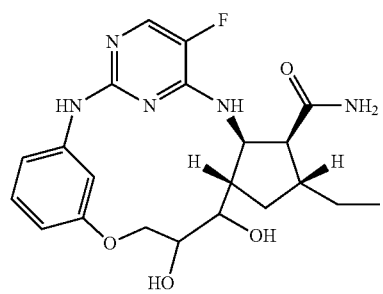 [SMILES: CC[C@@H]1C[C@@H]2C(O)C(O)COc3cccc(c3)Nc3ncc(F)c(n3)N[C@H]2[C@H]1C(N)=O]

To a stirred suspension of the final product compound of Example 6 (5 mg, 0.01 mmol) and 4-methylmorpholine-N-oxide (4.42 mg, 0.04 mmol) in acetone/water (4:1, 0.5 mL) at rt was added osmium tetroxide (0.10 mg, 0.0003 mmol). The reaction mixture was stirred at rt overnight, quenched by the addition of aqueous, saturated sodium sulfite solution (1 mL), filtered, and concentrated. The resulting residue was preparative, reverse-phase HPLC to afford (15RS,16SR,16aS,18R,19S,19aR)-18-ethyl-3-fluoro-15,16-dihydroxy-14,15,16,16a,17,18,19,19a-octahydro-1H,7H-6,2-(azeno)-8,12-(metheno)cyclopenta[n][1,7,9,13]oxatriazacyclooctadecine-19-carboxamide off-white solid, 1 mg). LC/MS [method A, retention time 4.16 min; m/z 432.2 (M+1)].

Example 10

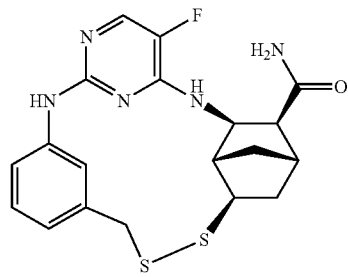 [SMILES: NC(=O)[C@H]1[C@H]2C[C@H]3[C@H]1Nc1nc(ncc1F)Nc1cccc(c1)CSS[C@@H]3C2]

To a solution of Thioacetic acid S-{3-[4-((1S,2S,3S,4S,6R)-6-acetylsulfanyl-3-carbamoyl-bicyclo[2.2.1]hept-2-ylamino)-5-fluoro-pyrimidin-2-ylamino]-benzyl}ester (30 mg, 0.06 mmol) in MeOH (300 mL) was added MeONa/MeOH (30%, 0.1 mL). The mixture was stirred at rt with solution opened to air (no cap) overnight. The mixture was concentrated and purified by flash chromatography to afford the final product (24 mg). LC/MS [method A, retention time, 5.01 min; m/z 418.1 (M+1)].

Example 11

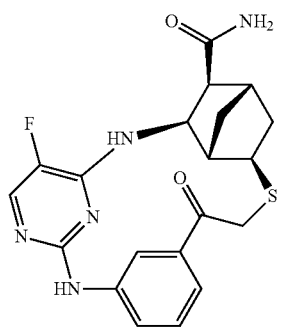 [SMILES: NC(=O)[C@H]1[C@H]2C[C@H]3[C@H]1Nc1nc(ncc1F)Nc1cccc(c1)C(=O)CS[C@@H]3C2]

To a pressure vessel charged with a solution of preparative Example XV(50 mg, 0.10 mmol) in ethanol (1.2 mL) was added ammonium chloride (55.7 mg, 1.04 mmol), water (0.6 mL) and indium (49.1 mg, 0.43 mmol). The pressure vessel was sealed and heated at 100° C. for 1 h. The reaction mixture was then diluted with ethyl acetate and the phases were separated with an Alltech phase separator column. The organic phase was concentrated under reduced pressure to afford crude (1S,2S,3S,4S,5R)-5-(2-(3-aminophenyl)-2-oxoethylthio)-3-(2-chloro-5-fluoropyrimidin-4-ylamino)bicyclo[2.2.1]heptane-2-carboxamide, which was used without further manipulation.

In a 3-neck flask, a solution of TFA (10.3 μL, 0.14 mmol) and anhydrous acetonitrile (20 mL) was heated to reflux. Via a dropping funnel, to the TFA solution was then added dropwise over 1 h a solution of crude (1S,2S,3S,4S,5R)-5-(2-(3-aminophenyl)-2-oxoethylthio)-3-(2-chloro-5-fluoropyrimidin-4-ylamino)bicyclo[2.2.1]heptane-2-carboxamide (25 mg, 0.06 mmol) in acetonitrile/isopropanol (1:1, 10 mL). The reaction mixture was then heated to reflux overnight. The reaction mixture was cooled, concentrated under reduced pressure, and the resultant residue was subjected to flash chromatography on silica gel to afford the final product compound (11 mg). LC/MS [method A, retention time 3.94 min; m/z 414.2 (M+1)].

Example 12

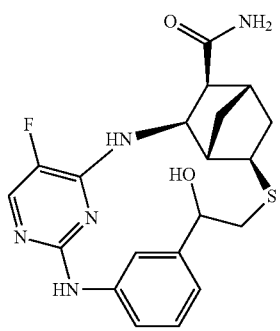 [SMILES: NC(=O)[C@H]1[C@H]2C[C@H]3[C@H]1Nc1nc(ncc1F)Nc1cccc(c1)C(O)CS[C@@H]3C2]

A mixture of the final product compound from preceding Example 11 (60 mg, 0.15 mmol) and sodium borohydride (22 mg, 0.58 mmol) in THF/ethanol (1:1, 2 mL) was stirred at rt for 4 h. The reaction mixture was subjected to prep HPLC to afford product (white solid, 3 mg). LC/MS [method A, retention time 3.54 min; m/z 416.2 (M+1)].

Example 13

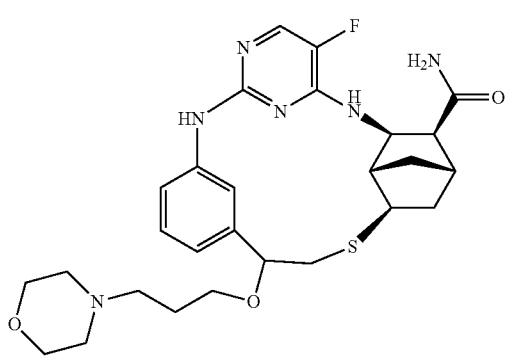 [SMILES: NC(=O)[C@H]1[C@H]2C[C@H]3[C@H]1Nc1nc(ncc1F)Nc1cccc(c1)C(OCCCN1CCOCC1)CS[C@@H]3C2]

To a solution of the final product compound of the preceding Example 12 (50 mg, 0.12 mmol) in DMSO (0.5 mL)) was added NaH (60%, 26 mg, 0.66 mmol)). The mixture was stirred for 30 min under nitrogen at rt. 4-(3-chloropropyl) morpholine hydrochloride (48 mg, 0.24 mmol)) was added into the mixture, The reaction was allowed to proceed overnight at rt. The mixture was quenched with MeOH and neutralized with AcOH. It was then apply to Prep HPLC to afford pure adduct (7 mg). LC/MS [method B, retention time 2.50 min; m/z 543.7 (M+1)].

Example 14

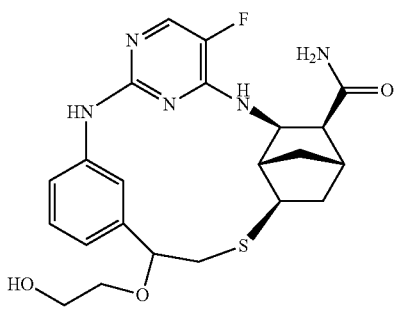 [SMILES: NC(=O)[C@H]1[C@H]2C[C@H]3[C@H]1Nc1nc(ncc1F)Nc1cccc(c1)C(OCCO)CS[C@@H]3C2]

The title compound was prepared using the procedure in preceding Example 13. Except for this reaction the reaction time was 3 hours. LC/MS [method A, retention time 3.97 min; m/z 460.3 (M+1)].

Example 15

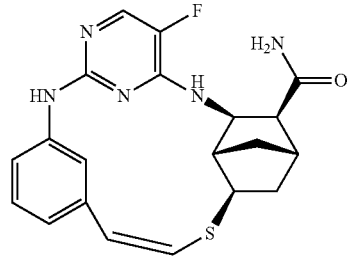 [SMILES: NC(=O)[C@H]1[C@H]2C[C@H]3[C@H]1Nc1nc(ncc1F)Nc1cccc(c1)/C=C\S[C@@H]3C2]

To a solution of preceding final product compound Example 11 (80 mg, 0.19 mmol) in pyr-DCM (1:1, 2 mL) at 0° C., was added TfCl (82 L, 0.77 mmol) dropwise. The mixture was allowed to warm to rt and stirred overnight. The mixture was concentrated and neutralized with AcOH. It was then applied to a C-18 prep HPLC to obtain pure adduct (1 mg). LC/MS [method B, retention time 1.24 min; m/z 398.1 (M+1)].

Example 16

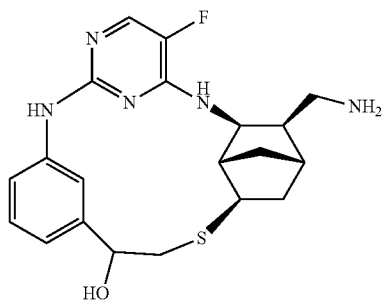 [SMILES: NC[C@H]1[C@H]2C[C@H]3[C@H]1Nc1nc(ncc1F)Nc1cccc(c1)C(O)CS[C@@H]3C2]

The final product compound from preceding Example 11 (400 mg, 0.97 mmol) was suspended in THF (5 mL) at 0° C. liquid LiAlH$_4$ (1 M in THF, 3.87 mL) was added to the stirring mixture dropwise under nitrogen. The mixture was allowed to warm to rt. After 5 h, the reaction was quenched with MeOH. About 20% volume of the mixture was neutralized with AcOH and then applied to a C-18 prep HPLC to afford pure adduct (40 mg). LC/MS [method A, retention time 0.32 min; m/z 402.3 (M+1)]

Example 17

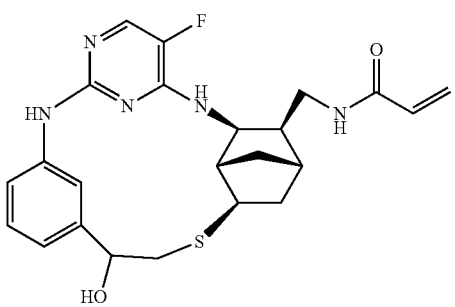 [SMILES: C=CC(=O)NC[C@H]1[C@H]2C[C@H]3[C@H]1Nc1nc(ncc1F)Nc1cccc(c1)C(O)CS[C@@H]3C2]

To a solution of the final product compound from Example 16 (30 mg, 0.07 mmol) and acrylic acid (7 mg, 0.1 mmol) in DMF (1 mL), were added N-[3-(dimethylamino)propyl]-N'- ethylcarbodiimide hydrochloride (18.6 mg, 0.1 mmol), 1H-1,2,3-benzotriazol-1-ol (13 mg, 0.1 mmol) and Et₃N (28 L, 0.17 mmol). The mixture was stirred at rt overnight. The mixture was then applied to C-18 prep HPLC to afford pure adduct (3 mg). LC/MS [method A, retention time 3.71 min; m/z 456.4 (M+1)].

Example 18

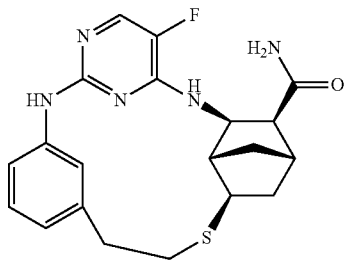 [SMILES: NC(=O)[C@H]1[C@H]2C[C@H]3[C@H]1Nc1nc(ncc1F)Nc1cccc(c1)CCS[C@@H]3C2]

2-(3-nitrophenyl)ethanol (1 g, 6.0 mmol) and tosyl chloride (1.37 g, 7.2 mmol) were stirred in pyridine-DCM (1:1, 10 mL) at rt overnight. The mixture was diluted with DCM and washed with 10% HCl, saturated NaHCO₃ solution, H₂O, brine and dried over Na₂SO₄. The organic layer was concentrated and dried to afford crude 2-(3-nitrophenyl)ethyl 4-methylbenzenesulfonate It was used directly for the next step without further purification.

To a suspension of S-{(1S,2R,4S,5S,6S)-5-(aminocarbonyl)-6-[(2-chloro-5-fluoropyrimidin-4-yl)amino]bicyclo[2.2.1]hept-2-yl}ethanethioate (300 mg, 0.84 mmol) in anhydrous methanol (5 mL) was added sodium methoxide solution (0.3 mL, ~30% in methanol) and the resulting mixture was stirred at rt for 30 min. The reaction mixture was then treated crude 2-(3-nitrophenyl)ethyl 4-methylbenzenesulfonate (537 mg, 1.7 mmol) and stirring at rt overnight. The reaction mixture was diluted with methanol, neutralized by the addition of strongly acid cation-exchange resin (hydrogen form), filtered, and then concentrated under reduced pressure. The resultant residue was subjected to flash chromatography on silica gel to afford (1S,2S,3S,4S,5R)-3-[(2-chloro-5-fluoropyrimidin-4-yl)amino]-5-{[2-(3-nitrophenyl)ethyl]thio}bicyclo[2.2.1]heptane (245 mg).

To a suspension of (1S,2S,3S,4S,5R)-3- [(2-chloro-5-fluoropyrimidin-4-yl)amino]-5-{[2-(3-nitrophenyl)ethyl]thio}bicyclo[2.2.1]heptane (243 mg, 0.5 mmol) in EtOH (7 mL), was added NH₄Cl (268 mg, 5.0 mmol) and water (3.5 mL). The mixture was heated at 100 C until completion (1 h). The mixture was filtered, concentrated, and dried. The resulting crude product 1S,2S,3S,4S,5R)-5-{[2-(3-aminophenyl)ethyl]thio}-3-[(2-chloro-5-fluoropyrimidin-4-yl)-amino]bicyclo[2.2.1]heptane-2-carboxamide was used directly in next step without further purification.

To a 500 mL round-bottom flask, was charged with TFA (29 L) and 100 mL dry ACN. It was then reflux under heat. Solution of (1S,2S,3S,4S,5R)-5-{[2-(3-aminophenyl)ethyl]thio}-3-[(2-chloro-5-fluoropyrimidin-4-yl)amino]bicyclo[2.2.1]heptane-2-carboxamide (100.00 mg; 0.16 mmol) in 1/1 ACN/iPrOH (15 mL) was added dropwise with a syringe pump over 3 h. The mixture was refluxed overnight. It was cooled and concentrated. The resulting residue was applied to a reverse-phase prep HPLC to obtain pure compound of example 18 (10 mg). LC/MS [method A, retention time 4.58 min; m/z 400.1 (M+1)].

Example 19

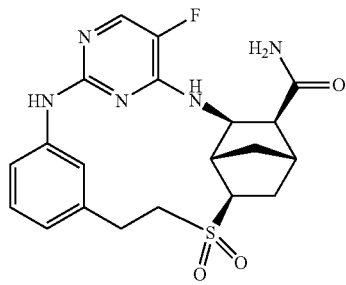 [SMILES: NC(=O)[C@H]1[C@H]2C[C@H]3[C@H]1Nc1nc(ncc1F)Nc1cccc(c1)CCS(=O)(=O)[C@@H]3C2]

To a solution of the final product compound from preceding Example 18 (50 mg, 0.12 mmol) in DCM at rt under nitrogen, was added MCPBA (70%, 37 mg, 0.14 mmol). The mixture was stirred rt for 4 hours. The reaction was quenched with saturated NaHSO₃ solution and the mixture was concentrated. The resulting residue was applied to the reverse-phase prep HPLC to afford the desired adduct (3 mg).

LC/MS [method A, retention time 3.28 min; m/z 432.1 (M+1)].

Example 20

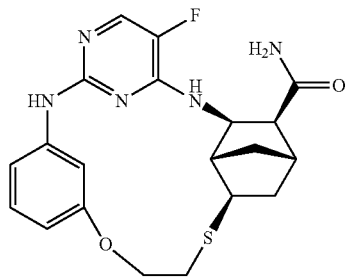 [SMILES: NC(=O)[C@H]1[C@H]2C[C@H]3[C@H]1Nc1nc(ncc1F)Nc1cccc(c1)OCCS[C@@H]3C2]

To a solution of N-(3-hydroxyphenyl)acetamide (1 g, 6.6 mmol) in DMF (10 mL) was added NaH (60%, 0.24 g, 9.9 mol) under nitrogen. After 30 min, solid ethane-1,2-diyl bis (4-methylbenzenesulfonate) (7.4 g, 19.9 mmol) was added to mixture. The reaction was allowed to proceed overnight. The mixture was diluted with ethyl acetate (5 mL), and was poured into 150 mL water. The crude product 2-[3-(acetylamino)phenoxy]ethyl 4-methylbenzenesulfonate was obtained by vacuum filtration and dried. The adduct was carried to next step directly without further manipulation.

(1S,2S,3S,4S,5R)-5-({2-[3-(acetylamino)phenoxy]ethyl}thio)-3-[(2-chloro-5-fluoropyrimidin-4-yl)amino]bicyclo[2.2.1]heptane-2-carboxamide was prepared as described in the synthesis of the final product compound in preceding Example 18 above. To a 100 mL round-bottom flask, was charged with TFA (22 L) and 50 mL dry ACN. It was then reflux under heat. Solution of ((1S,2S,3S,4S,5R)-5-({2-[3-(acetylamino)phenoxy]ethyl}thio)-3-[(2-chloro-5-fluoropyrimidin-4-yl)-amino]bicyclo[2.2.1]heptane-2-carboxamide (50 mg; 0.10 mmol) in 1/1 ACN/iPrOH (10 mL) was added dropwise with a syringe pump over 3 h. The mixture was refluxed overnight. HCl (4 M in dioxane, 1 mL) was added t the refluxing mixture and stirred overnight. The mixture was cooled and concentrated. The resulting residue was applied to a reverse-phase prep HPLC to obtain pure compound of Example 20 (9 mg) and also Example 21 (10 mg). LC/MS [method A, retention time 4.56 min; m/z 416.1 (M+1)].

Example 21

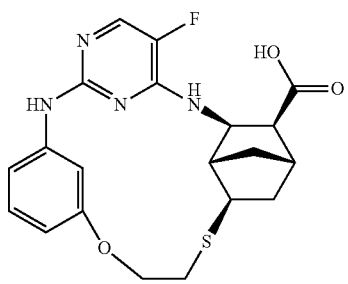 [SMILES: O=C(O)[C@H]1[C@H]2C[C@H]3[C@H]1Nc1nc(ncc1F)Nc1cccc(c1)OCCS[C@@H]3C2]

This compound was prepared as described above in Example 20. LC/MS [method A, retention time 4.87 min; m/z 417.1 (M+1)].

Example 22

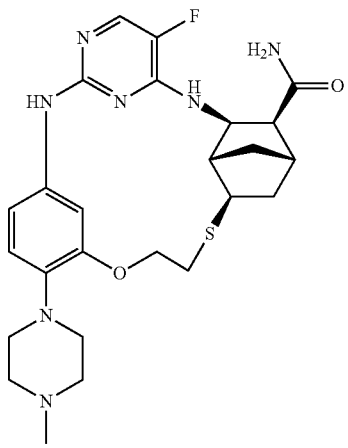 [SMILES: CN1CCN(c2ccc3cc2OCCS[C@@H]2C[C@@H]4C[C@H]2[C@@H](Nc2nc(ncc2F)N3)[C@H]4C(N)=O)CC1]

(1S,2S,3S,4S,5R)-5-({2-[5-amino-2-(4-methylpiperazin-1-yl)phenoxy]ethyl}thio)-3-[(2-chloro-5-fluoropyrimidin-4-yl)amino]bicyclo[2.2.1]heptane-2-carboxamide was prepared as described in the synthesis in Example 20 above.

The macrocylisation step was similar to the synthesis of the final product compound in Example 20 above to give this new compound (6 mg). LC/MS [method A, retention time 3.50 min; m/z 514.3 (M+1)].

Example 23

(1S,2S,3S,4S,5R)-3-[(2-chloro-5-fluoropyrimidin-4-yl)amino]-5-[(2-{[2-(4-methylpiperazin-1-yl)-5-nitrophenyl]amino}-2-oxoethyl)thio]bicyclo[2.2.1]heptane-2-carboxamide

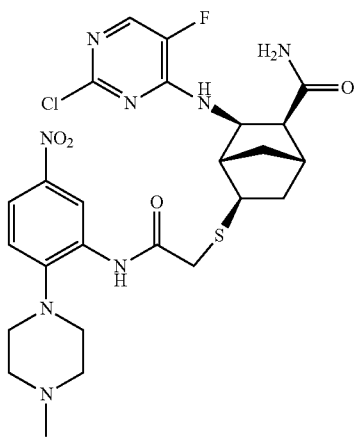 [SMILES: CN1CCN(c2ccc([N+](=O)[O-])cc2NC(=O)CS[C@@H]2C[C@@H]3C[C@H]2[C@@H](Nc2nc(Cl)ncc2F)[C@H]3C(N)=O)CC1]

Bromoacetyl bromide (80.87 µl; 0.93 mmol) was dissolved in dry DCM (2 mL) and it was cooled to 0° C. Triethyl amine (141.58 µl; 1.02 mmol) was added into the reaction mixture, followed by addition of 2-(4-methylpiperazin-1-yl)-5-nitroaniline (200.00 mg; 0.85 mmol) (dissolved in 2 mL DMF). The mixture was stirred at 0° C. for 1 h and allowed to warm to rt for 2 h. The mixture was concentrated and dried to afford crude 2-bromo-N-[2-(4-methylpiperazin-1-yl)-5-nitrophenyl]acetamide. The adduct was proceed to next step without further purification.

The title compound was prepared in the similar procedure as described in the preceding Example 18 LC/MS [method A, retention time 3.55 min; m/z 593.1 (M+1)].

Example 24

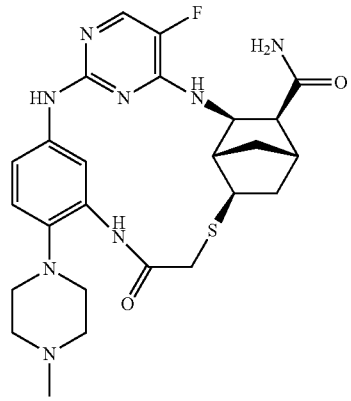 [SMILES: CN1CCN(c2ccc3cc2NC(=O)CS[C@@H]2C[C@@H]4C[C@H]2[C@@H](Nc2nc(ncc2F)N3)[C@H]4C(N)=O)CC1]

This compound was prepared in the similar procedure as described in the preceding Example 18. LC/MS [method A, retention time 0.60 min; m/z 527.2 (M+1)].

Example 25

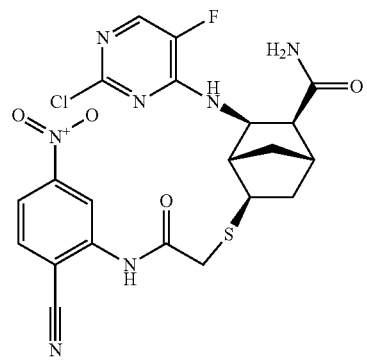

This compound was prepared in the similar procedure as described in the preceding Example 25. LC/MS [method A, retention time 4.60 min; m/z 519.9 (M+1)].

Example 26

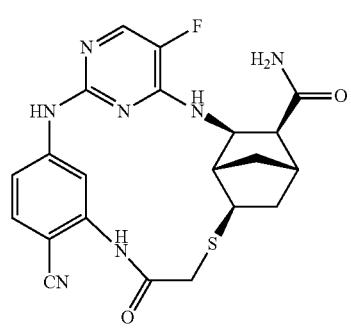 [SMILES: N#Cc1ccc2cc1NC(=O)CS[C@@H]1C[C@@H]3C[C@H]1[C@@H](Nc1nc(ncc1F)N2)[C@H]3C(N)=O]

This compound was prepared in the similar procedure as described in the preceding Example 25. LC/MS [method A, retention time 4.07 min; m/z 454.2 (M+1)].

Example 27

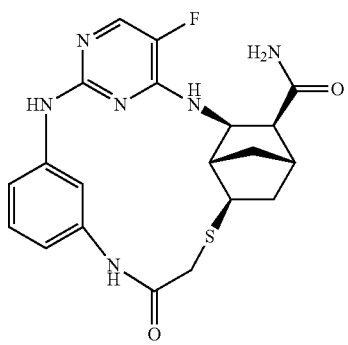 [SMILES: NC(=O)[C@H]1[C@H]2C[C@H]3[C@H]1Nc1nc(ncc1F)Nc1cccc(c1)NC(=O)CS[C@@H]3C2]

This compound was prepared in the similar procedure as described in the preceding Example 25. LC/MS [method A, retention time 3.65 min; m/z 429.1 (M+1)].

Example 28

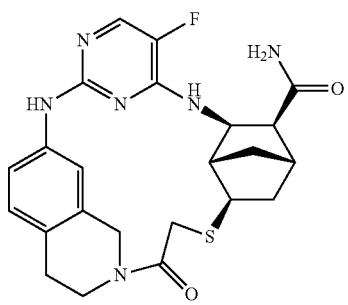 [SMILES: NC(=O)[C@H]1[C@H]2C[C@H]3[C@H]1Nc1nc(ncc1F)Nc1ccc4c(c1)CN(CC4)C(=O)CS[C@@H]3C2]

This compound was prepared in the similar procedure as described in the preceding Example 25. LC/MS [method B, retention time 3.71 min; m/z 469.4 (M+1)].

Example 29

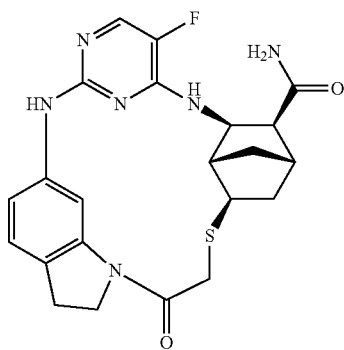 [SMILES: NC(=O)[C@H]1[C@H]2C[C@H]3[C@H]1Nc1nc(ncc1F)Nc1ccc4c(c1)N(CC4)C(=O)CS[C@@H]3C2]

This compound was prepared in the similar procedure as described in the preceding Example 25. LC/MS [method A, retention time 3.82 min; m/z 455.2 (M+1)].

Example 30

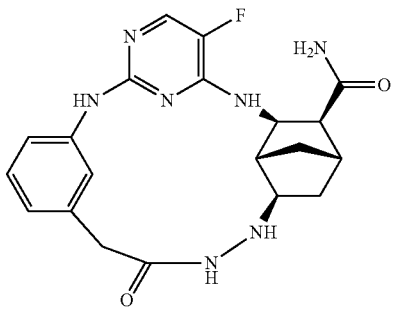 [SMILES: NC(=O)[C@H]1[C@H]2C[C@H]3[C@H]1Nc1nc(ncc1F)Nc1cccc(c1)CC(=O)NN[C@@H]3C2]

Using the similar procedure described in *J. Am. Chem. Soc.* 2006, 128, 11693-11712, A mixture of di-tert-butyl 1-{(2R,5S,6R)-5-(aminocarbonyl)-6-[(2-chloro-5-fluoropyrimidin-4-yl)amino]bicyclo[2.2.1]hept-2-yl}hydrazine-1,2-dicarboxylate and it isomer di-tert-butyl 1-{(2S,5R,6S)-6-(aminocarbonyl)-5-[(2-chloro-5-fluoropyrimidin-4-yl)amino]bicyclo[2.2.1]hept-2-yl}hydrazine-1,2-dicarboxylate was prepared. In detail, Mn(dpm)$_3$ (6.05 mg; 0.01 mmol) was dissolved in iPrOH (2.50 ml) at rt under nitrogen. The dark brown solution was chilled to 0° C. in an ice bath. To the chilled solution was added (2S,3R)-3-[(2-chloro-5-fluoropyrimidin-4-yl)amino]bicyclo[2.2.1]hept-5-ene-2-carboxamide (141.35 mg; 0.50 mmol), di-tert-butyl (E)-diazene-1,2-dicarboxylate (172.70 mg; 0.75 mmol) and phenylsilane (0.06 ml; 0.50 mmol) in one portion. The resulting suspension was stirred at 0° C. for 30 minutes, then allowed to warm to rt. The reaction was allowed to proceed for 5 h. The reaction was quenched with water (1 mL). Brine (5 mL) was then added and the reaction mixture extracted with EtOAc (3x~10 mL). The combined organic layers were dried over magnesium sulfate, filtered and concentrated to give a light orange residue. The residue was applied to a normal phase chromatography to afford the desired product (97 mg) and its regioisomer (160 mg).

A microwave tube equipped with a stir bar was charged with di-tert-butyl 1-{(2S,5R,6S)-6-(aminocarbonyl)-5-[(2-chloro-5-fluoropyrimidin-4-yl)-amino]bicyclo[2.2.1]hept-2-yl}hydrazine-1,2-dicarboxylate (113.00 mg; 0.22 mmol) and (3-aminophenyl)acetic acid (33.17 mg; 0.22 mmol) in dry iPrOH (2.00 ml). The vial was sealed, and trifluoroacetic acid (0.04 ml; 0.55 mmol; 2.50 eq.) was then added via syringe. The mixture was stirred at rt for 5 h, One more equivalent of TFA was added, and the reaction was refluxed overnight. The mixture was concentrated and applied to a reverse-phase prep HPLC to afford desired macrocylic adduct (4 mg). LC/MS [method A, retention time 0.37 min; m/z 412.2 (M+1)].

Example 31

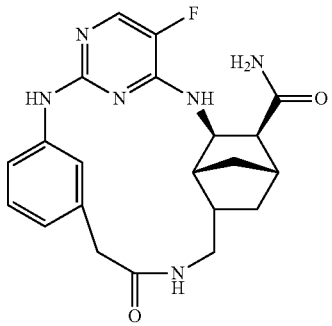 [SMILES: NC(=O)[C@H]1[C@@H]2CC3CNC(=O)Cc4cccc(c4)Nc4ncc(F)c(n4)N[C@@H]1[C@@H]3C2]

To a stirring solution of (1R,2S,3R,4R)-3-[(2-chloro-5-fluoropyrimidin-4-yl)amino]-5-({[(3-nitrophenyl)acetyl]amino}methyl)bicyclo[2.2.1]heptane-2-carboxamide (18.75 mg; 0.04 mmol) in ethanol (10 mL), was added. To this ammonium chloride (21.03 mg; 0.39 mmol), indium metal (18.51 mg; 0.16 mmol) and water (5 mL). The mixture was heated to reflux for 4 hours, then the temperature lowered to 70° C. for an additional 12 hours. The reaction was allowed to cool to room temperature, then filtered through a water-absorbing column, and finally concentrated to afford the crude (1R,2S,3R,4R)-5-(2-(3-aminophenyl)acetamidomethyl)-3-(2-chloro-5-fluoropyrimidin-4-ylamino)bicyclo[2.2.1]heptane-2-carboxamide.

The ring-closing step was performed as described for the synthesis of the final product compound in preceding Example 25 to afford this desired macrocycle (1 mg, 7%). LC/MS [method B, retention time 1.6 min; m/z 411.3 (M+1)].

Example 32

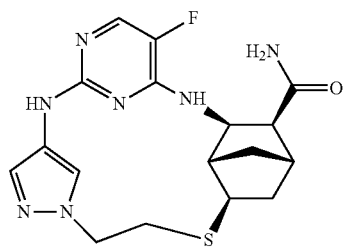 [SMILES: NC(=O)[C@H]1[C@H]2C[C@H]3[C@H]1Nc1nc(ncc1F)Nc1cnn(c1)CCS[C@@H]3C2]

This final product compound was prepared using a procedure similar to that used in Example 22 that in the preceding final product compound of Example ???. LC/MS [method A, retention time 3.6 min; m/z 390.2 (M+1)].

Example 33

(16Z)-6-fluoro-14,19-dioxa-2,4,8,26-tetraazatetracyclo[18.3.1.1~3,7~0.1~9,13~]hexacosa-1(24),3(26),4,6,16,20,22-heptaene

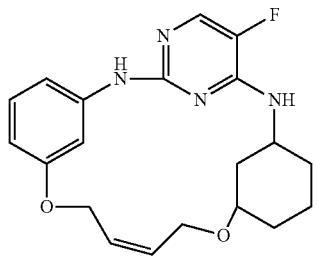 [SMILES: Fc1cnc2nc1NC1CCCC(C1)OC/C=C\COc1cccc(c1)N2]

To a solution of N*4*-(3-Allyloxy-cyclohexyl)-N*2*-(3-allyloxy-phenyl)-5-fluoro-pyrimidine-2,4-diamine (70 mg, 0.18 mmol) in anhydrous dichloromethane was added a solution of Grubbs Catalyst, 2$^{nd}$ Generation (22 mg, 0.03 mmol) in anhydrous dichloromethane (90 mL). The reaction was heated to reflux overnight. The reaction mixture was filtered and concentrated. The resulting residue was subjected to preparative, reverse-phase HPLC to separate the two major products, of which the slower eluting compound was (16Z)-6-fluoro-14,19-dioxa-2,4,8,26-tetraazatetracyclo[18.3.1.1~3,7~0.1~9,13~]hexacosa-1(24),3(26),4,6,16,20,22-heptaene (white solid, 1 mg). LC/MS [method B, retention time 5.15 min; m/z 371.4 (M+1)].

Example 34

6-fluoro-14,19-dioxa-2,4,8,26-tetraazatetracyclo[18.3.1.1~3,7~0.1~9, 13~]hexacosa-1(24),3(26),4,6,16,20,22-heptaene

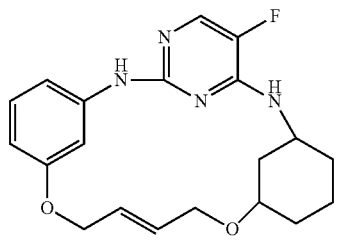 [SMILES: Fc1cnc2nc1NC1CCCC(C1)OC/C=C/COc1cccc(c1)N2]

Prepared by the same procedure used for Example 33. Preparative, reverse-phase HPLC separated the two major products, to afford 6-fluoro-14,19-dioxa-2,4,8,26-tetraazatetracyclo[18.3.1.1~3,7~0.1~9,13~]hexacosa-1(24),3(26),4,6,16,20,22-heptaene as the faster eluting compound (white solid, 1 mg).
LC/MS [method B, retention time 4.70 min; m/z 371.4 (M+1)].

Example 35

6-fluoro-14,19-dioxa-2,4,8,26-tetraazatetracyclo[18.3.1.1~3,7~0.1~9,13~]hexacosa-1(24),3(26),4,6,20,22-hexaene

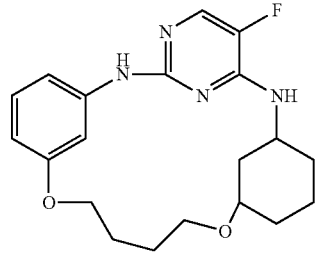

To a solution of 6-fluoro-14,19-dioxa-2,4,8,26-tetraazatetracyclo[18.3.1.1~3,7~0.1~9,13~]hexacosa-1(24),3(26),4,6,20,22-hexaene (10 mg, 0.03 mmol) in EtOH (2 mL) was charged with Pd/C (5 mg). The mixture was stirred at rt under hydrogen (1 atm). After 1 h, the mixture was filtered and applied to a reverse-phase prep HPLC to afford desired product (1 mg). LC/MS [method A, retention time 4.31 min; m/z 373.3 (M+1)].

Example 36

(16R,17S)-6-fluoro-14,19-dioxa-2,4,8,26-tetraazatetracyclo[18.3.1.1~3,7~0.1~9,13~]hexacosa-1(24),3(26),4,6,20,22-hexaene-16,17-diol

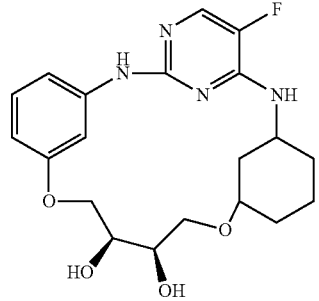 [SMILES: O[C@@H]1COC2CCCC(C2)Nc2nc(ncc2F)Nc2cccc(c2)OC[C@@H]1O]

To a suspension of (16R,17S)-6-fluoro-14,19-dioxa-2,4,8,26-tetraazatetracyclo[18.3.1.1~3,7~0.1~9,13~]hexacosa-1(24),3(26),4,6,20,22-hexaene-16,17-diol (15 mg, 0.04 mol)

and 4-methyl morphpline-N-oxide (14 mg, 0.12 mmol) in acetone/water (4:1, 1 mL), was added osmium tetraoxide (0.31 mg, 1.2 mol). The mixture was stirred for 2 h. It was then filtered and applied to a reverse-phase prep HPLC to obtain two adducts (this compound and that in Example 37 below). The stereochemistry of the hydroxyl groups was not determined. They are tentatively assigned as drew in the schemes. LC/MS [method A, retention time 3.33 min; m/z 405.3 (M+1)].

Example 37

6-fluoro-14,19-dioxa-2,4,8,26-tetraazatetracyclo [18.3.1.1~3,7~0.1~9,13~]hexacosa-1(24),3(26),4,6, 16,20,22-heptaene

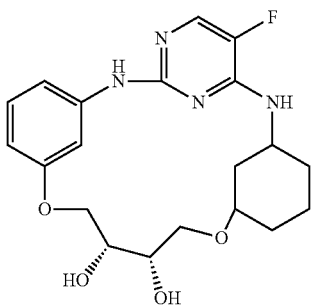 [SMILES: O[C@@H]1COc2cccc(c2)Nc2ncc(F)c(n2)NC2CCCC(C2)OC[C@@H]1O]

The synthesis was described in Example 36 above. The stereochemistry of the hydroxyl groups was not determined. They are tentatively assigned as drew in the schemes. LC/MS [method A, retention time 3.83 min; m/z 405.3 (M+1)].

Example 38

(16Z)-4-fluoro-14,19-dioxa-2,6,8,26-tetraazatetracyclo[18.2.2.1~3,7~0.1~9,13~]hexacosa-3(26),4,6,9 (25),10,12,16-heptaene

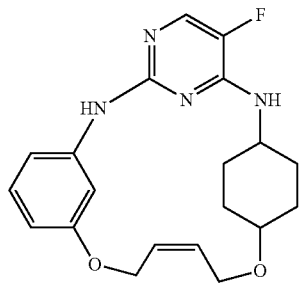 [SMILES: Fc1cnc2nc1NC1CCC(CC1)OC/C=C\COc1cccc(c1)N2]

To a solution of $N^4$-(4-(allyloxy)cyclohexyl)-$N^2$-(3-(allyloxy)phenyl)-5-fluoropyrimidine-2,4-diamine as provided in Preparative Example 11 (100 mg, 0.25 mmol) in anhydrous dichloromethane was added a solution of Grubbs Catalyst, $2^{nd}$ Generation (32 mg, 0.04 mmol) in anhydrous dichloromethane. The reaction mixture (total volume 125 mL) was heated to reflux for 3 d and then treated with Hoveyda-Grubbs Catalyst, $2^{nd}$ Generation (23.6 mg, 0.0376 mmol). The reaction mixture was then heated to reflux for another 4 h. The reaction mixture was filtered and concentrated. The resulting residue was subjected to preparative, reverse-phase HPLC to separate the two major products, of which the faster-eluting compound was (16Z)-4-fluoro-14,19-dioxa-2,6,8,26-tetraazatetracyclo[18.2.2.1~3,7~0.1~9,13~]hexacosa-3(26),4, 6,9(25),10,12,16-heptaene (white solid, 2.5 mg). LC/MS [method B, retention time 3.06 min; m/z 371.2 (M+1)].

Further Macrocyclic Compounds and Synthesis Intermediates

Example 39

(1R,2S,3R,4R,5R)-5-((2-(3-aminophenyl)acetamido) methyl)-3-(2-chloro-5-fluoro-pyrimidin-4-ylamino) bicyclo[2.2.1]heptane-2-carboxamide

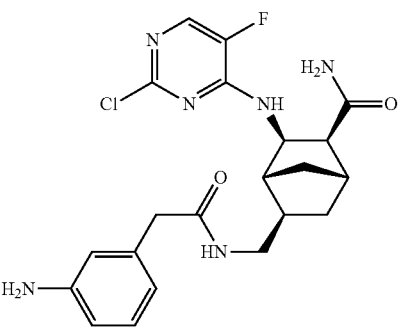

The nitro group reduction step was performed as described for Procedure A with (1S,2S,3S,4S,5R)-3-[(2-chloro-5-fluoropyrimidin-4-yl)amino]-5-({2-[(3-nitro-phenyl)amino]-2-oxoethyl}thio)bicyclo[2.2.1]heptane-2-carboxamide (18.75 mg; 0.04 mmol) to afford desired aniline (15 mg, 85%). LC/MS [method B, retention time 2.8 min; m/z 447.0 (M+1)].

Tert-butyl 3-(((1R,4R,5S,6R)-5-carbamoyl-6-(2-chloro-5-fluoropyrimidin-4-yl-amino)bicyclo[2.2.1] heptan-2-yl)methylcarbamoyl)phenylcarbamate 5

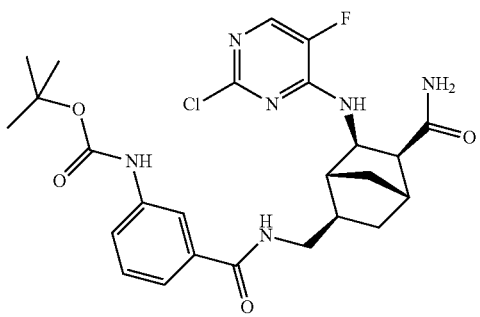 [SMILES: CC(C)(C)OC(=O)Nc1cccc(C(=O)NC[C@@H]2C[C@@H]3C[C@H]2[C@@H](Nc2nc(Cl)ncc2F)[C@H]3C(N)=O)c1]

Into a scintillation vial equipped with a stirbar was dissolved 3-[(tert-butoxy-carbonyl)amino]benzoic acid (0.16 ml; 0.70 mmol) in DCM (5.00 ml). 1-chloro-N,N,2-trimethylprop-1-en-1-amine (592.81 mg; 0.59 mmol) was added dropwise while the mixture stirred at room temperature. After 90 minutes, the reaction mixture was concentrated then dissolved in dry DCM, and cooled in an ice bath while stirring. To this solution was added N,N-dimethylpyridin-4-amine (0.04 ml; 0.36 mmol) and (1R,2S,3R,4R)-5-(aminomethyl)-3-[(2-chloro-5-fluoropyrimidin-4-yl)amino]-bicyclo[2.2.1] heptane-2-carboxamide (93.00 mg; 0.30 mmol and the reaction stirred for 10 hours. The reaction mixture was then concentrated and purified by flash chromatography to afford pure 5 (182 mg, 72%). LC/MS [method B, retention time 6.0 min; m/z 534.25 (M+1)].

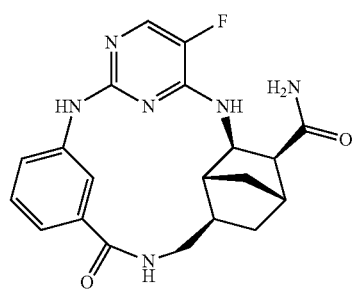 [SMILES: NC(=O)[C@H]1[C@@H]2C[C@H]3CNC(=O)c4cccc(c4)Nc4ncc(F)c(n4)N[C@@H]1[C@@H]3C2]

Example 39

The sequential tert-butoxyocarbonyl deprotection and subsequent ring-closing step was performed in one-pot as described for the Example 24, with (1R,2S,3R,4R)-5-[({[(3-aminophenyl)amino]carbonyl}aminomethyl]-3-[(2-chloro-5-fluoropyrimidin-4-yl)amino]bicyclo[2.2.1]heptane-2-carboxamide (158.60 mg; 0.30 mmol), and an additional equivalent of trifluoroacetic acid, to afford desired macrocycle of Example 39 (2.1 mg, 1.8%). LC/MS [method B, retention time 2.8 min; m/z 397.25 (M+1)].

Example 40

(1R,2S,3R,4R)-3-(2-chloro-5-fluoropyrimidin-4-ylamino)-5-(3-nitrobenzylamino)nethyl)bicyclo[2.2.1]heptane-2-carboxamide 6

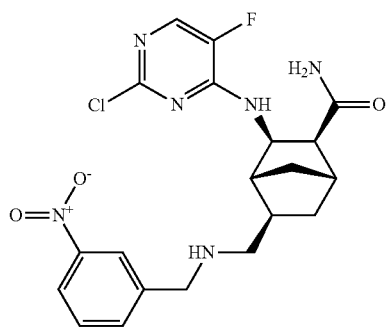 [SMILES: NC(=O)[C@H]1[C@@H]2C[C@@H](CNCc3cccc([N+](=O)[O-])c3)[C@@H](C2)[C@H]1Nc1nc(Cl)ncc1F]

Into a round bottom flask with stir bar was placed (155.6 mg; 0.5 mmol), 1-(bromomethyl)-3-nitrobenzene (101.8 mg; 0.47 mmol), cesium carbonate (193.9 mg; 0.60 mmol) and dimethylformamide (2.00 ml). The flask was swirled to dissolve its contents, then allowed to stir at room temperature until complete. The reaction mixture was concentrated, and purified by flash chromatography using 0-100% ethyl acetate in hexane, followed by a 50% methanol-ethyl acetate flush to give desired product (106 mg, 47.8%) of pure product.

LC/MS [method B, retention time 2.8 min; m/z 449.25 (M+1)].

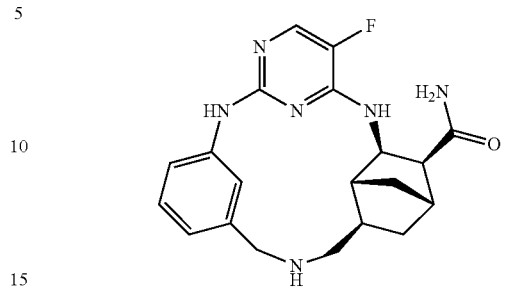

Example 40

The nitro group reduction step was performed as described for Procedure A with (1R,2S,3R,4R)-3-[(2-chloro-5-fluoropyrimidin-4-yl)amino]-5-{[(3-nitrobenzyl)-amino]methyl}bicyclo[2.2.1]heptane-2-carboxamide (106.30 mg; 0.24 mmol; to afford desired aniline, which was used immediately in ring-closing step.

The ring-closing step was performed as described for the synthesis of Example 24 with (1R,2S,3R,4R)-5- [({[(3-aminophenyl)amino]carbonyl}amino)methyl]-3- [(2-chloro-5-fluoropyrimidin-4-yl)-amino]bicyclo[2.2.1]heptane-2-carboxamide (158.60 mg; 0.30 mmol) to afford desired macrocycle of Example 40 (6.3 mg, 7.6%). LC/MS [method B, retention time 0.61 min; m/z 383.25 (M+1)].

Example 41

(1R,2S,3R,4R)-3-(2-chloro-5-fluoropyrimidin-4-ylamino)-5-((3-nitrophenethyl-amino)-methyl)bicyclo[2.2.1]heptane-2-carboxamide

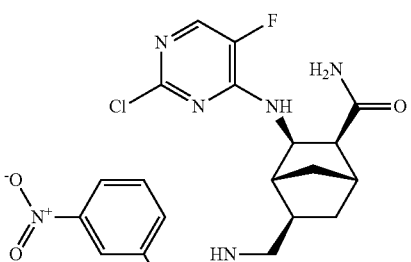

Into a scintillation vial with stirbar was placed (1R,2S,3R,4R)-5-(aminomethyl)-3-[(2-chloro-5-fluoropyrimidin-4-yl)amino]bicyclo[2.2.1]heptane-2-carboxamide (136.60 mg; 0.44 mmol; 1.00 eq.) and 2-(3-nitrophenyl)ethyl 4-methylbenzenesulfonate (279.81 mg; 0.87 mmol; 2.00 eq.). The mixture was dissolved in MeCN (5.00 ml). to the stirring mixture was added triethylamine (0.07 ml; 0.52 mmol; 1.20 eq.). The reaction mixture was concentrated, and purified by flash chromatography using 0-100% ethyl acetate in hexane, followed by a 50% methanol-ethyl acetate flush to give desired product (94.5 mg, 46.9%). LC/MS [method B, retention time 3.1 min; m/z 463.25 (M+1)].

(1R,2S,3R,4R)-5-((3-aminophenethylamino)methyl)-3-(2-chloro-5-fluoropyrimidin-4-ylamino)bicyclo[2.2.1]heptane-2-carboxamide

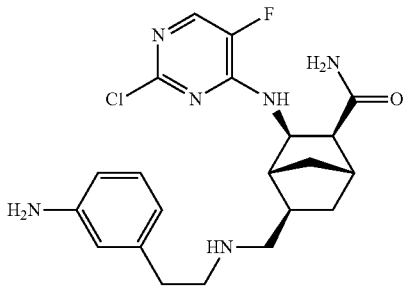 [SMILES: NC(=O)[C@H]1[C@@H]2C[C@@H](CNCCc3cccc(N)c3)[C@@H](C2)[C@H]1Nc1nc(Cl)ncc1F]

The nitro group reduction step was performed as described for Procedure A with (1S,2S,3S,4S,5R)-3-[(2-chloro-5-fluoropyrimidin-4-yl)amino]-5-({2-[(3-nitro-phenyl)amino]-2-oxoethyl}thio)bicyclo[2.2.1]heptane-2-carboxamide (94.50 mg; 0.20 mmol) to afford desired aniline (62 mg, 70.2%). LC/MS [method B, retention time 0.62 min; m/z 433.25 (M+1)].

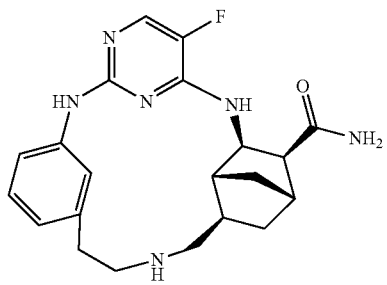 [SMILES: NC(=O)[C@H]1[C@@H]2C[C@H]3CNCCc4cccc(c4)Nc4ncc(F)c(n4)N[C@@H]1[C@@H]3C2]

Example 41

The ring-closing step was performed as described for the synthesis of Example 24 with (1R,2S,3R,4R)-5- [({[(3-aminophenyl)amino]carbonyl}amino)methyl]-3- [(2-chloro-5-fluoropyrimidin-4-yl)-amino]bicyclo[2.2.1]heptane-2-carboxamide (24.20 mg; 0.05 mmol) to afford desired macrocycle of Example 41 (14.9 mg, 18.5%).
LC/MS [method B, retention time 0.59 min; m/z 397.25 (M+1)].

Example 42

(1R,2S,3R,4R)-3-(2-chloro-5-fluoropyrimidin-4-ylamino)-5-(3-(3-nitrophenyl)-ureido)methyl)bicyclo[2.2.1]heptane-2-carboxamide

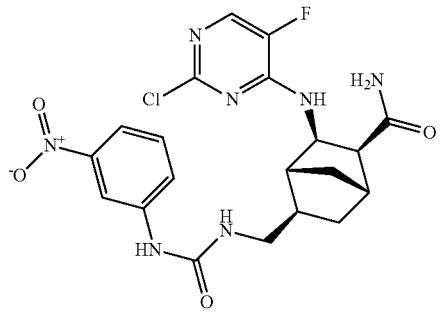

Into a scintillation vial was dissolved (1R,2S,3R,4R)-5-(aminomethyl)-3-[(2-chloro-5-fluoropyrimidin-4-yl)-amino]bicyclo[2.2.1]heptane-2-carboxamide (238.00 mg; 0.76 mmol) in dimethylformamide (2.00 ml), then N,N-diethylethanamine (0.32 ml; 2.28 mmol) and 1-isocyanato-3-nitrobenzene (136.00 mg; 0.83 mmol) were added. The reaction was stirred for 16 hours. The reaction mixture was concentrated, and purified by flash chromatography using 0-100% ethyl acetate in hexane, followed by a 50% methanol-ethyl acetate flush to give the desired product (143.6 mg, 39.6%).
LC/MS [method B, retention time 5.6 min; m/z 478.0 (M+1)].

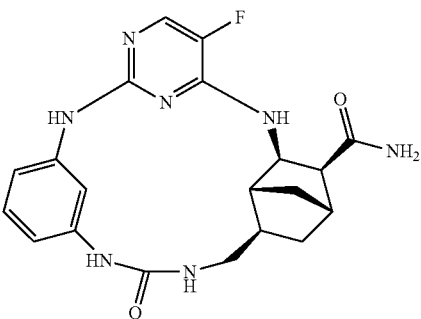 [SMILES: NC(=O)[C@H]1[C@@H]2C[C@H]3CNC(=O)Nc4cccc(c4)Nc4ncc(F)c(n4)N[C@@H]1[C@@H]3C2]

Example 42

The nitro group reduction step was performed as described for Procedure A with (1R,2S,3R,4R)-3-[(2-chloro-5-fluoropyrimidin-4-yl)-amino]-5-{[(3-nitrobenzyl)-amino]methyl}bicyclo[2.2.1]heptane-2-carboxamide (106.30 mg; 0.24 mmol) to afford desired aniline, which was used immediately in ring-closing step.
The ring-closing step was performed as described for the synthesis of Example 24 with (1R,2S,3R,4R)-5- [({[(3-aminophenyl)amino]carbonyl}amino)methyl]-3- [(2-chloro-5-fluoropyrimidin-4-yl)amino]bicyclo[2.2.1]heptane-2-carboxamide (154.20 mg; 0.34 mmol) to afford desired macrocycle of Example 42 (21.4 mg, 15.1%).
LC/MS [method B, retention time 2.8 min; m/z 412.25 (M+1)].

Example 43

(1R,2S,3R,4R,5R)-3-(2-chloro-5-fluoropyrimidin-4-ylamino)-5-((2-(4-nitro-1H-imidazol-1-yl)acetamido)methyl)bicyclo[2.2.1]heptane-2-carboxamide

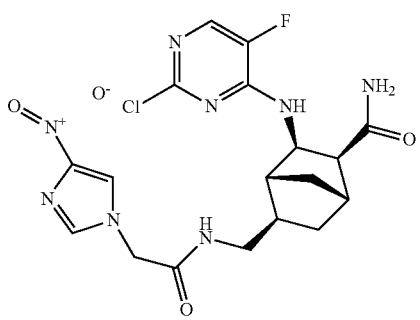

The amidation reaction was performed as described for Procedure C with (1R,2S,3R,4R,5R)-5-(aminomethyl)-3-[(2-chloro-5-fluoropyrimidin-4-yl)-amino]-bicyclo[2.2.1]heptane-2-carboxamide (66.60 mg; 0.17 mmol) and 2-(4-methyl-piperazin-1-yl)-5-nitrobenzoic acid (90.19 mg; 0.34 mmol) to afford the desired product (72.4 mg, 72.7%). LC/MS [method B, retention time 3.9 min; m/z 467.25 (M+1)].

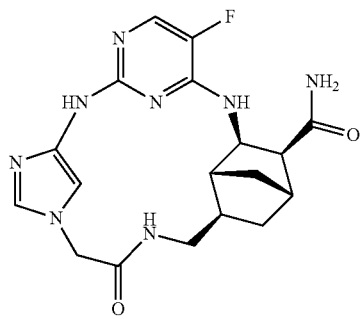 [SMILES: NC(=O)[C@H]1[C@@H]2C[C@H]3CNC(=O)Cn4cnc(c4)Nc4ncc(F)c(n4)N[C@@H]1[C@@H]3C2]

Example 43

The nitro group reduction and concomitant cyclization step was performed as described for Procedure A with (1R,2S,3R,4R)-3-[(2-chloro-5-fluoropyrimidin-4-yl)amino]-6-({[(3-nitrophenyl)amino]carbonyl}amino)bicyclo[2.2.1]heptane-2-carboxamide (100.50 mg; 0.22 mmol) to afford the desired macrocycle of Example 43 (70.9 mg, 46.6%). LC/MS [method A, retention time 0.44 min; m/z 400.0 (M+1)].

Example 44

(1R,2S,3R,4R,5R)-3-(2-chloro-5-fluoropyrimidin-4-ylamino)-5-((2-(4-nitro-1H-pyrazol-1-yl)acetamido)methyl)bicyclo[2.2.1]heptane-2-carboxamide

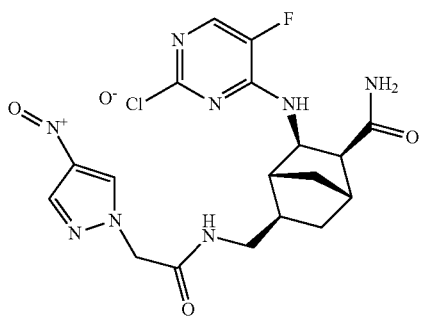

The amidation reaction was performed as described for Procedure C with (1R,2S,3R,4R,5R)-5-(aminomethyl)-3-[(2-chloro-5-fluoropyrimidin-4-yl)-amino]-bicyclo[2.2.1]heptane-2-carboxamide (63.70 mg; 0.17 mmol) to afford the desired product (79.4 mg, 62.6%). LC/MS [method B, retention time 4.4 min; m/z 467.25 (M+1)].

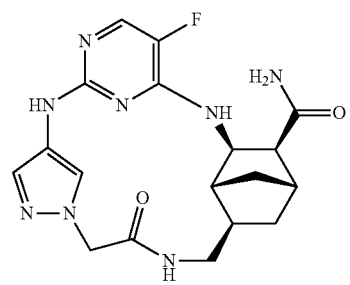 [SMILES: NC(=O)[C@H]1[C@@H]2C[C@H]3CNC(=O)Cn4cc(cn4)Nc4ncc(F)c(n4)N[C@@H]1[C@@H]3C2]

Example 44

A microwave tube equipped with a stirbar was charged with (1R,2S,3R,4R)-6-amino-3-[(2-chloro-5-fluoropyrimidin-4-yl)amino]bicyclo[2.2.1]heptane-2-carboxamide (105.00 mg; 0.35 mmol) and 2-methyl-4-(4-methylpiperazin-1-yl)aniline (208.80 mg; 1.02 mmol) in dry iPrOH (2.00 ml). The vial was sealed, and trifluoroacetic acid (0.04 ml; 0.55 mmol) was then added via syringe. The reaction was refluxed for 16 hours. The crude reaction mixture was purified via Prep HPLC (Waters. Sunfire column, gradient: 0-30% methanol in trifluoroacetic acid solution (0.1% v/v)) to afford compound of Example 44 (23 mg, 18%). LC/MS [method B, retention time 0.65 min; m/z 402.25 (M+1)].

Example 45

(1R,2S,3R,4R)-3-(2-chloro-5-fluoropyrimidin-4-ylamino)-5-(3-nitrophenyl-sulfonamido)methyl)bicyclo[2.2.1]heptane-2-carboxamide

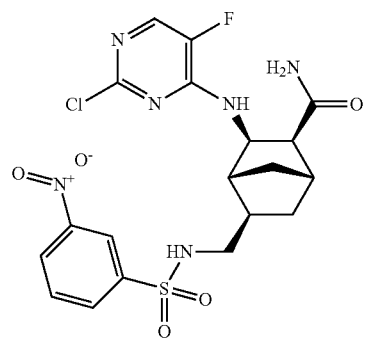

Into a scintillation vial equipped with a stirbar was dissolved (1R,2S,3R,4R)-5-(aminomethyl)-3-[(2-chloro-5-fluoropyrimidin-4-yl)amino]bicyclo[2.2.1]heptane-2-carboxamide (100.00 mg; 0.32 mmol) in THF. To the solution was added triethylamine (0.06 ml; 0.41 mmol) and 3-nitrobenzenesulfonyl chloride (91.82 mg; 0.41 mmol). The vial was sealed and allowed to stir at room temperature. Reaction mixture purified by flash chromatography, using a gradient of 0-100% ethyl acetate in Hexane with a 0-50% methanol in ethyl acetate flush to afford the desired product (96.3 mg, 60.6%). LC/MS [method B, retention time 4.3 min; m/z 498.75 (M+1)].

(1R,2S,3R,4R)-5-((3-aminophenylsulfonamido)methyl)-3-(2-chloro-5-fluoro-pyrimidin-4-ylamino)bicyclo[2.2.1]heptane-2-carboxamide

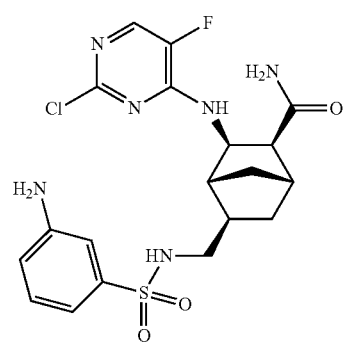 [SMILES: NC(=O)[C@H]1[C@@H]2C[C@@H](CNS(=O)(=O)c3cccc(N)c3)[C@@H](C2)[C@H]1Nc1nc(Cl)ncc1F]

The nitro group reduction step was performed as described for Procedure B with 1R,2S,3R,4R)-3-[(2-chloro-5-fluoro-pyrimidin-4-yl)-amino]-5-({[(3-nitrophenyl)-sulfonyl]amino}methyl)bicyclo[2.2.1]heptane-2-carboxamide (93.00 mg; 0.19 mmol) to afford desired aniline (87.4 mg, 85.1%). LC/MS [method B, retention time 3.4 min; m/z 469.25 (M+1)].

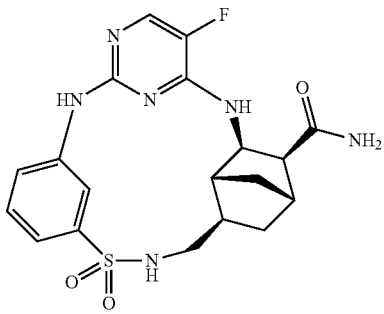 [SMILES: NC(=O)[C@H]1[C@@H]2C[C@H]3CNS(=O)(=O)c4cccc(c4)Nc4ncc(F)c(n4)N[C@@H]1[C@@H]3C2]

Example 45

The ring-closing step was performed as described for the synthesis of Example 24 with (1R,2S,3R,4R)-5-({[(3-aminophenyl)sulfonyl]amino}methyl)-3-[(2-chloro-5-fluoropyrimidin-4-yl)amino]bicyclo[2.2.1]heptane-2-carboxamide (93.00 mg; 0.20 mmol) to afford desired macrocycle of Example 43 (7.3 mg, 8.5%). LC/MS [method B, retention time 0.62 min; m/z 433.25 (M+1)].

Example 46

(1R,2S,3R,4R,5R)-3-(2-chloro-5-fluoropyrimidin-4-ylamino)-5-(((3-nitrophenyl)-methylsulfonamidolmethyl)bicyclo[2.2.1]heptane-2-carboxamide

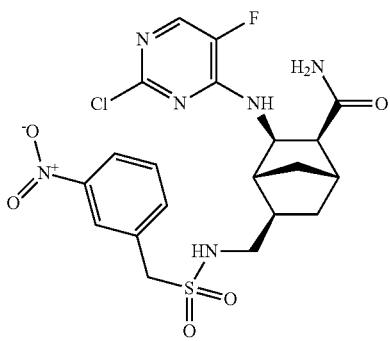

Into a scintillation vial equipped with a stirbar was dissolved (1R,2S,3R,4R)-5-(aminomethyl)-3-[(2-chloro-5-fluoropyrimidin-4-yl)amino]bicyclo[2.2.1]heptane-2-carboxamide (98.20 mg; 0.32 mmol) in THF. To the solution was added triethylamine (0.06 ml; 0.41 mmol) and 3-nitro-alpha-toluenesulfonyl chloride (97.63 mg; 0.41 mmol). The vial was sealed and allowed to stir at room temperature. Reaction mixture purified by flash chromatography using a gradient of 0-100% ethyl acetate in Hexane with a 0-50% methanol in ethyl acetate flush to afford the desired product (58.3 mg, 35.7%). LC/MS [method B, retention time 4.2 min; m/z 513.25 (M+1)].

(1R,2S,3R,4R,5R)-5-(((3-aminophenyl)methylsulfonamido)methyl)-3-(2-chloro-5-fluoropyrimidin-4-ylamino)bicyclo[2.2.1]heptane-2-carboxamide

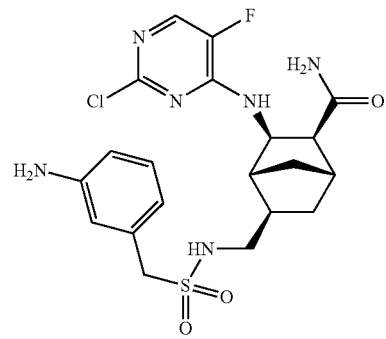 [SMILES: NC(=O)[C@H]1[C@@H]2C[C@@H](CNS(=O)(=O)Cc3cccc(N)c3)[C@@H](C2)[C@H]1Nc1nc(Cl)ncc1F]

The nitro group reduction step was performed as described for Procedure B with (1R,2S,3R,4R,5R)-3-[(2-chloro-5-fluoropyrimidin-4-yl)amino]-5-({[(3-nitrobenzyl)-sulfonyl]amino}methyl)bicyclo[2.2.1]heptane-2-carboxamide (53.10 mg; 0.10 mmol) to afford desired aniline (46.7 mg, 93.4%). LC/MS [method B, retention time 2.3 min; m/z 483.25 (M+1)].

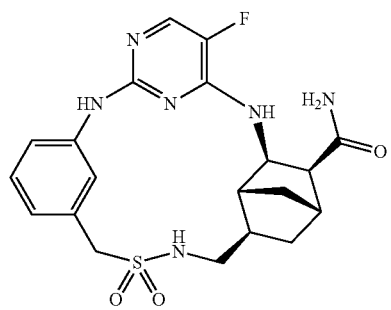 [SMILES: NC(=O)[C@H]1[C@@H]2C[C@H]3CNS(=O)(=O)Cc4cccc(c4)Nc4ncc(F)c(n4)N[C@@H]1[C@@H]3C2]

Example 46

The ring-closing step was performed as described for the synthesis of Example 24 with (1R,2S,3R,4R,5R)-5-({[(3-aminobenzyl)sulfonyl]amino}methyl)-3-[(2-chloro-5-fluoropyrimidin-4-yl)amino]bicyclo[2.2.1]heptane-2-carboxamide (46.90 mg; 0.10 mmol) to afford desired macrocycle of Example 46 (43.4 mg, 6.3%).
LC/MS [method B, retention time 1.7 min; m/z 447.25 (M+1)].

Example 47

(1R,2S,3R,4R,5R)-3-(2-chloro-5-fluoropyrimidin-4-ylamino)-5-(2-(3-nitrophenyl-amino)-2-oxoethylamino)methyl)bicyclo[2.2.1]heptane-2-carboxamide

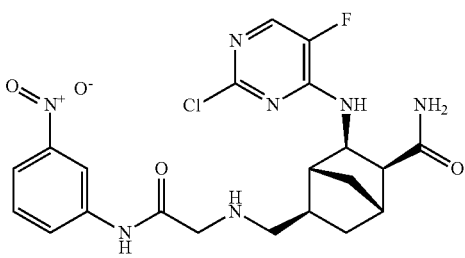

Into a microwave vial with stir bar was dissolved (1R,2S,3R,4R,5R)-5-(amino-methyl)-3-[(2-chloro-5-fluoropyrimidin-4-yl)-amino]bicyclo[2.2.1]heptane-2-carboxamide (66.90 mg; 0.21 mmol), 2-chloro-N-(3-nitrophenyl)-acetamide (50.33 mg; 0.23 mmol), cesium carbonate (0.04 ml; 0.53 mmol) in tetrahydrofuran (3.00 mL). The vial placed in microwave for 16 minutes at 100° C. The reaction mixture was purified via Waters Prep HPLC using gradient of 0-30% methanol in water over 30 minutes to afford desired product (73.2 mg, 69.8%). LC/MS [method B, retention time 2.4 min; m/z 492.25 (M+1)].

(1R,2S,3R,4R,5R)-5-((2-(3-aminophenylamino)-2-oxoethylamino)methyl)-3-(2-chloro-5-fluoropyrimidin-4-ylamino)bicyclo[2.2.1]heptane-2-carboxamide

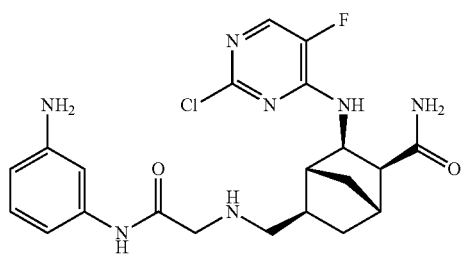 [SMILES: NC(=O)[C@H]1[C@@H]2C[C@@H](CNCC(=O)Nc3cccc(N)c3)[C@@H](C2)[C@H]1Nc1nc(Cl)ncc1F]

The nitro group reduction step was performed as described for Procedure B with (1R,2S,3R,4R,5R)-3-(2-chloro-5-fluoropyrimidin-4-ylamino)-5-(2-(3-nitrophenyl-amino)-2-oxoethylamino)methyl)bicyclo[2.2.1]heptane-2-carboxamide (34.8 mg, 0.07 mmol) to afford desired aniline. LC/MS [method B, retention time 0.63 min; m/z 462.25 (M+1)].

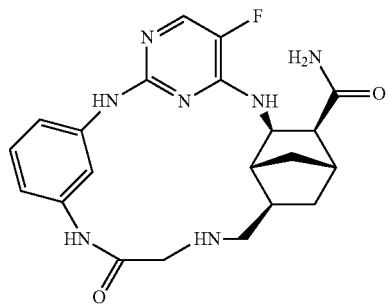 [SMILES: NC(=O)[C@H]1[C@@H]2C[C@H]3CNCC(=O)Nc4cccc(c4)Nc4ncc(F)c(n4)N[C@@H]1[C@@H]3C2]

Example 47

The ring-closing step was performed as described for the synthesis of Example 24 with (1R,2S,3R,4R,5R)-5-((2-(3-aminophenylamino)-2-oxoethylamino)methyl)-3-(2-chloro-5-fluoropyrimidin-4-ylamino)bicyclo[2.2.1]heptane-2-carboxamide (34.3 mg, 0.07 mmol) to afford desired macrocycle of Example 47 (13.9 mg, 44%). LC/MS [method B, retention time 0.56 min; m/z 426.25 (M+1)].

Example 48

(1R,2S,3R,4R,5R)-3-(2-chloro-5-fluoropyrimidin-4-ylamino)-5-((N-(3-nitrobenzyl)-acetamido)methyl)bicyclo[2.2.1]heptane-2-carboxamide

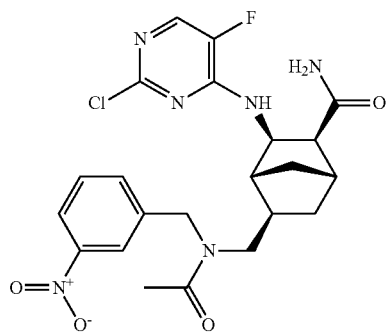 [SMILES: CC(=O)N(Cc1cccc([N+](=O)[O-])c1)C[C@@H]1C[C@@H]2C[C@H]1[C@@H](Nc1nc(Cl)ncc1F)[C@H]2C(N)=O]

Into a clean dry round bottom flask equipped with stirbar was dissolved (1R,2S,3R,4R,5R)-3-[(2-chloro-5-fluoropyrimidin-4-yl)-amino]-5-{[(3-nitrobenzyl)-amino]methyl}-bicyclo[2.2.1]heptane-2-carboxamide (141.20 mg; 0.31 mmol) in THF (5.00 ml). To the mixture was added N,N-diethylethanamine (0.09 ml; 0.63 mmol) followed by acetyl chloride (0.03 ml; 0.47 mmol) and the solution was stirred at room temperature for 10 minutes. The concentrated reaction mixture was purified via Prep RP-HPLC using a gradient of 0-30% methanol in 0.1% trifluoroacetic acid (aq) solution over 30 minutes to afford desired product (128.3 mg, 83%). LC/MS [method B, retention time 3.8 min; m/z 491.25 (M+1)].

(1R,2S,3R,4R)-5-((N-(3-aminobenzyl)acetamido)methyl)-3-(2-chloro-5-fluoro-pyrimidin-4-ylamino)bicyclo[2.2.1]heptane-2-carboxamide

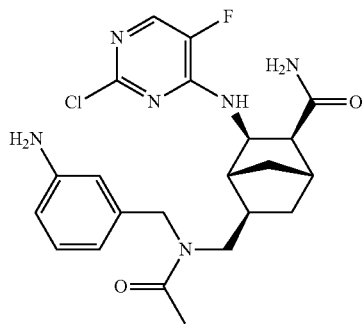 [SMILES: CC(=O)N(Cc1cccc(N)c1)C[C@@H]1C[C@@H]2C[C@H]1[C@@H](Nc1nc(Cl)ncc1F)[C@H]2C(N)=O]

The nitro group reduction step was performed as described for Procedure B with (1R,2S,3R,4R,5R)-3-(2-chloro-5-fluoropyrimidin-4-ylamino)-5-((N-(3-nitrobenzyl)-acetamido)methyl)bicyclo[2.2.1]heptane-2-carboxamide (128.3 mg, 0.29 mmol) to afford desired aniline. LC/MS [method B, retention time 2.3 min; m/z 461.25 (M+1)].

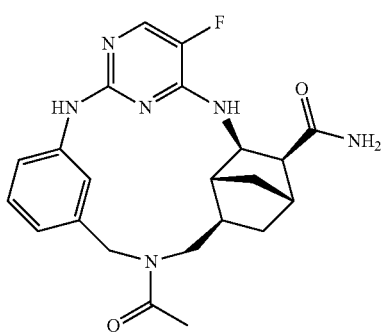 [SMILES: CC(=O)N1Cc2cccc(c2)Nc2ncc(F)c(n2)N[C@@H]2[C@@H]3C[C@@H](C[C@H]3C1)[C@@H]2C(N)=O]

Example 48

The ring-closing step was performed as described for the synthesis of Example 24 with (1R,2S,3R,4R)-5-((N-(3-aminobenzyl)acetamido)methyl)-3-(2-chloro-5-fluoropyrimidin-4-ylamino)bicyclo[2.2.1]heptane-2-carboxamide (128.3 mg, 0.28 mmol) to afford desired macrocycle of Example 48 (53.5 mg, 45.4%). LC/MS [method B, retention time 0.86 min; m/z 425.25 (M+1)].

Example 49

(1R,2S,3R,4R,5R)-3-(2-chloro-5-fluoropyrimidin-4-ylamino)-5-((methyl(3-nitro-benzyl)amino)methyl)bicyclo[2.2.1]heptane-2-carboxamide

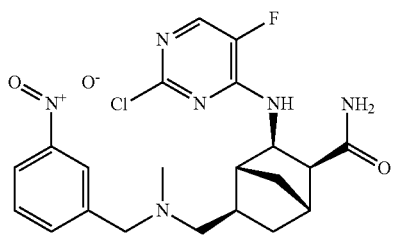

To a solution of (1R,2S,3R,4R,5R)-3-[(2-chloro-5-fluoropyrimidin-4-yl)amino]-5-{[(3-nitrobenzyl)amino]methyl}bicyclo[2.2.1]heptane-2-carboxamide (62.00 mg; 0.14 mmol) in methanol (10.00 ml) was added 37% (aq) solution of AcC(15.42 µl; 0.21 mmol). The reaction is stirred at room temperature until imine formation complete as determined by TLC. Concentrated reaction mixture to remove water, then took up residue in methanol, and added sodium triacetoxyborohydride (87.82 mg; 0.41 mmol) with a drop of acetic acid. Stirred reaction mixture for 15 hours at ambient temperature. Concentrated reaction mixture then subjected directly to nitro reduction. LC/MS [method B, retention time 2.1 min; m/z 463.25 (M+1)].

(1R,2S,3R,4R,5R)-5-(((3-aminobenzyl)(methyl)amino)methyl)-3-(2-chloro-5-fluoropyrimidin-4-ylamino)bicyclo[2.2.1]heptane-2-carboxamide

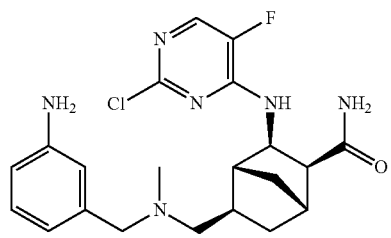 [SMILES: CN(Cc1cccc(N)c1)C[C@@H]1C[C@@H]2C[C@H]1[C@@H](Nc1nc(Cl)ncc1F)[C@H]2C(N)=O]

The nitro group reduction step was performed as described for Procedure B with (1R,2S,3R,4R,5R)-3- [(2-chloro-5-fluoropyrimidin-4-yl)amino]-5-{[methyl(3-nitrobenzyl)amino]methyl}bicyclo[2.2.1]heptane-2-carboxamide (64.80 mg; 0.14 mmol) to afford desired aniline (55 mg, 90.8%). LC/MS [method B, retention time 0.71 min; m/z 433.25 (M+1)].

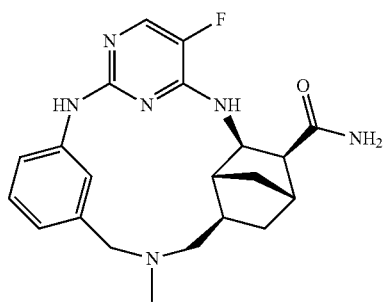 [SMILES: CN1Cc2cccc(c2)Nc2ncc(F)c(n2)N[C@@H]2[C@@H]3C[C@@H](C[C@H]3C1)[C@@H]2C(N)=O]

Example 49

The ring-closing step was performed as described for the synthesis of Example 24 with (1R,2S,3R,4R,5R)-5-(((3-aminobenzyl) (methyl)amino)methyl)-3- (2-chloro-5-fluoropyrimidin-4-ylamino)bicyclo[2.2.1]heptane-2-carboxamide (55 mg, 0.13 mmol) to afford desired macrocycle of Example 49 (3 mg, 5.5%). LC/MS [method B, retention time 0.61 min; m/z 397.25 (M+1)].

Example 50

(E)-2-(3,5-di-tert-butyl-2-methoxybenzylidene-amino)-2,2-diphenylacetate

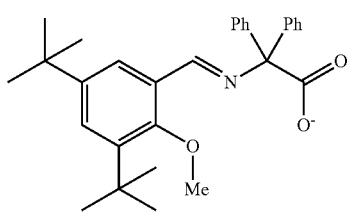 [SMILES: COc1c(/C=N/C(C(=O)[O-])(c2ccccc2)c2ccccc2)cc(C(C)(C)C)cc1C(C)(C)C]

Into a 100 mL RBF equipped with a stirbar was placed amino(diphenyl)acetic acid (1.07 g; 4.69 mmol), EtOH (50.00 ml) and potassium hydroxide (0.26 g; 4.69 mmol). The suspension was allowed to stir at room temperature for 30 minutes. To the reaction flask was added 3,5-di-tert-butyl-2-hydroxybenzaldehyde (1.00 g; 4.27 mmol). The reaction was stirred at room temperature for 10 hours, then removed solvent en vacuo then further dried under high vacuum for 8 hours to yield a hygroscopic, yellow solid (1.87 g; 90.9%). LC/MS [method B, retention time 3.2 min)

(1S,2S,3R,4S,5R)-5-azido-3-(2-chloro-5-fluoropyrimidin-4-ylamino)bicyclo[2.2.1]heptane-2-carboxamide and (1R,2S,3R,4R,6S)-6-azido-3-(2-chloro-5-fluoropyrimidin-4-ylamino)bicyclo[2.2.1]heptane-2-carboxamide

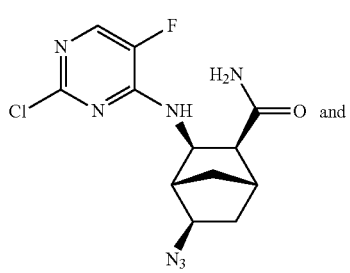

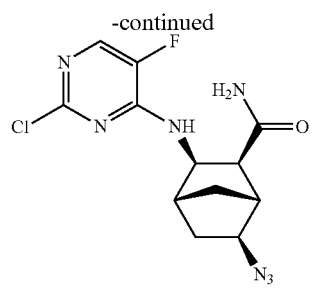

Cobalt(II) Borofluoride hexahydrate (10.22 mg; 0.03 mmol) and potassium {[(1E)-(3,5-di-tert-butyl-2-hydroxyphenyl)methylene]amino}(diphenyl)acetate (14.45 mg; 0.03 mmol) were dissolved in EtOH (2.50 ml) at room temperature for 10 minutes, under Argon. To the solution was added (2S,3R)-3-[(2-chloro-5-fluoropyrimidin-4-yl)amino]bicyclo[2.2.1]hept-5-ene-2-carboxamide (141.35 mg; 0.50 mmol), followed by polystyrene bound 4-methylbenzenesulfonyl azide (500.00 mg; 0.75 mmol; 1.5 mmol/g loading) and tert-butyl hydroperoxide (0.03 ml; 5.50 M; 0.14 mmol). After 5 minutes of stirring, hexamethyldisiloxane (0.16 ml; 0.75 mmol) was added dropwise and the solution was stirred at ambient temperature for took 3 days. The reaction was quenched reaction with DI water (5 mL), filtered using silica plug, then diluted with 50 mL EtOAc. The organic layer was washed three times with saturated sodium bicarbonate solution (aq). The aqueous layer was back extracted twice with ~50 EtOAc. Organic layers were combined, washed twice with brine solution, dried over magnesium sulfate, filtered and concentrated en vacuo. The resulting residue was taken up in 3 mL of DMSO, injected onto prep HPLC column and separated on reverse phase column using a gradient of 0%-100% ACN in 0.1% TFA (aq) solution to yield the (1S,2S,3R,4S,5R)-5-azido-3-(2-chloro-5-fluoropyrimidin-4-ylamino)bicyclo[2.2.1]heptane-2-carboxamide, LC/MS [method B, retention time 2.7 min; m/z 300.00 (M+1)]; and (1R,2S,3R,4R,6S)-6-azido-3-(2-chloro-5-fluoropyrimidin-4-ylamino)bicyclo[2.2.1]heptane-2-carboxamide, LC/MS [method B, retention time 3.8 min; m/z 300.00 (M+1)].

(1S,2S,3R,4R,5R)-5-amino-3-(2-chloro-5-fluoropyrimidin-4-ylamino)bicyclo[2.2.1]heptane-2-carboxamide

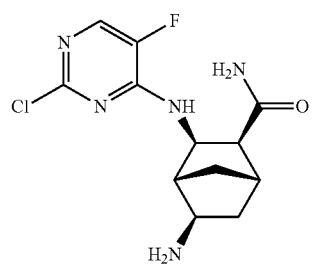 [SMILES: NC(=O)[C@H]1[C@H]2C[C@@H]([C@H]1Nc1nc(Cl)ncc1F)[C@H](N)C2]

To a solution of (1S,2S,3R,4S,5R)-5-azido-3-(2-chloro-5-fluoropyrimidin-4-ylamino)bicyclo[2.2.1]heptane-2-carboxamide (20.9 g, 63.7 mmol) in THF (400 mL) was added PPh$_2$ (33.4 g, 127.3 mmol) and water (46 mL) and the reaction mixture was stirred at rt for 2 days. The mixture was concentrated and taken up in 1 N HCl (200 mL) and extracted with ethyl ether (300 mL×2). The combined organic layers were back washed with 1 N HCl (150 mL). The combined aqueous layers were back extracted with EtOAc (100 mL) and basified with KOH until pH 10. The mixture was extracted successively with EtOAc (200 mL×2) to give crude adduct. The crude was applied to silica gel chromatography to give desired adduct (8.9 g, 22%).

(1S,2S,3R,4R,5R)-3-(2-chloro-5-fluoropyrimidin-4-ylamino)-5-(2-(2-(4-methyl-piperazin-1-yl)-5-nitrophenyl)acetamido)bicyclo[2.2.1]heptane-2-carboxamide

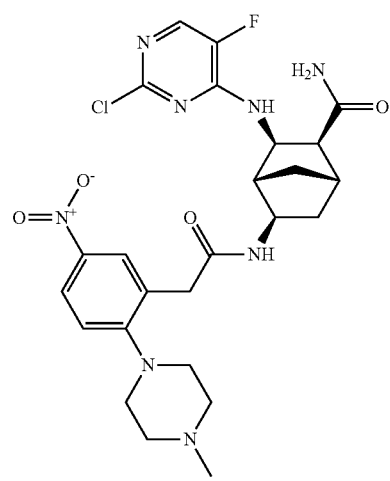 [SMILES: CN1CCN(c2ccc([N+](=O)[O-])cc2CC(=O)N[C@@H]2C[C@@H]3C[C@H]2[C@@H](Nc2nc(Cl)ncc2F)[C@H]3C(N)=O)CC1]

The amidation reaction was performed as described for Procedure C with [2-(4-methylpiperazin-1-yl)-5-nitrophenyl]acetic acid (160.25 mg; 0.57 mmol), o-(7-azabenzotriazol-1-yl)-n,n,n',n'-tetramethyluronium hexafluoro-phosphate (163.62 mg; 0.43 mmol), (1R,2R,4S,5S,6R)-5-(aminocarbonyl)-6-[(2-chloro-5-fluoro-pyrimidin-4-yl)-amino]bicyclo[2.2.1]heptan-2-aminium trifluoroacetate (118.70 mg; 0.29 mmol) and N-ethyl-N-isopropylpropan-2-amine (0.24 ml; 1.43 mmol) in dimethylformamide (3.00 ml) to afford the desired product (64.2 mg, 39.9%). LC/MS [method B, retention time 1.9 min; m/z 561.25 (M+1)].

(1S,2S,3R,4R,5R)-5-(2-(5-amino-2-(4-methylpiperazin-1-yl)-phenyl)acetamido)-3-(2-chloro-5-fluoropyrimidin-4-ylamino)bicyclo[2.2.1]heptane-2-carboxamide

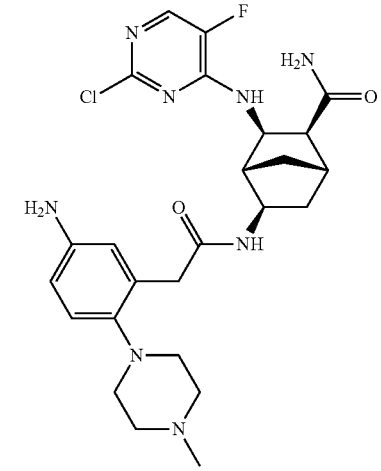 [SMILES: CN1CCN(c2ccc(N)cc2CC(=O)N[C@@H]2C[C@@H]3C[C@H]2[C@@H](Nc2nc(Cl)ncc2F)[C@H]3C(N)=O)CC1]

The nitro group reduction step was performed as described for Procedure B with (1S,2S,3R,4R,5R)-3-[(2-chloro-5-fluoropyrimidin-4-yl)amino]-5-({[2-(4-methyl-piperazin-1-yl)-5-nitrophenyl]acetyl}amino)bicyclo[2.2.1]heptane-2-carboxamide (64.20 mg; 0.11 mmol) to afford desired aniline LC/MS [method B, retention time 0.58 min; m/z 531.25 (M+1)].

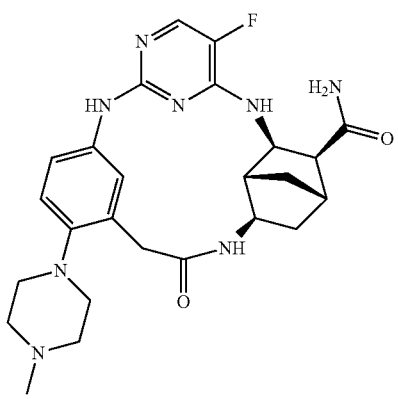 [SMILES: CN1CCN(c2ccc3cc2CC(=O)N[C@@H]2C[C@@H]4C[C@H]2[C@@H](Nc2nc(ncc2F)N3)[C@H]4C(N)=O)CC1]

Example 50

The ring-closing step was performed as described for the synthesis of Example 24 with (1S,2S,3R,4R,5R)-5-({[5-amino-2-(4-methylpiperazin-1-yl)phenyl]acetyl}-amino)-3-[(2-chloro-5-fluoropyrimidin-4-yl)amino]bicyclo[2.2.1]heptane-2-carboxamide (59.20 mg; 0.11 mmol) to afford desired macrocycle of Example 50 (2.9 mg, 5.3%). LC/MS [method B, retention time 0.74 min; m/z 495.25 (M+1)].

Example 51

(1S,2S,3R,4R,5R)-3-(2-chloro-5-fluoropyrimidin-4-ylamino)-5-(2-(3-nitrophenyl)-acetamido)bicyclo[2.2.1]heptane-2-carboxamide

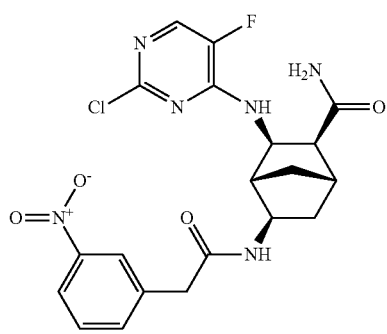 [SMILES: NC(=O)[C@H]1[C@H]2C[C@@H]([C@H]1Nc1nc(Cl)ncc1F)[C@H](NC(=O)Cc1cccc([N+](=O)[O-])c1)C2]

The amidation reaction was performed as described for Procedure C with (3-nitrophenyl)acetic acid (80.21 mg; 0.44 mmol), o-(7-azabenzotriazol-1-yl)-n,n,n',n'-tetramethyluronium hexafluoro-phosphate (126.27 mg; 0.33 mmol), (1R,2R,4S,5S,6R)-5-(aminocarbonyl)-6-[(2-chloro-5-fluoropyrimidin-4-yl)amino]-bicyclo[2.2.1]heptan-2-aminium trifluoroacetate (91.60 mg; 0.22 mmol) and N-ethyl-N-isopropylpropan-2-amine (0.18 ml; 1.11 mmol) dimethylformamide (3.00 ml)) to afford the desired product (59 mg, 57.8%). LC/MS [method B, retention time 3.9 min; m/z 463.25 (M+1)].

(1S,2S,3R,4R,5R)-5-(2-(3-aminophenyl)acetamido)-3-(2-chloro-5-fluoropyrimidin-4-ylamino)bicyclo[2.2.1]heptane-2-carboxamide

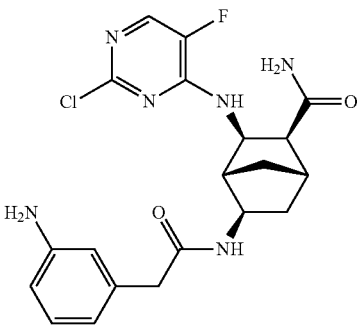 [SMILES: NC(=O)[C@H]1[C@H]2C[C@@H]([C@H]1Nc1nc(Cl)ncc1F)[C@H](NC(=O)Cc1cccc(N)c1)C2]

The nitro group reduction step was performed as described for Procedure B with (1S,2S,3R,4R,5R)-3-[(2-chloro-5-fluoropyrimidin-4-yl)-amino]-5-({[2-(4-methyl-piperazin-1-yl)-5-nitrophenyl]acetyl}amino)bicyclo[2.2.1]heptane-2-carboxamide (64.20 mg; 0.11 mmol) to afford desired aniline LC/MS [method B, retention time 1.1 min; m/z 433.25 (M+1)].

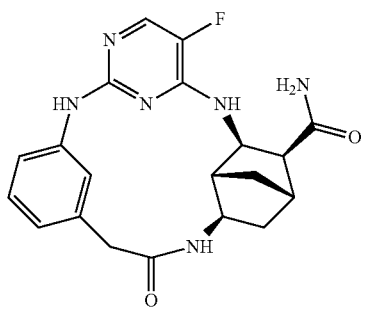 [SMILES: NC(=O)[C@H]1[C@H]2C[C@H]3[C@H]1Nc1nc(ncc1F)Nc1cccc(c1)CC(=O)N[C@@H]3C2]

Example 51

The ring-closing step was performed as described for the synthesis of Example 24 with (1S,2S,3R,4R,5R)-5-{[(3-aminophenyl)acetyl]amino}-3- [(2-chloro-5-fluoro-pyrimidin-4-yl)-amino]bicyclo[2.2.1]heptane-2-carboxamide (59.20 mg; 0.14 mmol) to afford desired macrocycle of Example 51 (4.4 mg, 8.1%). LC/MS [method B, retention time 2.4 min; m/z 397.25 (M+1)].

Example 52

3-nitrobenzyl (1R,2R,4S,5S,6R)-5-carbamoyl-6-(2-chloro-5-fluoropyrimidin-4-ylamino)bicyclo[2.2.1]heptan-2-ylcarbamate

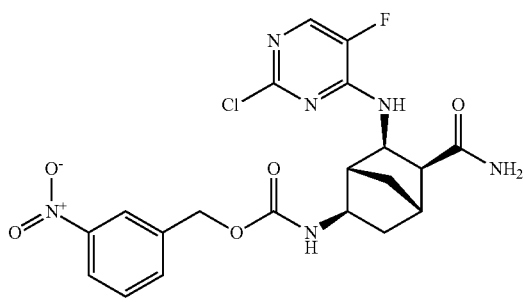 [SMILES: NC(=O)[C@H]1[C@H]2C[C@@H]([C@H]1Nc1nc(Cl)ncc1F)[C@H](NC(=O)OCc1cccc([N+](=O)[O-])c1)C2]

The carbamate formation was performed as described for Procedure D with (3-nitrophenyl)methanol (0.06 ml; 0.48 mmol) in toluene (3.00 ml), N,N-diethylethanamine (0.13 ml; 0.97 mmol), 4-nitrophenyl chloridocarbonate (0.13 ml; 0.97 mmol), and (1S,2S,3R,4R,5R)-5-amino-3-[(2-chloro-5-fluoropyrimidin-4-yl)-amino]bicyclo[2.2.1]heptane-2-carboxamide (100.00 mg; 0.33 mmol) in 1 mL dimethylformamide to afford the desired carbamate (19.4 mg, 16.8%). LC/MS [method B, retention time 4.4 min; m/z 479.25 (M+1)].

3-aminobenzyl (1R,2R,4S,5S,6R)-5-carbamoyl-6-(2-chloro-5-fluoropyrimidin-4-ylamino)bicyclo[2.2.1]heptan-2-ylcarbamate

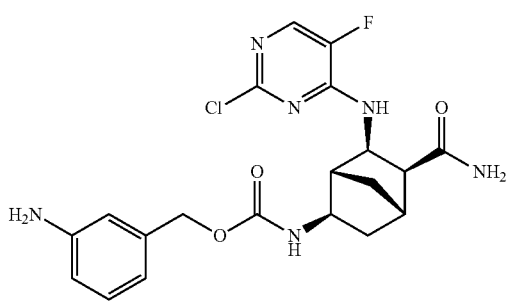 [SMILES: NC(=O)[C@H]1[C@H]2C[C@@H]([C@H]1Nc1nc(Cl)ncc1F)[C@H](NC(=O)OCc1cccc(N)c1)C2]

The nitro group reduction step was performed as described for Procedure B with 3-nitrobenzyl {(1R,2R,4S,5S,6R)-5-(aminocarbonyl)-6-[(2-chloro-5-fluoro-pyrimidin-4-yl)-amino]bicyclo[2.2.1]hept-2-yl}carbamate (19.40 mg; 0.04 mmol) in methanol (20.00 ml) to afford desired aniline (15.9 mg, 87.4%). LC/MS [method B, retention time 2.9 min; m/z 449.25 (M+1)].

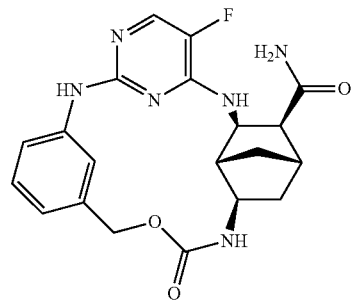 [SMILES: NC(=O)[C@H]1[C@H]2C[C@H]3[C@H]1Nc1nc(ncc1F)Nc1cccc(c1)COC(=O)N[C@@H]3C2]

Example 52

The ring-closing step was performed as described for the synthesis of Example 24 with 3- aminobenzyl-{(1R,2R,4S,5S,6R)-5- (aminoc arbonyl)-6-[(2-chloro-5-fluoro-pyrimidin-4-yl)-amino]bicyclo[2.2.1]hept-2-yl}carbamate (22.90 mg; 0.05 mmol) to afford desired macrocycle of Example 52 (1 mg, 3.3%). LC/MS [method B, retention time 1.5 min; m/z 413.25 (M+1)].

Example 53

2-(4-methylpiperazin-1-yl)-5-nitrobenzyl (1R,2R,4S,5S,6R)-5-carbamoyl-6-(2-chloro-5-fluoropyrimidin-4-ylamino)bicyclo[2.2.1]heptan-2-ylcarbamate

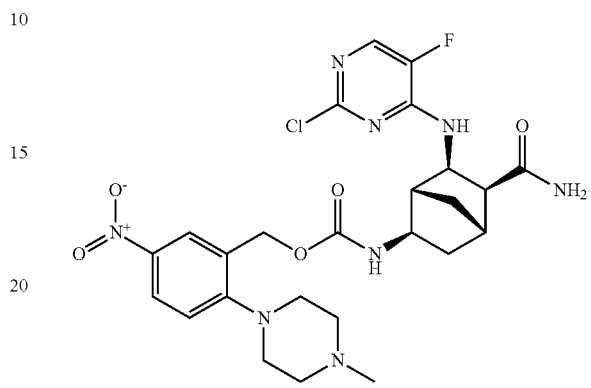

The carbamate formation was performed as described for Procedure D with [2-(4-methylpiperazin-1-yl)-5-nitrophenyl]methanol (167.67 mg; 0.67 mmol) in toluene (3.00 ml), N,N-diethylethanamine (0.09 ml; 0.67 mmol), 4-nitrophenyl chloridocarbonate (134.50 mg; 0.67 mmol) and (1S,2S,3R,4R,5R)-5-amino-3-[(2-chloro-5-fluoropyrimidin-4-yl)-amino]bicyclo[2.2.1]heptane-2-carboxamide (100.00 mg; 0.33 mmol) in 1 mL dimethylformamide to afford the desired carbamate (95.2 mg, 49.5%). LC/MS [method B, retention time 2.5 min; m/z 577.25 (M+1)].

5-amino-2-(4-methylpiperazin-1-yl)benzyl (1R,2R,4S,5S,6R)-5-carbamoyl-6-(2-chloro-5-fluoropyrimidin-4-ylamino)bicyclo[2.2.1]heptan-2-ylcarbamate

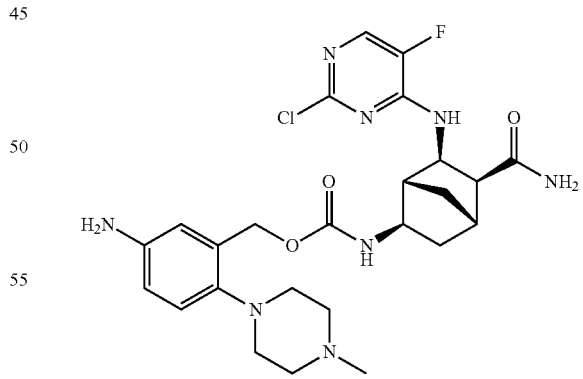

The nitro group reduction step was performed as described for Procedure B with 2-(4-methylpiperazin-1-yl)-5-nitrobenzyl {(1R,2R,4S,5S,6R)-5-(aminocarbonyl)-6-[(2-chloro-5-fluoropyrimidin-4-yl)amino]bicyclo[2.2.1]hept-2-yl}carbamate (95.20 mg; 0.16 mmol) in methanol (20.00 ml) to afford desired aniline (60.4 mg, 66.9%). LC/MS [method B, retention time 0.66 min; m/z 547.25 (M+1)].

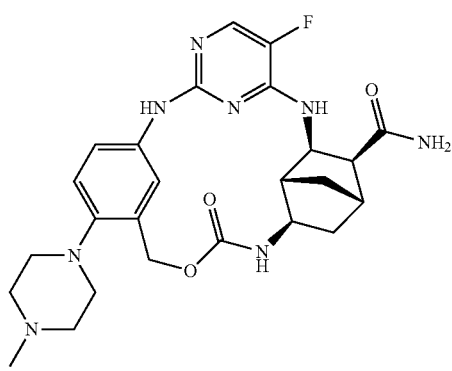 [SMILES: CN1CCN(c2ccc3cc2COC(=O)N[C@@H]2C[C@@H]4C[C@H]2[C@@H](Nc2nc(ncc2F)N3)[C@H]4C(N)=O)CC1]

Example 53

The ring-closing step was performed as described for the synthesis of Example 24 with hydrochloric acid (0.60 ml; 4.00 M; 19.75 mmol; 4.0M in dioxane) and 5-amino-2-(4-methylpiperazin-1-yl)benzyl {(1R,2R,4S,5S,6R)-5-(aminocarbonyl)-6-[(2-chloro-5-fluoropyrimidin-4-yl)amino]bicyclo[2.2.1]hept -2-yl}carbamate (60.40 mg; 0.11 mmol) to afford desired macrocycle of Example 53 (4.9 mg, 8.7%). LC/MS [method B, retention time 0.62 min; m/z 511.25 (M+1)].

Example 54

(1S,2S,3R,4R,5R)-3-(2-chloro-5-fluoropyrimidin-4-ylamino)-5-(3-(3-nitrobenzyl)ureido)bicyclo[2.2.1]heptane-2-carboxamide

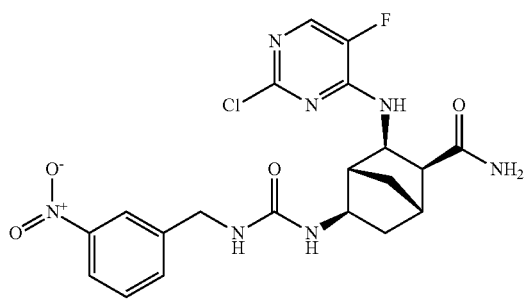 [SMILES: NC(=O)[C@H]1[C@H]2C[C@@H]([C@H]1Nc1nc(Cl)ncc1F)[C@H](NC(=O)NCc1cccc([N+](=O)[O-])c1)C2]

The urea formation was performed as described for Procedure D with (3-nitrophenyl)methanaminium chloride (45.59 mg; 0.24 mmol) in THF (3.00 ml), N,N-diethylethanamine (0.07 ml; 0.48 mmol), 4-nitrophenyl chloridocarbonate (48.72 mg; 0.24 mmol) and (1R,2R,4S,5S,6R)-5-(aminocarbonyl) -6-[(2-chloro-5-fluoropyrimidin-4-yl)amino]bicyclo[2.2.1]heptan-2-aminium trifluoroacetate (50.00 mg; 0.12 mmol) in 1 mL dimethylformamide to afford the desired urea (50.7 mg, 87.8%). LC/MS [method B, retention time 3.8 min; m/z 478.25 (M+1)].

(1S,2S,3R,4R,5R)-5-(3-(3-aminobenzyl)ureido) -3-(2-chloro-5-fluoropyrimidin-4-ylamino)bicyclo[2.2.1]heptane-2-carboxamide

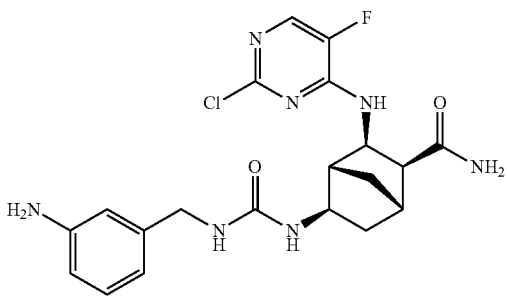 [SMILES: NC(=O)[C@H]1[C@H]2C[C@@H]([C@H]1Nc1nc(Cl)ncc1F)[C@H](NC(=O)NCc1cccc(N)c1)C2]

The nitro group reduction step was performed as described for Procedure B with (1S,2S,3R,4R,5R)-3-(2-chloro-5-fluoropyrimidin-4-ylamino)-5- (3- (3-nitrobenzyl)ureido)bicyclo[2.2.1]heptane-2-carboxamide (50.70 mg; 0.11 mmol) in methanol (20.00 mL) to afford desired aniline (32 mg, 67.3%). LC/MS [method B, retention time 1.1 min; m/z 448.25 (M+1)].

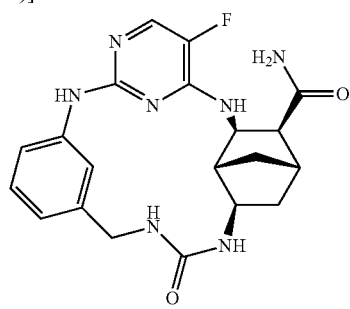

Example 54

The ring-closing step was performed as described for the synthesis of Example 24 with (1S,2S,3R,4R,5R)-5-({[(3-aminobenzyl)amino]carbonyl}amino)-3-[(2-chloro-5-fluoropyrimidin-4-yl)-amino]bicyclo[2.2.1]heptane-2-carboxamide (30.00 mg; 0.07 mmol) to afford desired macrocycle of Example 54 (10.1 mg, 36.7%).
LC/MS [method B, retention time 0.72 min; m/z 412.25 (M+1)].

Example 55

(1R,2S,3R,4R,5R)-3-(2-chloro-5-fluoropyrimidin-4-ylamino)-5-((2-(4-methyl-piperazin-1-yl)-5-nitrobenzylamino)methyl)bicyclo[2.2.1]heptane-2-carboxamide

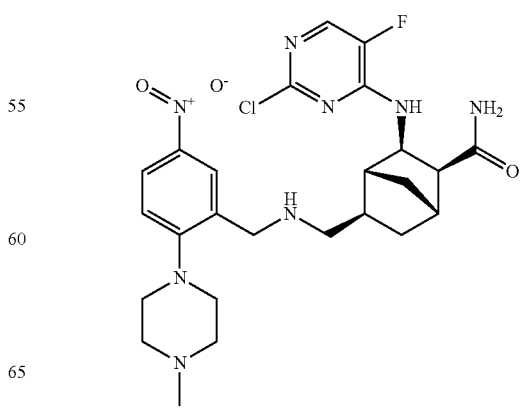

To a solution of (1R,2S,3R,4R,5R)-5-(aminomethyl)-3-[(2-chloro-5-fluoropyrimidin-4-yl)amino]bicyclo[2.2.1]heptane-2-carboxamide (125.20 mg; 0.40 mmol) in methanol was added 2-(4-methylpiperazin-1-yl)-5-nitrobenzaldehyde (246.63 µl; 0.40 mmol). The reaction was stirred at room temperature for 15 hours. To the solution was added sodium triacetoxyborohydride (253.71 mg; 1.20 mmol) with a drop of acetic acid and the reaction stirred at room temperature for 4 hours. Crude mixture was purified by flash chromatography to afford the desired product (115.4 mg, 52.9%). LC/MS [method B, retention time 0.62 min; m/z 547.25 (M+1)].

(1R,2S,3R,4R,5R)-5-((5-amino-2-(4-methylpiperazin-1-yl)benzylamino)methyl)-3-(2-chloro-5-fluoropyrimidin-4-ylamino)bicyclo[2.2.1]heptane-2-carboxamide

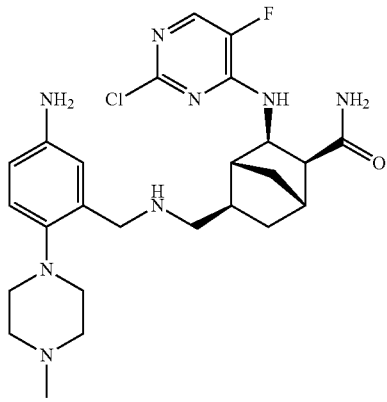 [SMILES: CN1CCN(c2ccc(N)cc2CNC[C@@H]2C[C@@H]3C[C@H]2[C@@H](Nc2nc(Cl)ncc2F)[C@H]3C(N)=O)CC1]

The nitro group reduction step was performed as described for Procedure B with (1R,2S,3R,4R,5R)-3-[(2-chloro-5-fluoropyrimidin-4-yl)amino]-5-({[2-(4-methylpiperazin-1-yl)-5-nitrobenzyl]amino}methyl)bicyclo[2.2.1]heptane-2-carboxamide (45.00 mg; 0.08 mmol) to afford desired aniline (42.5 mg, 39.9%).

LC/MS [method B, retention time 0.57 min; m/z 517.25 (M+1)].

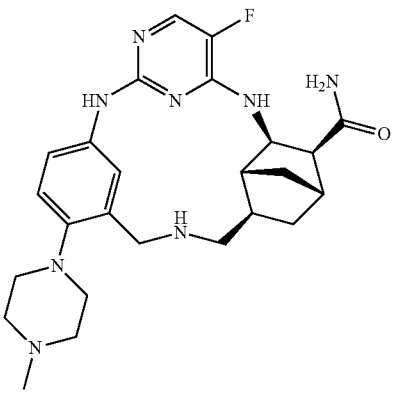 [SMILES: CN1CCN(c2ccc3cc2CNC[C@@H]2C[C@@H]4C[C@H]2[C@@H](Nc2nc(ncc2F)N3)[C@H]4C(N)=O)CC1]

Example 55

The ring-closing step was performed as described for the synthesis of Example 24 with (1R,2S,3R,4R,5R)-5-({[5-amino-2-(4-methylpiperazin-1-yl)benzyl]amino}-methyl)-3-[(2-chloro-5-fluoropyrimidin-4-yl)amino]bicyclo[2.2.1]heptane-2-carboxamide (59.20 mg; 0.11 mmol) to afford desired macrocycle of Example 55 (13.7 mg, 24.9%). LC/MS [method B, retention time 0.56 min; m/z 481.25 (M+1)].

Example 56

3-(4-methylpiperazin-1-yl)-5-nitrobenzene-1-sulfonyl chloride

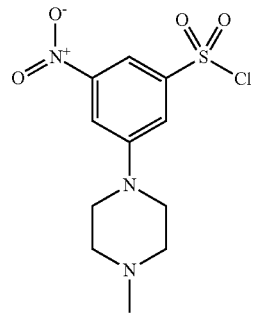 [SMILES: CN1CCN(c2cc([N+](=O)[O-])cc(S(=O)(=O)Cl)c2)CC1]

Into a dry round bottom flask equipped with stirbar was added 3-(4-methylpiperazin-1-yl)-5-nitroaniline (0.50 g; 2.12 mmol) in one portion to a mixture of concentrated hydrochloric acid (0.71 ml; 23.28 mmol) and glacial acetic acid (0.21 ml; 3.70 mmol). The round bottom flask is then lowered into a dry ice-ethanol bath, and upon the solution reaching −10° C., a 10M solution of aqueous sodium nitrite (0.07 ml; 2.33 mmol) was added dropwise at a rate such that the temperature remained less than −5° C. After the sodium solution was completely added, the mixture was stirred for 45 minutes. While diazotination is being completed, a saturated solution of oxosulfane oxide in acetic acid was prepared by bubbling sulfur dioxide gas (50.00 ml; 100.00 V) in glacial acetic acid (2 mL). Copper(1) chloride (24.75 mg; 0.25 mmol) was then added to the sulfur dioxide solution, while sulfur dioxide continues to bubble into solution. After 30 minutes, the flask containing the stirring saturated sulfur dioxide solution was placed into an ice bath, and cooled to 10° C., where upon the diazotization reaction mixture was added in portions over a 30-min period. The combined mixture was stirred, cold, until no gas evolution was observed. The spent reaction mixture was concentrated to a residue under high vacuum, and used without further purification.

(1R,2S,3R,4R,5R)-3-(2-chloro-5-fluoropyrimidin-4-ylamino)-5-((3-(4-methyl-piperazin-1-yl)-5-nitrophenylsulfonamido)methyl)bicyclo[2.2.1]heptane-2-carboxamide

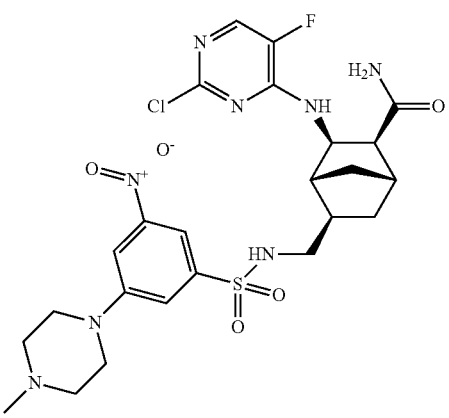

Into a scintillation vial equipped with a stirbar was dissolved (1R,2S,3R,4R,5R)-5-(aminomethyl)-3-[(2-chloro-5-fluoropyrimidin-4-yl)amino]bicyclo[2.2.1]heptane-2-carboxamide (100.00 mg; 0.32 mmol) in THF. To the solution was added triethylamine (0.06 ml; 0.41 mmol) and 3-(4-methylpiperazin-1-yl)-5-nitro-benzenesulfonyl chloride (132.49 mg; 0.41 mmol). The vial was sealed and allowed to stir at room temperature for 15 minutes. The concentrated reaction mixture was purified via Prep RP-HPLC using a gradient of 0-30% methanol in 0.1% trifluoroacetic acid (aq) solution over 30 minutes to afford desired product (119 mg, 62.6%). LC/MS [method B, retention time 2.3 min; m/z 597.25 (M+1)].

(1R,2S,3R,4R,5R)-5-((3- amino-5-(4-methylpiperazin-1-yl)phenylsulfonamido)-methyl)-3- (2-chloro-5-fluoropyrimidin-4-ylamino)bicyclo[2.2.1]heptane-2-carboxamide

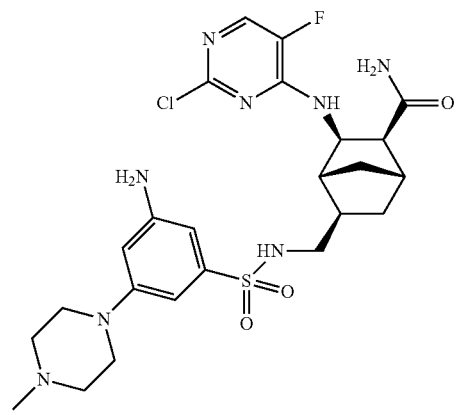 [SMILES: CN1CCN(c2cc(N)cc(S(=O)(=O)NC[C@@H]3C[C@@H]4C[C@H]3[C@@H](Nc3nc(Cl)ncc3F)[C@H]4C(N)=O)c2)CC1]

The nitro group reduction step was performed as described for Procedure B with (1R,2S,3R,4R,5R)-3-[(2-chloro-5-fluoropyrimidin-4-yl)amino]-5-[({[3-(4-methylpiperazin-1-yl)-5-nitrophenyl]sulfonyl}amino)methyl]bicyclo[2.2.1]heptane-2-carboxamide (119.00 mg; 0.2 mmol) to afford desired aniline. LC/MS [method B, retention time 1.1 min; m/z 567.25 (M+1)].

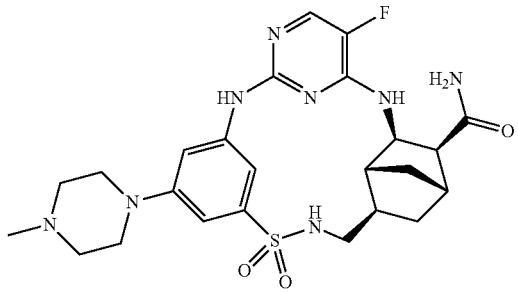 [SMILES: CN1CCN(c2cc3cc(c2)S(=O)(=O)NC[C@@H]2C[C@@H]4C[C@H]2[C@@H](Nc2nc(ncc2F)N3)[C@H]4C(N)=O)CC1]

Example 56

The ring-closing step was performed as described for the synthesis of Example 24 with (1R,2S,3R,4R,5R)-5-[({[3-amino -5-(4-methylpiperazin-1-yl)phenyl]sulfonyl}- amino) methyl]-3-[(2-chloro-5-fluoropyrimidin -4-yl)amino]bicyclo [2.2.1]heptane-2-carboxamide (99.00 mg; 0.17 mmol) to afford desired macrocycle of Example 56 (6.3 mg, 6.8%). LC/MS [method B, retention time 0.65 min; m/z 531.25 (M+1)].

Example 57

(1R,2S,3R,4R,5R)-3-(2-chloro-5-fluoropyrimidin-4-ylamino)-5-((2-(4-methyl-piperazin-1-yl)-5-nitrobenzamido)methyl)bicyclo[2.2.1]heptane-2-carboxamide

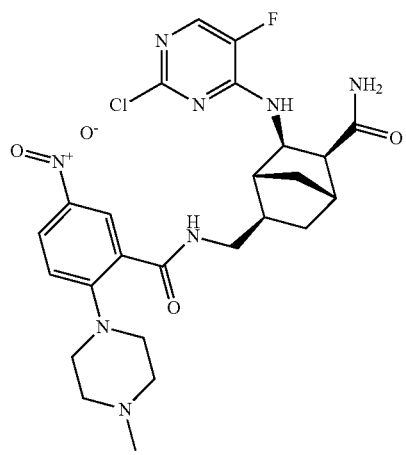

The amidation reaction was performed as described for Procedure C with (1R,2S,3R,4R,5R)-5-(aminomethyl)-3-[(2-chloro -5-fluoropyrimidin-4-yl)amino]bicyclo[2.2.1]heptane-2-carboxamide (93.25 mg; 0.30 mmol) and 2-(4-methylpiperazin-1-yl)-5-nitrobenzoic acid (90.19 mg; 0.34 mmol) to afford the desired product (120.6 mg, 72%). LC/MS [method B, retention time 0.63 min; m/z 561.25 (M+1)].

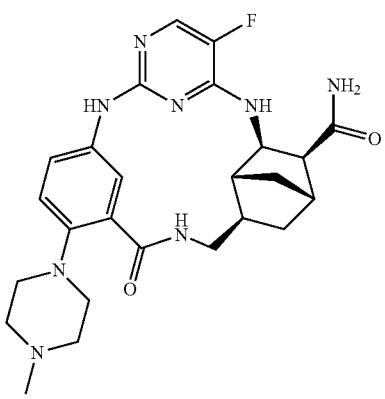 [SMILES: CN1CCN(c2ccc3cc2C(=O)NC[C@@H]2C[C@@H]4C[C@H]2[C@@H](Nc2nc(ncc2F)N3)[C@H]4C(N)=O)CC1]

Example 57

The nitro group reduction and concomitant cyclization steps were performed as described for Procedure A with (1R,2S,3R,4R)-3-[(2-chloro-5-fluoropyrimidin-4-yl) amino]-6-({[(3-nitrophenyl)amino]carbonyl}amino)bicyclo [2.2.1]heptane-2-carboxamide (100.50 mg; 0.22 mmol) to afford the compound of Example 57 (3 mg, 3.5%). LC/MS [method B, retention time 0.56 min; m/z 495.25 (M+1)].

Example 58

(1R,2S,3R,4R,5R)-3- (2-chloro-5-fluoropyrimidin-4-ylamino)-5- ((2- (2- (4-methyl-piperazin-1-yl)-5-nitrophenyl)acetamido)methyl)bicyclo[2.2.1]heptane-2-carboxamide

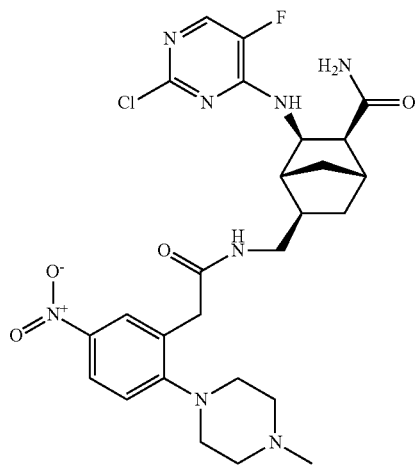 [SMILES: CN1CCN(c2ccc([N+](=O)[O-])cc2CC(=O)NC[C@@H]2C[C@@H]3C[C@H]2[C@@H](Nc2nc(Cl)ncc2F)[C@H]3C(N)=O)CC1]

The amidation reaction was performed as described for Procedure C with [2-(4-methylpiperazin-1-yl)-5-nitrophenyl]acetic acid (106.82 mg; 0.38 mmol) and (1R,2S,3R,4R,5R)-5-(aminomethyl)-3-[(2-chloro -5-fluoropyrimidin-4-yl)-amino]bicyclo[2.2.1]heptane-2-carboxamide (60.00 mg; 0.19 mmol) to afford the desired product (96 mg, 87%). LC/MS [method B, retention time 2.9 min; m/z 575.25 (M+1)].

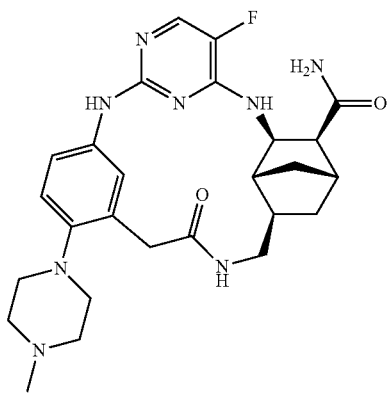 [SMILES: CN1CCN(c2ccc3cc2CC(=O)NC[C@@H]2C[C@@H]4C[C@H]2[C@@H](Nc2nc(ncc2F)N3)[C@H]4C(N)=O)CC1]

Example 58

The nitro group reduction and concomitant cyclization steps were performed as described for Procedure A with (1R,2S,3R,4R)-3-[(2-chloro-5-fluoropyrimidin-4-yl) amino]-6-( {[(3-nitrophenyl)amino]carbonyl}amino)bicyclo [2.2.1]heptane-2-carboxamide (100.50 mg; 0.22 mmol) to afford the compound of Example 58 (2.1 mg, 2.4%). LC/MS [method B, retention time 0.59 min; m/z 509.25 (M+1)].

Example 59

(1R,2S,3R,4R,5R)-3-(2-chloro-5-fluoropyrimidin-4-ylamino)-5-((2-hydroxy-2-(3-nitrophenyl)ethylamino)methyl)bicyclo[2.2.1]heptane-2-carboxamide

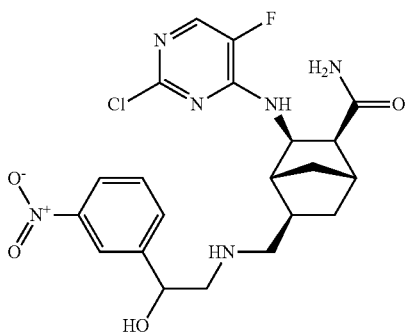 [SMILES: NC(=O)[C@H]1[C@@H]2C[C@@H](CNCC(O)c3cccc([N+](=O)[O-])c3)[C@@H](C2)[C@H]1Nc1nc(Cl)ncc1F]

In a flask, dicaesium carbonate (181.73 mg; 0.56 mmol) was added to a stirring solution of 2-(3-nitrophenyl)oxirane (40.53 mg; 0.25 mmol) and (1R,2S,3R,4R,5R)-5-(aminomethyl)-3-[(2-chloro -5-fluoropyrimidin-4-yl)amino]bicyclo [2.2.1]heptane-2-carboxamide (70.00 mg; 0.22 mmol) in dimethylformamide (3.00 ml). The reaction was stirred at room temperture for 8 days. The reaction mixture was then concentrated and purified by prep RP-HPLC to afford the desired product (5.6 mg, 5.2% yield). LC/MS [method B, retention time 2.3 min; m/z 479.25 (M+1)].

(1R,2S,3R,4R,5R)-5-((2-(3-aminophenyl)-2-hydroxyethylamino)methyl)-3-(2-chloro-5-fluoropyrimidin-4-ylamino)bicyclo[2.2.1]heptane-2-carboxamide

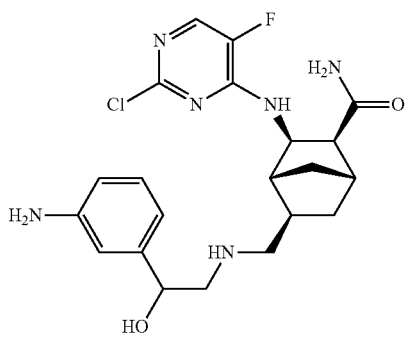 [SMILES: NC(=O)[C@H]1[C@@H]2C[C@@H](CNCC(O)c3cccc(N)c3)[C@@H](C2)[C@H]1Nc1nc(Cl)ncc1F]

The nitro group reduction step was performed as described for Procedure B with (1R,2S,3R,4R,5R)-3-[(2-chloro-5-fluoropyrimidin-4-yl)amino]-5- ({[2-hydroxy-2-(3-nitrophenyl) ethyl]amino}methyl)bicyclo[2.2.1]heptane-2-carboxamide (5.00 mg; 0.01 mmol) to afford desired aniline. LC/MS [method B, retention time 0.57 min; m/z 449.25 (M+1)].

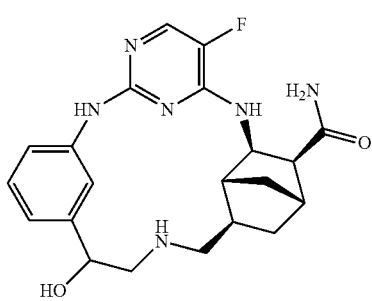 [SMILES: NC(=O)[C@H]1[C@@H]2C[C@H]3CNCC(O)c4cccc(c4)Nc4ncc(F)c(n4)N[C@@H]1[C@@H]3C2]

Example 59

The ring-closing step was performed as described for the synthesis of Example 24 with (1R,2S,3R,4R,5R)-5-({[2-(3-aminophenyl)-2-hydroxyethyl]amino}methyl)-3-[(2-chloro-5-fluoropyrimidin-4-yl)amino]bicyclo[2.2.1]heptane-2-carboxamide (4.6 mg; 0.02 mmol; 1.00 eq.) to afford desired macrocycle of Example 59 (1.8 mg, 43.9%). LC/MS [method B, retention time 0.6 min; m/z 413.25 (M+1)].

Example 60

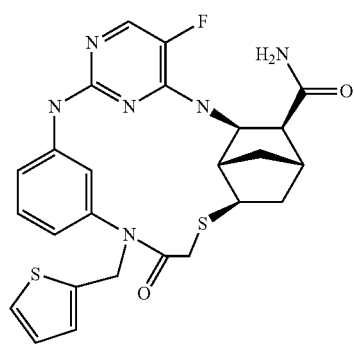 [SMILES: NC(=O)[C@H]1[C@H]2C[C@H]3[C@H]1Nc1nc(ncc1F)Nc1cccc(c1)N(Cc1cccs1)C(=O)CS[C@@H]3C2]

Example 60

To the mixture of S-{(1S,2R,4S,5S,6S)-5-(aminocarbonyl)-6-[(2-chloro-5-fluoropyrimidin-4-yl)amino]bicyclo[2.2.1]hept-2-yl}ethanethioate (200.00 mg; 0.56 mmol; 1.00 eq.) in MeOH, was added 0.15 mL MeONa (30% in MeOH). The mixture was stirred for 30 min at room temperature. 2-chloro-N-(3-nitrophenyl)-N-(2-thienylmethyl)acetamide (173.21 mg; 0.56 mmol; 1.00 eq.) was added to the mixture and stirred overnight. The mixture was co-rotavapped with silica gel. The resulting residue was applied to a silica gel column (0% to 100% hexane/ethyl actate, then 0% to 50% MeOH/ethyl acetate) to afford 2-chloro-N-(3-nitro-phenyl)-N-thiophen-2-ylmethyl-acetamide.

The nitro reduction and the following ring-closing steps were performed as described for the synthesis of Example 24 with 2-chloro-N-(3-nitro-phenyl)-N-thiophen-2-ylmethyl-acetamide to afford macrocycle of Example 60. LC/MS [method A, retention time 4.8 min; m/z 525.1 (M+1)].

Example 61

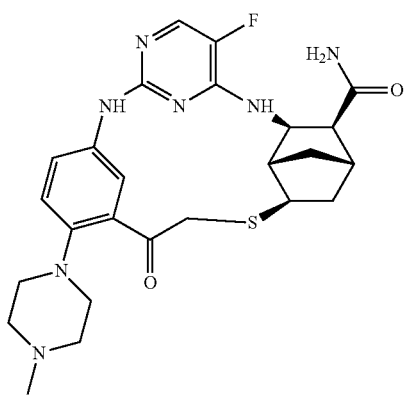 [SMILES: CN1CCN(c2ccc3cc2C(=O)CS[C@@H]2C[C@@H]4C[C@H]2[C@@H](Nc2nc(ncc2F)N3)[C@H]4C(N)=O)CC1]

Example 61

This compound was prepared as the procedure for Example 60 using 2-Chloro-1-[2-(4-methyl-piperazin-1-yl)-5-nitro-phenyl]-ethanone. LC/MS [method A, retention time 1.7 min; m/z 512.2 (M+1)].

Examples 62 and 63

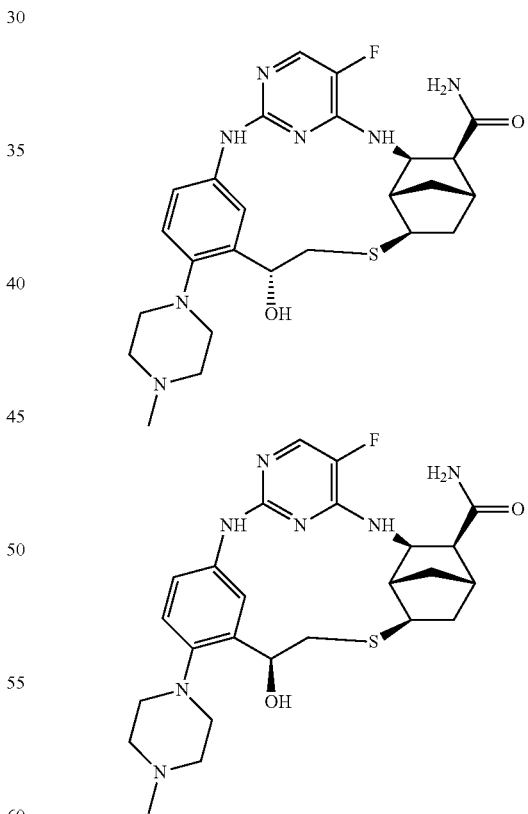

Example 62

Example 63

To a solution of macrocycle of Example 61 (25 mg, 0.05 mmol) in THF-EtOH (1:1, 2 mL) was added sodium borohydride (7.39 mg; 0.20 mmol; 4.00 eq.) under nitrogen. The mixture was stirred at rt overnight. 9 mg of NaBH4 was added and the mixture was stirred for another 4 h. It was quenched with water and neutralized to pH7. The mixture was concentrated and the resulting residue was purified by prep HPLC to afford of Example 62 (6 mg) and of Example 63 (6 mg). The stereochemistry of the OH group was not determined. Example 62: LC/MS [method A, retention time 4.3 min; m/z 514.1 (M+1)]. Example 53: LC/MS [method A, retention time 3.2 min; m/z 514.1 (M+1)].

Example 64

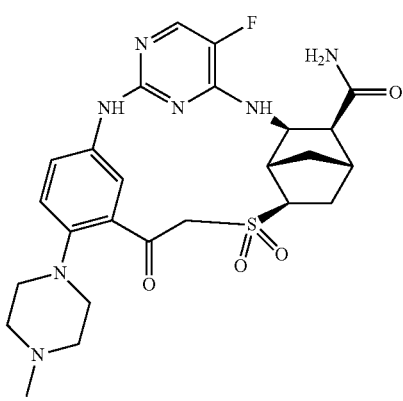 [SMILES: CN1CCN(c2ccc3cc2C(=O)CS(=O)(=O)[C@@H]2C[C@@H]4C[C@H]2[C@@H](Nc2nc(ncc2F)N3)[C@H]4C(N)=O)CC1]

Example 64

To a solution of compound of Example 61 (20 mg, 0.04 mmol) in dry DCM (2 mL) under nitrogen, was added MCPBA (11 mg, 70%, 0.04 mmol). The mixture was stirred at RT for 4 h. The reaction was quenched with aqueous NaSO$_3$. The mixture was concentrated and purified by prep HPLC to afford the compound of Example 64 (5 mg). LC/MS [method A, retention time 0.33 min; m/z 544.2 (M+1)].

Example 65

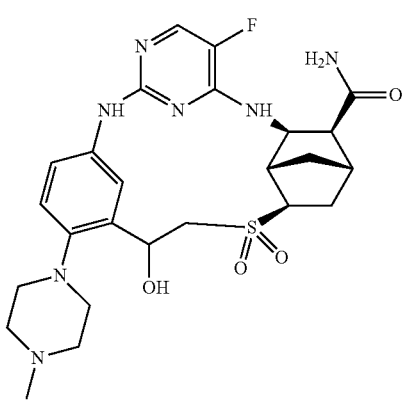 [SMILES: CN1CCN(c2ccc3cc2C(O)CS(=O)(=O)[C@@H]2C[C@@H]4C[C@H]2[C@@H](Nc2nc(ncc2F)N3)[C@H]4C(N)=O)CC1]

Example 65

To a solution of compound of Example 64 (4 mg, 0.01 mmol) in EtOH-THF (1:1, 1 mL) was added NaBH$_4$ (1.1 mg, 0.03 mmol). The mixture was stirred at RT for 20 min The reaction was quenched with water and neutralized to pH 7. The mixture was purified by prep HPLC to afford compound of Example 65 (2 mg).

LC/MS [method A, retention time 0.35 min; m/z 546.5 [M+1].

Example 66

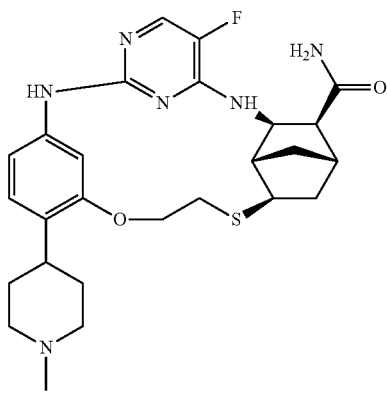 [SMILES: CN1CCC(c2ccc3cc2OCCS[C@@H]2C[C@@H]4C[C@H]2[C@@H](Nc2nc(ncc2F)N3)[C@H]4C(N)=O)CC1]

Example 66

Using 2-(1-Methyl-piperidin-4-yl)-5-nitrophenol as starting material, compound of Example 66 was prepared as the similar procedure in the preparation of Example 22. LC/MS [method B, retention time 1.6 min; m/z 513.0 (M+1)].

Example 67

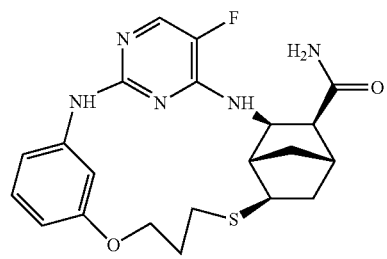 [SMILES: NC(=O)[C@H]1[C@H]2C[C@H]3[C@H]1Nc1nc(ncc1F)Nc1cccc(c1)OCCCS[C@@H]3C2]

Example 67

This compound was prepared as described in the synthesis of Example 21 above. LC/MS [method A, retention time 4.6 min; m/z 430.1 (M+1)].

Example 68

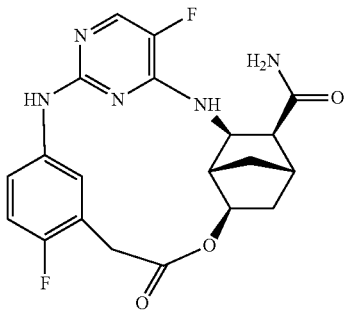 [SMILES: NC(=O)[C@H]1[C@H]2C[C@H]3[C@H]1Nc1nc(ncc1F)Nc1ccc(F)c(c1)CC(=O)O[C@@H]3C2]

Example 68

A Schlenk tube charged with [Rh(COD)Cl]₂ (175 mg, 0.35 mmol) and (S,S)-DBPP (311 mg, 0.71 mmol) was evacuated/flushed with N2. THF (58 mL) was added, followed by (1S,2S,3R,4R)-3-[(2-chloro-5-fluoropyrimidin-4-yl)amino]bicyclo[2.2.1]hept-5-ene-2-carboxamide (5.00 g; 17.69 mmol; 1.00 eq.) in 2 mL THF. The mixture was cooled to −78 c, stirred for 10 min, and CatBH (1,3,2-benzodioxaborole, 3.77 mL, 35 mmol) was added to the solution. The mixture was stirred at −78 C for 30 min and then stirred at rt for 2 days. The mixture cooled to 0 C, 20 mL of ethanol was added, followed by 20 mL of 3M NaOH and 20 mL of 30% H₂O₂. The mixture was stirred at r.t. for 6 h. Then it was diluted with 170 mL of 1 M NaOH solution. The mixture was extracted with EtOAc (3×), washing with 1 M NaOH, H₂O and brine. After concentration of the organic layer and the resulting residue was applied to flash column to afford two adduct (3:1 ratio);

(1S,2S,3R,4S,5R)-3-(2-chloro-5-fluoropyrimidin-4-ylamino)-5-hydroxybicyclo[2.2.1]heptane-2-carboxamide (612 mg, 12%) and (1R,2S,3R,4R,6S)-3-(2-chloro-5-fluoropyrimidin-4-ylamino)-6-hydroxybicyclo[2.2.1]heptane-2-carboxamide (222 mg, 4%).

To a solution of 1S,2S,3R,4S,5R)-3-(2-Chloro-5-fluoropyrimidin-4-ylamino)-5-hydroxy-bicyclo[2.2.1]heptane-2-carboxylic acid amide (50 mg, 0.17 mmol) and 2-(2-fluoro-5-nitrophenyl)acetic acid (33 mg, 0.17 mmol) in pyridine (1 mL), was added ((1R,4 S)-7,7-dimethyl-2-oxobicyclo[2.2.1]heptan-1-yl)methanesulfonic acid (2.7 mg, 0.01 mol) and N,N'-methanediylidenedicyclohexanamine (38 mg, 0.18 mmol). The mixture was stirred at rt for 3 days. It was then concentrated and the resulting residue was applied to silica gel chromatography to afford (1S,2R,4S,5S,6R)-5-carbamoyl-6-(2-chloro-5-fluoropyrimidin-4-ylamino)bicyclo[2.2.1]heptan-2-yl 2-(2-fluoro-5-nitrophenyl)acetate (12 mg).

The nitro reduction step was performed in H-cube using Pt cartridge. The flow rate in 1 mL/min at 35° C.

Macrocyclization was performed as followed: To a 50 mL rbf was charged with TFA and dry CAN. It was heated to reflux under nitrogen. (1S,2R,4S,5S,6R)-5-(aminocarbonyl)-6-[(2-chloro-5-fluoropyrimidin-4-yl)amino]bicyclo[2.2.1]hept-2-yl (5-amino-2-fluorophenyl)acetate (10.00 mg; 0.02 mmol; 1.00 eq.) in ACN(2 ml) was added dropwise with syringe bump over 1 hours. The mixture was refluxed overnight. The mixture was concentrated and the crude was purified by Preparative HPLC to afford compound of Example 68. LC/MS [method B, retention time 4.1 min; m/z 416.3 (M+1)].

Example 69

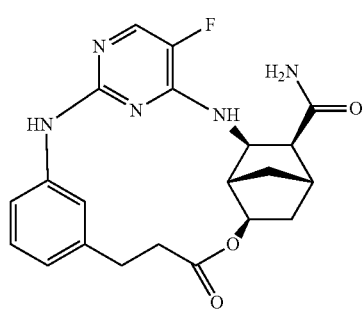 [SMILES: NC(=O)[C@H]1[C@H]2C[C@H]3[C@H]1Nc1nc(ncc1F)Nc1cccc(c1)CCC(=O)O[C@@H]3C2]

Example 69

The compound was prepared in the similar procedure as described for Example 68. LC/MS [method B, retention time 3.6 min; m/z 412.0 (M+1)].

Example 70

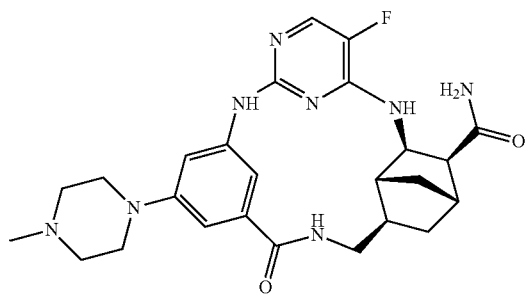 [SMILES: CN1CCN(c2cc3cc(c2)C(=O)NC[C@@H]2C[C@@H]4C[C@H]2[C@@H](Nc2nc(ncc2F)N3)[C@H]4C(N)=O)CC1]

Example 70

This compound was prepared in the similar procedure as described for Example 58. LC/MS [method A, retention time 0.3 min; m/z 495.2 (M+1)].

Example 71

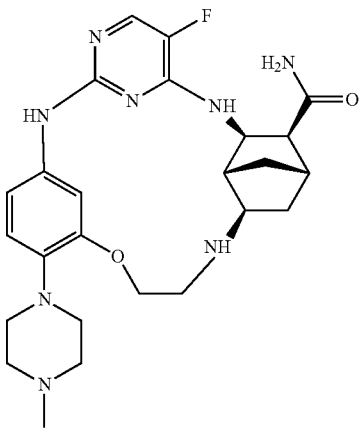 [SMILES: CN1CCN(c2ccc3cc2OCCN[C@@H]2C[C@@H]4C[C@H]2[C@@H](Nc2nc(ncc2F)N3)[C@H]4C(N)=O)CC1]

Example 71

To a solution of 2-[2-(4-methylpiperazin-1-yl)-5-nitrophenoxy]ethyl 4-methylbenzenesulfonate (319.65 mg; 0.73 mmol; 1.10 eq.) and the (1S,2S,3R,4R,5R)-5-amino-3-[(2-chloro-5-fluoropyrimidin-4-yl)amino]bicyclo[2.2.1]heptane-2-carboxamide (200.00 mg; 0.67 mmol; 1.00 eq.) in DMF, was added dicaesium carbonate (543.51 mg; 1.67 mmol; 2.50 eq.) The mixture was stirred at RT overnight. The mixture was concentrated and purified by silica gel chromatography to afford (1S,2S,3R,4R,5R)-3-(2-chloro-5-fluoropyrimidin-4-ylamino)-5-(2-(2-(4-methylpiperazin-1-yl)-5-nitrophenoxy)ethylamino)bicyclo[2.2.1]heptane-2-carboxamide (110 mg).

The nitro reduction and the following macrocyclization steps were performed as described for Example 22 to afford the compound of Example 71. LC/MS [method A, retention time 0.37 min; m/z 497.0 (M+1)].

Example 72

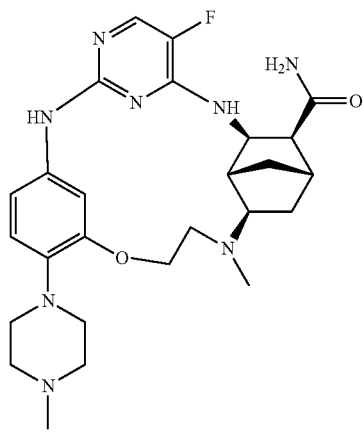 [SMILES: CN1CCN(c2ccc3cc2OCCN(C)[C@@H]2C[C@@H]4C[C@H]2[C@@H](Nc2nc(ncc2F)N3)[C@H]4C(N)=O)CC1]

Example 72

To s solution of (1S,2S,3R,4R,5R)-3-[(2-chloro-5-fluoro-pyrimidin-4-yl)amino]-5-({2-[2-(4-methylpiperazin-1-yl)-5-nitrophenoxy]ethyl}amino)bicyclo[2.2.1]heptane-2-carboxamide (100.00 mg; 0.18 mmol; 1.00 eq.) in meOH was added a 37% formaldehyde (13.22 µl; 0.18 mmol; 1.00 eq.) The mixture was stirred at rt overnight. The mixture was co-rotavapped with toluene 4 times to remove water. The mixture was re-suspended in MeOH and added sodium triacetoxyborohydride (151 mg, 4 eq.). The mixture was stirred for 1 h at rt. It was concentrated and purify by prep HPLC to afford (1S,2S,3R,4S,5R)-3-(2-chloro-5-fluoropyrimidin-4-ylamino)-5-(methyl(2-(2-(4-methylpiperazin-1-yl)-5-nitrophenoxy)ethyl)amino)bicyclo[2.2.1]heptane-2-carboxamide (113 mg).

The nitro reduction and the following macrocyclization steps were performed as described for Example 22 to afford the compound of Example 72. LC/MS [method A, retention time 0.38 min; m/z 511.0 (M+1)].

Example 73

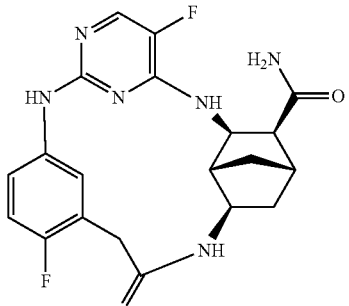

Example 73

This compound was prepared in the similar procedure as described for Example 58. LC/MS [method A, retention time 0.64 min; m/z 415.4 (M+1)].

Example 74

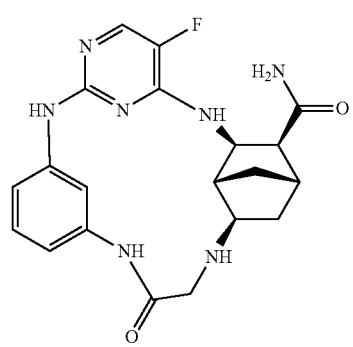 [SMILES: NC(=O)[C@H]1[C@H]2C[C@H]3[C@H]1Nc1nc(ncc1F)Nc1cccc(c1)NC(=O)CN[C@@H]3C2]

Example 74

To a solution of 2-chloro-N-(3-nitrophenyl)acetamide (43 mg, 0.20 mmol) and the (1S,2S,3R,4R,5R)-5-amino-3-[(2-chloro-5-fluoropyrimidin-4-yl)-amino]bicyclo[2.2.1]heptane-2-carboxamide (60 mg; 0.20 mmol) in dry MeCN, was added dicaesium carbonate (163 mg; 0.50 mmol) The mixture was stirred at RT overnight. The mixture was concentrated and purified by silica gel chromatography to afford (1S,2S,3R,4R)-3-(2-chloro-5-fluoropyrimidin-4-ylamino)-5-(2-(3-nitrophenylamino)-2-oxoethylamino)bicyclo[2.2.1]heptane-2-carboxamide.

The nitro reduction and the following macrocyclization steps were performed as described for Example 71 to afford the compound of Example 74. LC/MS [method B, retention time 5.3 min; m/z 412.2 (M+1)].

Example 75

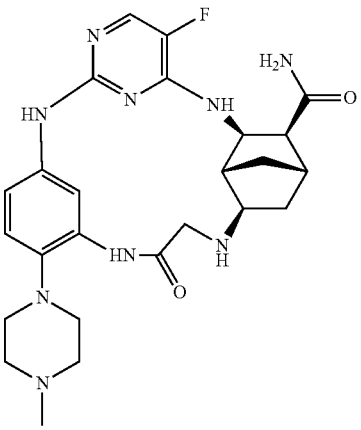 [SMILES: CN1CCN(c2ccc3cc2NC(=O)CN[C@@H]2C[C@@H]4C[C@H]2[C@@H](Nc2nc(ncc2F)N3)[C@H]4C(N)=O)CC1]

Example 75

Chloroacetyl chloride (218.81 µl; 2.75 mmol) was dissovled in dry DCM and it was cooled to 0° C. N,N-diethylethanamine (442.44 µl; 3.17 mmol; 1.50 eq.) was added, followed by addition of 2-(4-methylpiperazin-1-yl)-5-nitroaniline (500.00 mg; 2.12 mmol; 1.00 eq.). The mixture was stirred at 0° C. for 1 h and allowed to warm to rt for 1 h. Solution turned from clear to cloudy yellow. LC/MS indicated a complete conversion. The mixture was concentrated and dried to afford crude 2-chloro-N-(2-(4-methylpiperazin-1-yl)-5-nitrophenyl)acetamide. The adduct was proceed to next step without further purification.

The following N-alkylation, nitro reduction and macrocyclization were performed as described for Example 74 to afford the compound of Example 75. LC/MS [method A, retention time 0.39 min; m/z 510.4 (M+1)].

Example 76

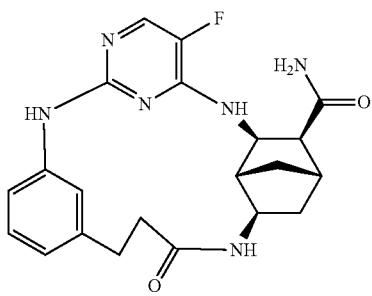 [SMILES: NC(=O)[C@H]1[C@H]2C[C@H]3[C@H]1Nc1nc(ncc1F)Nc1cccc(c1)CCC(=O)N[C@@H]3C2]

Example 76

This compound was prepared in the similar procedure as described for Example 58. LC/MS [method A, retention time 0.77 min; m/z 411.2 (M+1)].

Example 77

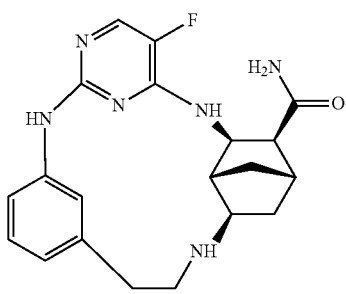 [SMILES: NC(=O)[C@H]1[C@H]2C[C@H]3[C@H]1Nc1nc(ncc1F)Nc1cccc(c1)CCN[C@@H]3C2]

Example 77

In a seal tube, dicaesium carbonate (543.51 mg; 1.67 mmol; 2.50 eq.) was added to stirring solution of 2-(3-nitrophenyl)ethyl 4-methylbenzenesulfonate (235.87 mg; 0.73 mmol; 1.10 eq.) and the (1S,2S,3R,4R,5R)-5-amino-3-[(2-chloro-5-fluoropyrimidin-4-yl)amino]bicyclo[2.2.1]heptane-2-carboxamide (200.00 mg; 0.67 mmol; 1.00 eq.) in DMF. The mixture was stirred at rt over weekend. The mixture was concentrated and the resulting residue was applied to silica gel chromatograph to affore pure adduct (1S,2S,3R,4R,5R)-3-(2-chloro-5-fluoropyrimidin-4-ylamino)-5-(3-nitrophenethylamine)bicyclo[2.2.1]heptane-2-carboxamide (50 mg).

The following nitro reduction and macrocyclization were performed as described for Example 74 to afford the compound of Example 77. LC/MS [method A, retention time 0.42 min; m/z 308.0 (M+1)].

Example 78

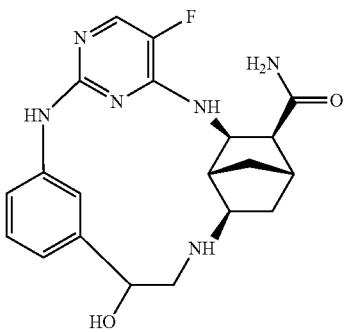 [SMILES: NC(=O)[C@H]1[C@H]2C[C@H]3[C@H]1Nc1nc(ncc1F)Nc1cccc(c1)C(O)CN[C@@H]3C2]

Example 78

In a round bottom flask, diaesium carbonate (543.51 mg; 1.67 mmol; 2.50 eq.) was added to stirring solution of 2-(3-nitrophenyl)oxirane (121.22 mg; 0.73 mmol; 1.10 eq.) and the (1S,2S,3R,4R,5R)-5-amino-3-[(2-chloro-5-fluoropyrimidin-4-yl)amino]bicyclo[2.2.1]heptane-2-carboxamide (200.00 mg; 0.67 mmol; 1.00 eq.) in DMF. The mixture was stirred at rt overnight. The mixture was concentrated and the resulting residue was applied to silica gel chromatograph to afford pure adduct (1S,2S,3R,4R,5R)-3-(2-chloro-5-fluoropyrimidin-4-ylamino)-5-(2-hydroxy-2-(3-nitrophenyl)ethylamino)bicyclo[2.2.1]heptane-2-carboxamide (50 mg, 16%).

The following nitro reduction and macrocyclization were performed as described for Example 74 to afford the compound of Example 78. LC/MS [method A, retention time 0.40 min; m/z 399.2 (M+1)].

Example 79

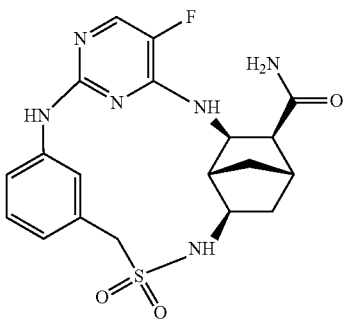 [SMILES: NC(=O)[C@H]1[C@H]2C[C@H]3[C@H]1Nc1nc(ncc1F)Nc1cccc(c1)CS(=O)(=O)N[C@@H]3C2]

Example 79

To a scintillation vial equipped with a stir bar was dissolved (1S,2S,3R,4R,5R)-5-amino-3-[(2-chloro-5-fluoropyrimidin-4-yl)amino]bicyclo[2.2.1]heptane-2-carboxamide (200.00 mg; 0.67 mmol; 1.00 eq.) in THF (3.00 ml). To the solution was added triethylamine (212.74 μl; 1.53 mmol; 2.30 eq.) and 3-nitro-alpha-toluenesulfonyl chloride (188.68 mg; 0.80 mmol; 1.20 eq.). The vial was sealed and allowed to stir at room temperature for 2 h. The mixture was concentrated and the resulting residue was applied to silica gel chromatograph to afford (1S,2S,3R,4S,5R)-3-(2-chloro-5-fluoropyrimidin-4-ylamino)-5-((3-nitrophenyl)methylsulfonamido)bicyclo[2.2.1]heptane-2-carboxamide.

The following nitro reduction and macrocyclization were performed as described for Example 74 to afford the compound of Example 79. LC/MS [method A, retention time 0.35 min; m/z 433.6 (M+1)].

Example 80

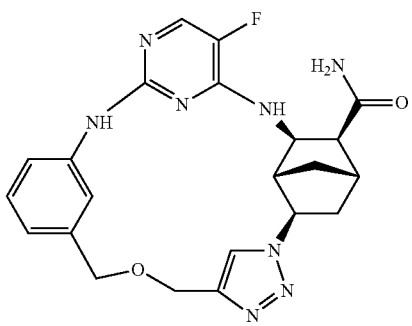 [SMILES: NC(=O)[C@H]1[C@H]2C[C@H]3[C@H]1Nc1nc(ncc1F)Nc1cccc(c1)COCc1cn(nn1)[C@@H]3C2]

Example 80

To (3-nitrophenyl)methanol (384.91 µl; 3.27 mmol; 1.00 eq.) in THF under $N_2$ was added hydridosodium (261.18 mg; 6.53 mmol; 2.00 eq.). After stirring for 10 min, 3-bromoprop-1-yne (727.36 µl; 6.53 mmol; 2.00 eq.) was added into the mixture. The mixture was stirred at rt overnight. The mixture was concentrated and the resulting residue was applied to silica gel chromatograph to afford 1-nitro-3-((prop-2-ynyloxy)methyl)benzene (782 mg, 80%).

To a solution of (1S,2S,3R,4S,5R)-5-azido-3-(2-chloro-5-fluoropyrimidin-4-ylamino)bicyclo[2.2.1]heptane-2-carboxamide (150 mg, 0.46 mmol) and 1-nitro-3-((prop-2-ynyloxy)methyl)benzene (88 mg, 0.46 mmol) in Water-EtOH-tBuOH (3:2:5, 2 mL) and EtOAc (1 mL), was added $CuSO_4$ (0.5 M, 0.1 mL) and copper powder (3 mg). The mixture was stirred at rt for 10 days. The mixture was concentrated and the resulting residue was applied to silica gel chromatograph to afford (1S,2S,3R,4S,5R)-3-(2-chloro-5-fluoropyrimidin-4-ylamino)-5-(4-((3-nitrobenzyloxy)methyl)-1H-1,2,3-triazol-1-yl)bicyclo[2.2.1]heptane-2-carboxamide.

The following nitro reduction and macrocyclization were performed as described for Example 74 to afford the compound of Example 80. LC/MS [method A, retention time 4.2 min; m/z 451.1 (M+1)].

Example 81

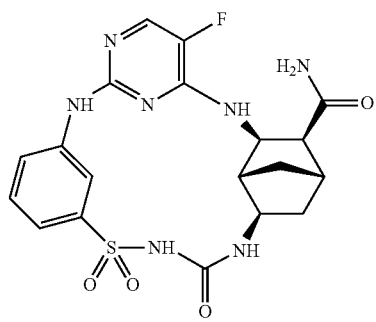 [SMILES: NC(=O)[C@H]1[C@H]2C[C@H]3[C@H]1Nc1nc(ncc1F)Nc1cccc(c1)S(=O)(=O)NC(=O)N[C@@H]3C2]

Example 81

To a solution of TFA salt of (1S,2S,3R,4R,5R)-5-amino-3-(2-chloro-5-fluoropyrimidin-4-ylamino)bicyclo[2.2.1] heptane-2-carboxamide (226 mg, 0.55 mmol) and ethyl 3-nitrophenylsulfonylcarbamate (164.8 mg, 0.60 mmol) in dioxane (2 mL), was added triethylamine (0.11 mL, 0.82 mmol). The mixture was refluxed for 5 h. The mixture was cooled and concentrated. The resulting residue was applied to silica gel chromatograph to afford (1S,2S,3R,4R,5R)-3-(2-chloro-5-fluoropyrimidin-4-ylamino)-5-(3-(3-nitrophenylsulfonyl)ureido)bicyclo[2.2.1]heptane-2-carboxamide (150 mg, 52%). The following nitro reduction and macrocyclization were performed as described for Example 74 to afford the compound of Example 81. LC/MS [method A, retention time 3.1 min; m/z 462.1 (M+1)].

Example 82

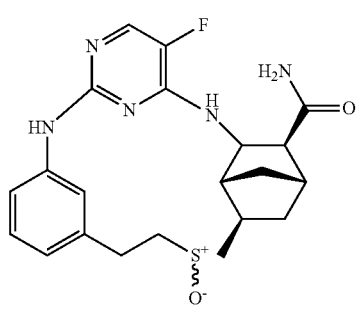

Example 82

To a solution of the final product compound of Example 18 (50 mg, 0.12 mmol) in DCM at −78° C. under nitrogen, was added MCPBA (70%, 299 mg, 1.2 mmol). The mixture was stirred at −78° C. for 3 hours. The reaction was quenched with saturated $NaHSO_3$ solution and the mixture was concentrated. The resulting residue was applied to the reverse-phase prep HPLC to afford the desired adduct (3 mg). LC/MS [method A, retention time 3.33 min; m/z 416.1 (M+1)].

Biochemical Enzyme Assays for Aurora Activity

Numerous models exist for identification of a signal transduction pathway and detection of interactions among various signal transduction pathways. For example, there are the cell culture models of Khwaja et al., *EMBO*, (1997), 16: 2783-93, and transgenic animal models of White et al., *Oncogene*, (2001), 20: 7064-7072. For the identification of certain stages in the signal transduction cascade, interacting compounds can be utilized in order to modulate the signal (see, for example, Stephens et al., *Biochemical J.*, (2000), 351:95-105). The compounds according to the invention also can be used as reagents for testing kinase-dependent signal transduction pathways in animals and/or cell culture models, or in the clinical diseases mentioned herein.

Measurement of kinase activity is a technique well known to a person skilled in the art. Generic test systems for the determination of kinase activity that employ substrates (as for example, histone found in Alessi et al., *FEBS Lett.* (1996), 399(3): 333-338) or basic myelin protein are described in the literature (see for example, Campos-Gonzalez, R. and Glenney, Jr., J. R., *J. Biol. Chem.* (1992), 267:14535).

For the identification of kinase inhibitors, various assay systems are available. In scintillation proximity assay (Sorg et al., *J. of Biomolecular Screening*, (2002), 7:11-19) and flash-plate assay, the radioactive phosphorylation of a protein or peptide as substrate with ATP is measured. In the presence of an inhibitory compound, a decreased radioactive signal, or none at all, is detectable. Homogeneous time-resolved fluorescence resonance energy transfer (HTR-FRET) and fluorescence polarisation (FP) technologies also are suitable as assay methods (Sills et al., *J. of Biomolecular Screening*, (2002) 191-214), as is the use of a caliper test known to those skilled in the art.

Other non-radioactive ELISA assay methods use specific phospho-antibodies (phospho-ABs). The phospho-AB binds only to the phosphorylated substrate. This binding then can be detected by chemiluminescence using a second peroxidase-conjugated anti-sheep antibody (Ross et al., *Biochem. J.* (2002)).

The Aurora and other kinase assays described here were performed on two Caliper Life Sciences systems, the LC3000 and the Desktop Profiler. These provide data on enzyme activity via measurement of the relative amounts of phosphorylated or unphosphorylated fluorescently labelled substrate peptide at the end of an enzymatic reaction. These different states of peptide are resolved by applying a potential difference across the sample. The presence of a charged phosphate group on the product (as opposed to the substrate) causes a different peptide mobility between the two peptides. This is visualized by excitation of a fluorescent label on the substrate and product peptides and represented as peaks within the analysis software.

LC3000 Method

For example, in order to measure inhibitor activity of Aurora A inhibitors in the Caliper Life Sciences LC3000, a TTP Mosquito liquid handling instrument was used to place 0.25 ml of an appropriate concentration of inhibitor in 100% DMSO (for a dose response curve calculation) into each well of a 384-well plate. To this reaction components were added to a final volume of 25 µl:

0.067 ng/µl GST-Aurora A (Carna Biosciences 05-101. N-terminal GST fusion with full length Aurora A (1-403 amino acids), accession number NP_940835.1).
 15 µM ATP (Fluka, 02055)
 1 mM DTT (Sigma, D0632)
 1 mM MgC12 (Sigma, M1028)
 1 µM substrate peptide (sequence FITC-LRRASLG-(CONH2), synthesized by Tufts Peptide Synthesis service.
 100 mM HEPES pH 7.5 (Calbiochem, 391338)
 0.015% Brij-35 (Sigma, B4184)

The reaction was incubated for 90 min at 25° C., and then stopped by the addition of 70 µl of Stop buffer (100 mM HEPES pH 7.5, 0.015% Brij-35, 10 mM EDTA (Sigma, E7889)).

The plate was read on a Caliper LC 3000 in an Off-Chip mobility shift assay format, using the following parameters for a 12-sipper chip: screening pressure −1.8 psi, upstream voltage −2700, downstream voltage −1000. These conditions cause unphosphorylated substrate and phosphorylated product peptide to resolve as separate peaks allowing direct measurement of percentage of conversion of substrate to product. The percent conversion was plotted against concentration of inhibitor to produce a sigmoidal dose response curve, from which an $IC_{50}$ was calculated using XLFit for Microsoft Excel.

Desktop Profiler Method

The Desktop Profiler utilizes the same principal as the LC 3000 for calculating percentage conversion of a substrate to product. Caliper Life Sciences provided proprietary flash frozen pre-made 384 well plates containing selected kinases. Each column in the 384 well plate contained a particular selected kinase. A second plate, the 'substrate plate' contained a mix of fluorescently labeled peptide substrate and ATP. These were arranged in columns so that transfer for substrate plate to enzyme plate provided the correct enzyme with the correct substrate/ATP concentration.

Compounds were added to a thawed enzyme plate in the desired format, in single concentrations. Reactions were initiated by transfer of the ubstrate/ATP mix from the substrate plate. The enzyme plate was incubated for 90 mins at 25o C. The reaction was stopped by addition of 70 m.1 of Stop Buffer (100 mM HEPES pH 7.5, 0.015% Brij-35, 10 mM EDTA (Sigma, E7889)).

Plates were read in a manner identical to that of the LC3000, and the ratio between substrate and product peaks provided the activity of the enzyme in that well. This was best represented by a plate heat map which colors each well by percent inhibition as compared to positive and negative controls (no inhibitors and no ATP respectively).

The results of compounds tested on either of these two systems are given in Table 1 below:

TABLE 1

Aurora A Kinase and Aurora B Kinase Inhibition by Certain Macrocycles

| Structure | Enzyme Activity | |
| --- | --- | --- |
| | Aurora A $IC_{50}$ (nM) | Aurora B $IC_{50}$ (nM) |
| 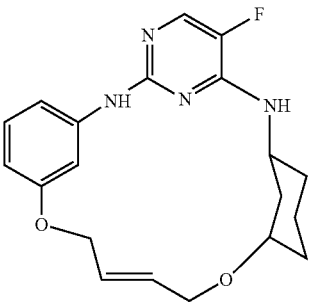 [SMILES: Fc1cnc2nc1NC1CCCC(C1)OC/C=C/COc1cccc(c1)N2] | ++ | ++ |

TABLE 1-continued
Aurora A Kinase and Aurora B Kinase Inhibition by Certain Macrocycles
| | | |
|---|---|---|
| 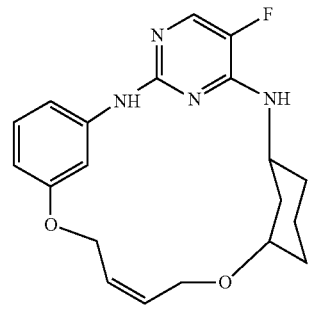 [SMILES: Fc1cnc2nc1NC1CCCC(C1)OC/C=C\COc1cccc(c1)N2] | ++ | ++ |
| 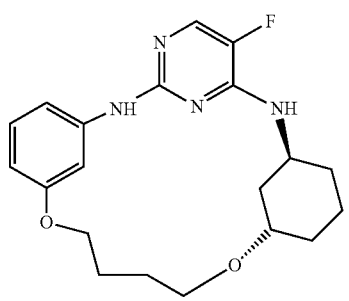 | +++ | |
| 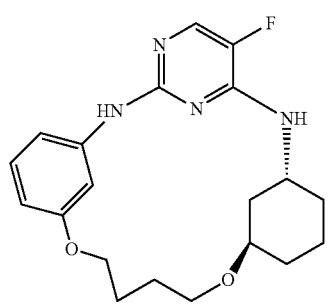 [SMILES: Fc1cnc2nc1N[C@@H]1CCC[C@H](C1)OCCCCOc1cccc(c1)N2] | ++ | |
| 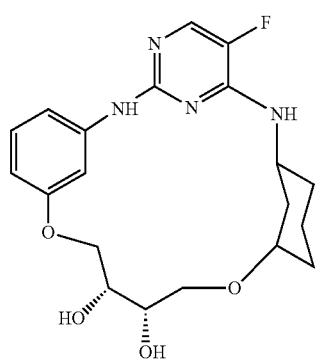 [SMILES: O[C@@H]1COc2cccc(c2)Nc2ncc(F)c(n2)NC2CCCC(C2)OC[C@@H]1O] | ++ | |

TABLE 1-continued
Aurora A Kinase and Aurora B Kinase Inhibition by Certain Macrocycles
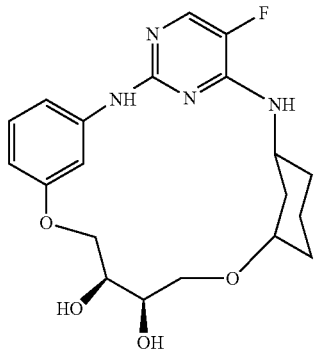 [SMILES: O[C@@H]1COC2CCCC(C2)Nc2nc(ncc2F)Nc2cccc(c2)OC[C@@H]1O]  ++
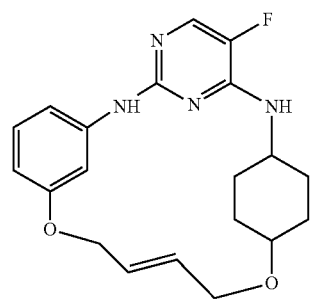 [SMILES: Fc1cnc2nc1NC1CCC(CC1)OC/C=C/COc1cccc(c1)N2]  ++
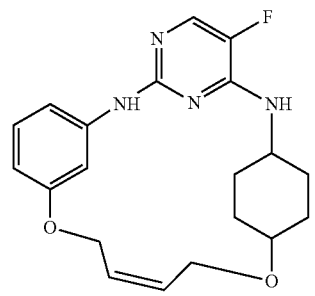 [SMILES: Fc1cnc2nc1NC1CCC(CC1)OC/C=C\COc1cccc(c1)N2]  ++  ++++
| | Enzyme Activity | | Kinase Inhibition Profile (not incl. Aurora) # kinases hit/# kinases tested |
| --- | --- | --- | --- |
| Structure | Aurora A IC$_{50}$ (nM) | Aurora B IC$_{50}$ (nM) | (where "hit" means >79% inhibition) in μM concentration units |
|  | ++ | ++ | 0/36 at 1 uM; 12/255 at 10 uM |

TABLE 1-continued

Aurora A Kinase and Aurora B Kinase Inhibition by Certain Macrocycles

| Structure | Aurora A | Aurora B | |
|---|---|---|---|
| | + | + | 0/36 at 1 uM |
| | + | + | 1/36 at 1 uM |
| | ++ | ++ | 0/36 at 1 uM |
| | +++ | | |
| | +++ | | |

TABLE 1-continued

Aurora A Kinase and Aurora B Kinase Inhibition by Certain Macrocycles

| | Enzyme Activity | | Cellular Activity | | Kinase Inhibition Profile (not incl. Aurora) #kinases hit/# kinases tested (where "hit" |
|---|---|---|---|---|---|
| | Aurora A IC$_{50}$ (nM) | Aurora B IC$_{50}$ (nM) | A549 IC$_{50}$ (nM) | MiaPaca2 IC$_{50}$ (nM) | means >79% inhibition) in µM concentration units |
| (structure) | +++ | | | | |
| (structure) | + | + | +++ | +++ | 14/36 at 1 µM; 18/74 at 1 µM |
| (structure) | + | + | +++ | +++ | 2/36 at 1 µM |
| (structure) | + | | ++ | ++ | |
| (structure) | + | + | +++ | +++ | |

TABLE 1-continued
Aurora A Kinase and Aurora B Kinase Inhibition by Certain Macrocycles
| | | | | | |
|---|---|---|---|---|---|
| 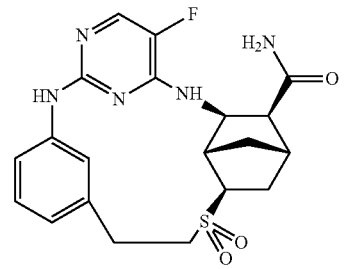 [SMILES: NC(=O)[C@H]1[C@H]2C[C@H]3[C@H]1Nc1nc(ncc1F)Nc1cccc(c1)CCS(=O)(=O)[C@@H]3C2] | + | + | +++ | +++ | |
| 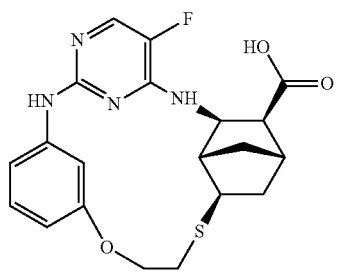 [SMILES: O=C(O)[C@H]1[C@H]2C[C@H]3[C@H]1Nc1nc(ncc1F)Nc1cccc(c1)OCCS[C@@H]3C2] | + | + | ++++ | ++++ | 8/36 at 10 μM |
| 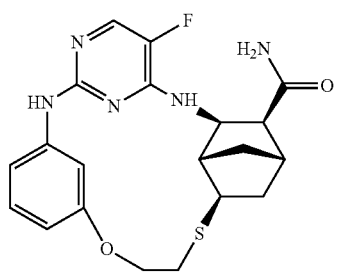 [SMILES: NC(=O)[C@H]1[C@H]2C[C@H]3[C@H]1Nc1nc(ncc1F)Nc1cccc(c1)OCCS[C@@H]3C2] | + | + | +++ | +++ | 11/36 at 1 μM |
| 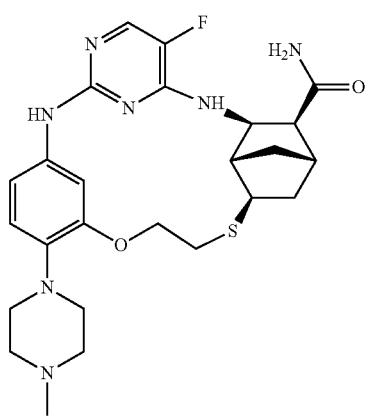 [SMILES: CN1CCN(c2ccc3cc2OCCS[C@@H]2C[C@@H]4C[C@H]2[C@@H](Nc2nc(ncc2F)N3)[C@H]4C(N)=O)CC1] | + | + | ++ | ++ | 12/51 at 1 μM |
| 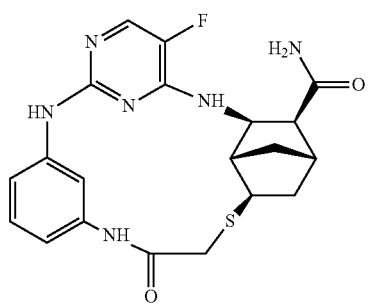 [SMILES: NC(=O)[C@H]1[C@H]2C[C@H]3[C@H]1Nc1nc(ncc1F)Nc1cccc(c1)NC(=O)CS[C@@H]3C2] | + | + | ++ | ++ | 12/36 at 1 |

TABLE 1-continued

Aurora A Kinase and Aurora B Kinase Inhibition by Certain Macrocycles

| Structure | | | | | |
|---|---|---|---|---|---|
| | + | + | ++ | ++ | 13/36 at 1 μM |
| | + | ++ | ++++ | ++++ | 12/38 at 1 μM |
| | + | + | ++++ | ++++ | |
| | ++ | ++ | +++ | +++= | |

TABLE 1-continued

Aurora A Kinase and Aurora B Kinase Inhibition by Certain Macrocycles

| Structure | | | | |
|---|---|---|---|---|
| [structure 1] | + | + | +++ | +++ |
| [structure 2] | +++ | | ++++ | ++++ |
| [structure 3] | ++ | | | |
| [structure 4] | + | ++ | ++++ | ++++ |
| [structure 5] | ++ | | ++++ | ++++ |

TABLE 1-continued
Aurora A Kinase and Aurora B Kinase Inhibition by Certain Macrocycles
| | | | | | |
|---|---|---|---|---|---|
| 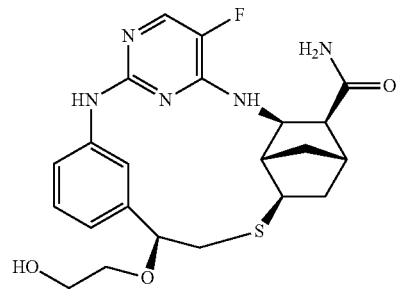 [SMILES: NC(=O)[C@H]1[C@H]2C[C@H]3[C@H]1Nc1nc(ncc1F)Nc1cccc(c1)[C@H](OCCO)CS[C@@H]3C2] | + | | +++ | +++ | |
| 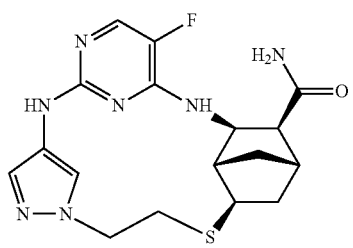 [SMILES: NC(=O)[C@H]1[C@H]2C[C@H]3[C@H]1Nc1nc(ncc1F)Nc1cnn(c1)CCS[C@@H]3C2] | + | | | | |
| 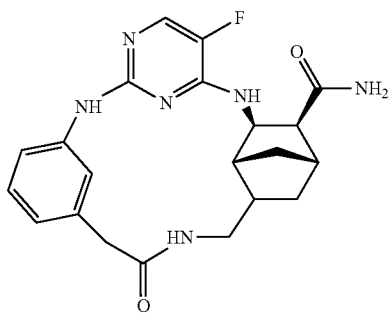 [SMILES: NC(=O)[C@H]1[C@@H]2CC3CNC(=O)Cc4cccc(c4)Nc4ncc(F)c(n4)N[C@@H]1[C@@H]3C2] | + | | | | |
| 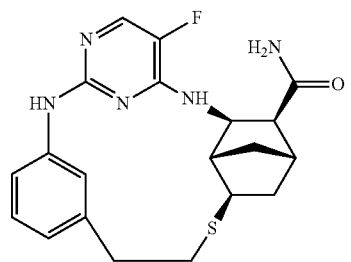 [SMILES: NC(=O)[C@H]1[C@H]2C[C@H]3[C@H]1Nc1nc(ncc1F)Nc1cccc(c1)CCS[C@@H]3C2] | + | + | +++ | +++ | 8/36 at 1 μM, 9/74 at 1 μM |
| 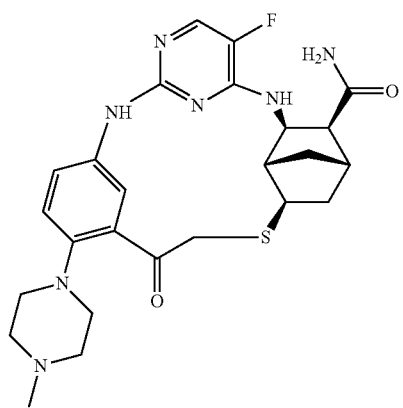 [SMILES: CN1CCN(c2ccc3cc2C(=O)CS[C@@H]2C[C@@H]4C[C@H]2[C@@H](Nc2nc(ncc2F)N3)[C@H]4C(N)=O)CC1] | + | | +++ | +++ | |

TABLE 1-continued

Aurora A Kinase and Aurora B Kinase Inhibition by Certain Macrocycles

| Structure | | | | | |
|---|---|---|---|---|---|
| (structure) | + | + | ++ | ++ | 0/76 at 1 μM |
| (structure) | + | + | ++ | ++ | |
| (structure) | + | + | + | + | 121/267 at 1 μM |
| (structure) | + | + | + | + | 121/267 at 1 μM |

TABLE 1-continued
Aurora A Kinase and Aurora B Kinase Inhibition by Certain Macrocycles
| | | | | |
|---|---|---|---|---|
| 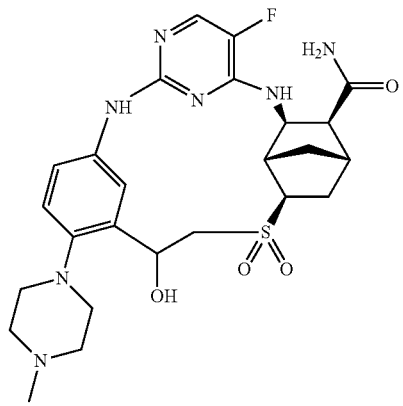 [SMILES: CN1CCN(c2ccc3cc2C(O)CS(=O)(=O)[C@@H]2C[C@@H]4C[C@H]2[C@@H](Nc2nc(ncc2F)N3)[C@H]4C(N)=O)CC1] | + | + | | |
| 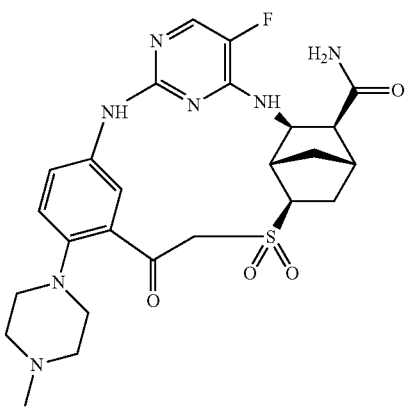 [SMILES: CN1CCN(c2ccc3cc2C(=O)CS(=O)(=O)[C@@H]2C[C@@H]4C[C@H]2[C@@H](Nc2nc(ncc2F)N3)[C@H]4C(N)=O)CC1] | + | +++ | | |
| 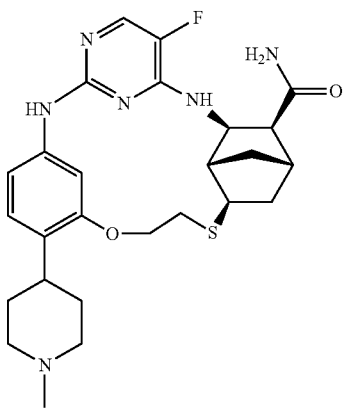 [SMILES: CN1CCC(c2ccc3cc2OCCS[C@@H]2C[C@@H]4C[C@H]2[C@@H](Nc2nc(ncc2F)N3)[C@H]4C(N)=O)CC1] | + | + | ++ | ++ |
| 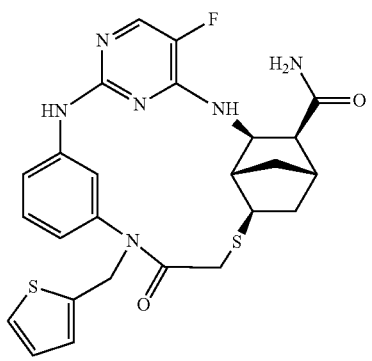 [SMILES: NC(=O)[C@H]1[C@H]2C[C@H]3[C@H]1Nc1nc(ncc1F)Nc1cccc(c1)N(Cc1cccs1)C(=O)CS[C@@H]3C2] | ++ | +++ | | |

TABLE 1-continued
Aurora A Kinase and Aurora B Kinase Inhibition by Certain Macrocycles
| | | | | |
|---|---|---|---|---|
| 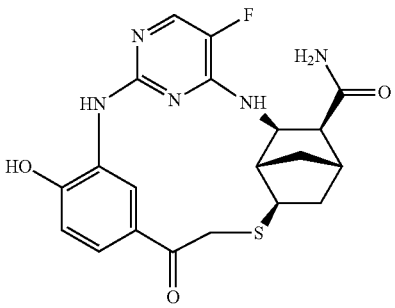 [SMILES: NC(=O)[C@H]1[C@H]2C[C@H]3[C@H]1Nc1nc(ncc1F)Nc1cc(ccc1O)C(=O)CS[C@@H]3C2] | +++ | +++ | | |
| 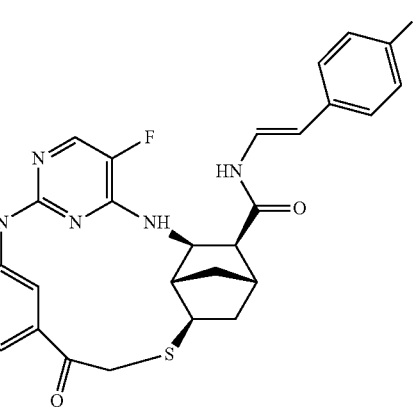 | ++ | ++ | ++++ | ++++ |
| 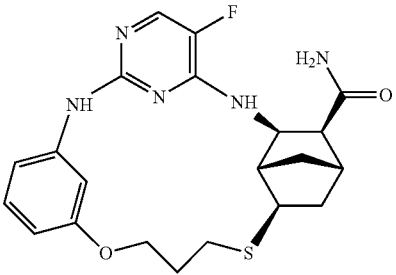 [SMILES: NC(=O)[C@H]1[C@H]2C[C@H]3[C@H]1Nc1nc(ncc1F)Nc1cccc(c1)OCCCS[C@@H]3C2] | + | + | +++ | +++ |
| 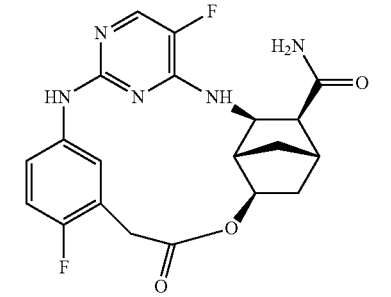 [SMILES: NC(=O)[C@H]1[C@H]2C[C@H]3[C@H]1Nc1nc(ncc1F)Nc1ccc(F)c(c1)CC(=O)O[C@@H]3C2] | +++ | +++ | | |
|  | ++ | ++ | +++ | +++ |

TABLE 1-continued
Aurora A Kinase and Aurora B Kinase Inhibition by Certain Macrocycles
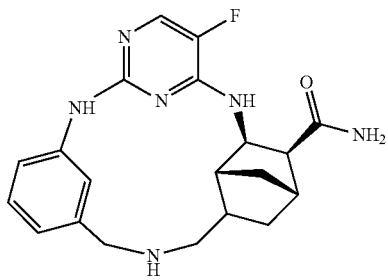 [SMILES: NC(=O)[C@H]1[C@@H]2CC3CNCc4cccc(c4)Nc4ncc(F)c(n4)N[C@@H]1[C@@H]3C2]   ++   +   +   +   1/50 at 1 μM
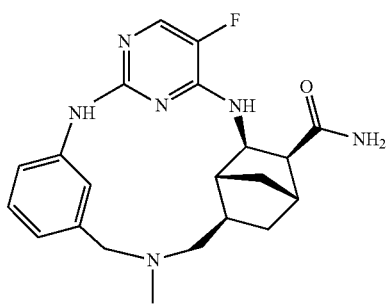 [SMILES: CN1Cc2cccc(c2)Nc2ncc(F)c(n2)N[C@@H]2[C@@H]3C[C@@H](C[C@H]3C1)[C@@H]2C(N)=O]   +++   +
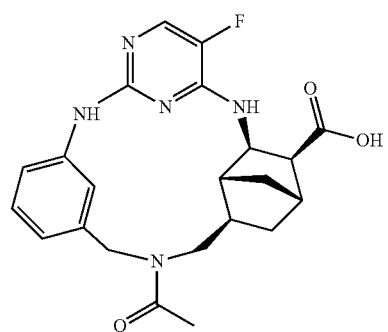 [SMILES: CC(=O)N1Cc2cccc(c2)Nc2ncc(F)c(n2)N[C@@H]2[C@@H]3C[C@@H](C[C@H]3C1)[C@@H]2C(=O)O]   +++   ++++
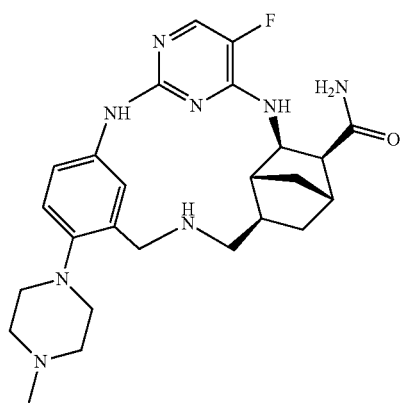 [SMILES: CN1CCN(c2ccc3cc2CNC[C@@H]2C[C@@H]4C[C@H]2[C@@H](Nc2nc(ncc2F)N3)[C@H]4C(N)=O)CC1]   ++   +

TABLE 1-continued
Aurora A Kinase and Aurora B Kinase Inhibition by Certain Macrocycles
| | | | | | |
|---|---|---|---|---|---|
| 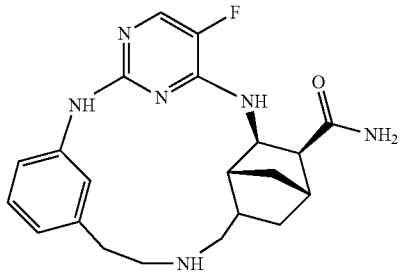 [SMILES: NC(=O)[C@H]1[C@@H]2CC3CNCCc4cccc(c4)Nc4ncc(F)c(n4)N[C@@H]1[C@@H]3C2] | ++ | + | ++ | ++ | 1/53 at 1 µM |
| 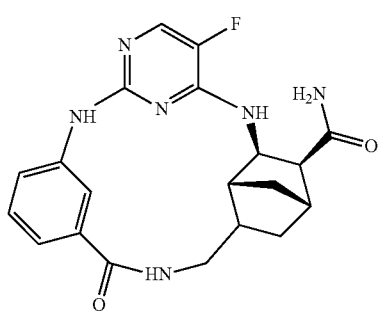 [SMILES: NC(=O)[C@H]1[C@@H]2CC3CNC(=O)c4cccc(c4)Nc4ncc(F)c(n4)N[C@@H]1[C@@H]3C2] | + | + | +++ | +++ | 1/76 at 1 µM |
| 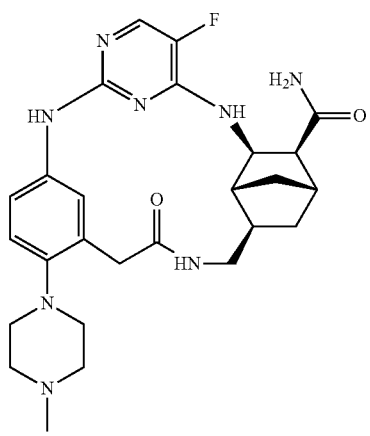 [SMILES: CN1CCN(c2ccc3cc2CC(=O)NC[C@@H]2C[C@@H]4C[C@H]2[C@@H](Nc2nc(ncc2F)N3)[C@H]4C(N)=O)CC1] | ++ | +++ | ++++ | +++ | 0/73 at 1 µM |
| 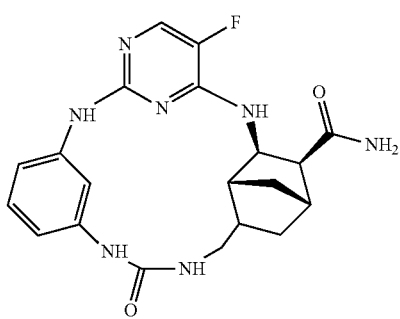 [SMILES: NC(=O)[C@H]1[C@@H]2CC3CNC(=O)Nc4cccc(c4)Nc4ncc(F)c(n4)N[C@@H]1[C@@H]3C2] | ++ | ++ | ++++ | +++ | 1/76 at 1 µM |

TABLE 1-continued

Aurora A Kinase and Aurora B Kinase Inhibition by Certain Macrocycles

| Structure | | | | | |
|---|---|---|---|---|---|
| (structure) | + | + | +++ | +++ | |
| (structure) | + | ++ | +++ | +++ | |
| (structure) | + | + | +++ | +++ | 1/76 at 1 μM |
| (structure) | ++ | ++ | ++++ | +++ | 0/73 at 1 μM |
| (structure) | + | | +++ | ++ | 14/264 at 1 μM |

TABLE 1-continued

Aurora A Kinase and Aurora B Kinase Inhibition by Certain Macrocycles

| Structure | | | | | |
|---|---|---|---|---|---|
| [structure] | +++ | +++ | | | |
| [structure] | + | + | ++++ | +++ | 2/73 at 1 μM |
| [structure] | ++ | | | | |
| [structure] | + | | | | |
| [structure] | ++ | ++ | | | |

TABLE 1-continued
Aurora A Kinase and Aurora B Kinase Inhibition by Certain Macrocycles
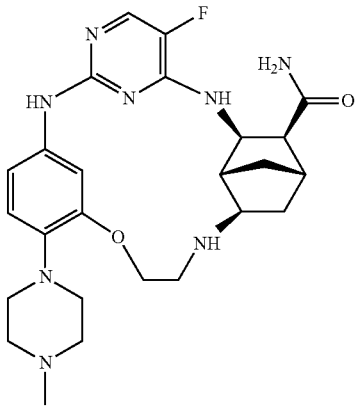 [SMILES: CN1CCN(c2ccc3cc2OCCN[C@@H]2C[C@@H]4C[C@H]2[C@@H](Nc2nc(ncc2F)N3)[C@H]4C(N)=O)CC1] ++ + ++ ++
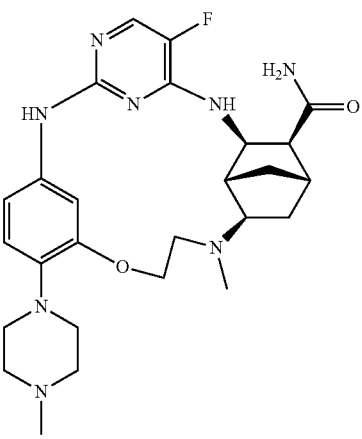 [SMILES: CN1CCN(c2ccc3cc2OCCN(C)[C@@H]2C[C@@H]4C[C@H]2[C@@H](Nc2nc(ncc2F)N3)[C@H]4C(N)=O)CC1] + +
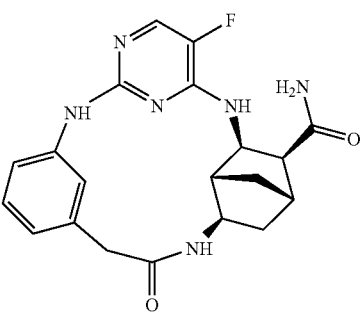 [SMILES: NC(=O)[C@H]1[C@H]2C[C@H]3[C@H]1Nc1nc(ncc1F)Nc1cccc(c1)CC(=O)N[C@@H]3C2] + +
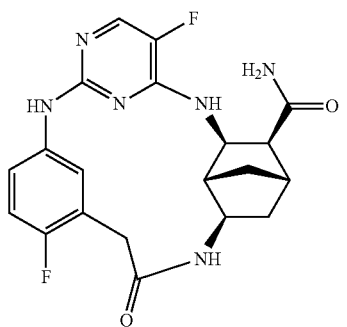 [SMILES: NC(=O)[C@H]1[C@H]2C[C@H]3[C@H]1Nc1nc(ncc1F)Nc1ccc(F)c(c1)CC(=O)N[C@@H]3C2] + + +++ +++

TABLE 1-continued
Aurora A Kinase and Aurora B Kinase Inhibition by Certain Macrocycles
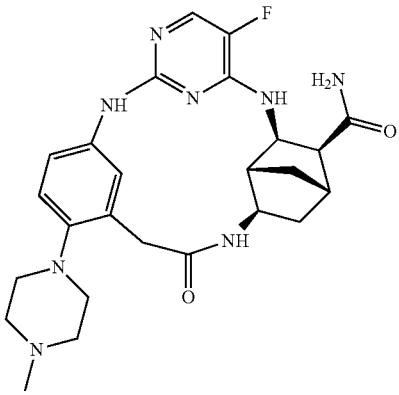 [SMILES: CN1CCN(c2ccc3cc2CC(=O)N[C@@H]2C[C@@H]4C[C@H]2[C@@H](Nc2nc(ncc2F)N3)[C@H]4C(N)=O)CC1]
\+ \+
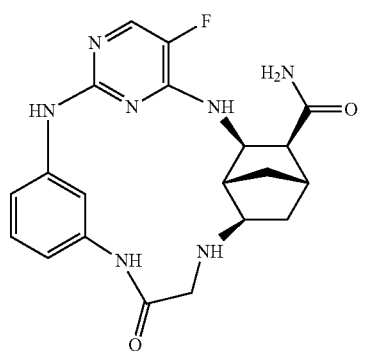 [SMILES: NC(=O)[C@H]1[C@H]2C[C@H]3[C@H]1Nc1nc(ncc1F)Nc1cccc(c1)NC(=O)CN[C@@H]3C2]
+++ ++
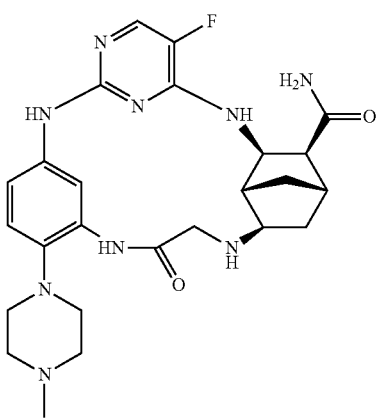 [SMILES: CN1CCN(c2ccc3cc2NC(=O)CN[C@@H]2C[C@@H]4C[C@H]2[C@@H](Nc2nc(ncc2F)N3)[C@H]4C(N)=O)CC1]
\+ \+ +++ +++
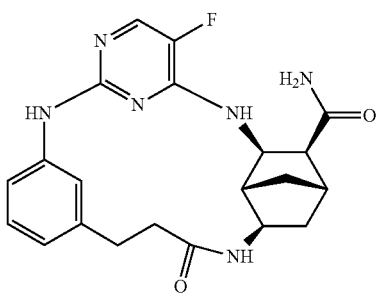 [SMILES: NC(=O)[C@H]1[C@H]2C[C@H]3[C@H]1Nc1nc(ncc1F)Nc1cccc(c1)CCC(=O)N[C@@H]3C2]
++ ++ +++ +++

TABLE 1-continued

Aurora A Kinase and Aurora B Kinase Inhibition by Certain Macrocycles

| Structure | | | | |
|---|---|---|---|---|
| (structure 1) | ++ | + | +++ | +++ |
| (structure 2) | ++ | + | +++ | +++ |
| (structure 3) | ++ | ++ | | |
| (structure 4) | + | | +++ | +++ |
| (structure 5) | ++ | | | |

TABLE 1-continued

Aurora A Kinase and Aurora B Kinase Inhibition by Certain Macrocycles

| Structure | | | | |
|---|---|---|---|---|
| [macrocycle with fluoropyrimidine, aniline, benzyl, urea, norbornane-carboxamide] | + | + | +++ | +++ |
| [macrocycle with fluoropyrimidine, aniline, benzyl carbamate, norbornane-carboxamide] | + | + | +++ | +++ |
| [macrocycle with fluoropyrimidine, N-methylpiperazinyl aniline, benzyl carbamate, norbornane-carboxamide] | + | + | ++ | ++ |

**IC$_{50}$ ranges are given as:
+ = 1-100 in nM
++ = 101-1000 nM
+++ = 1001-6250 nM
++++ = >6250 nM

TABLE 2

Inhibition of Other Kinases by Specific Compounds of the Invention

| | Example 18 IC$_{50}$ (nM) | Example 20 IC$_{50}$ (nM) | Example 27 IC$_{50}$ (nM) |
|---|---|---|---|
| Abl(T315I)(h) | | | + |
| FAK(h) | ++ | ++ | |
| IRAK4(h) | + | ++ | + |
| Pyk2(h) | ++ | ++ | |
| Ret(h) | +++ | ++ | + |
| Tie2(h) | +++ | ++ | ++ |

TABLE 3

Inhibition of Other Kinases by Specific Compounds of the Invention
At a Concentration of 1 μM (numbers shown are % inhibition)

| | Example 33 Compound D @ 1 μM | Example 10 Compound E @ 1 μM | | Example 22 Compound F @ 1 μM |
|---|---|---|---|---|
| AMPK | 76 | 38 | Abl(h) | −4 |
| BRSK2 | 81 | 26 | TrkA(h) | −1 |
| BTK | 37 | 2 | Yes(h) | 2 |
| CAMKI | 93 | 73 | Flt3(D835Y)(h) | 3 |
| CAMKKb | 81 | 73 | Ret(h) | 4 |
| CDK2/cyclin A | 60 | 94 | Aurora-A(h) | 5 |
| CHK1 | 98 | 73 | FGFR1(h) | 5 |
| CHK2 | 77 | 12 | Flt4(h) | 11 |
| CK1-delta | 85 | 92 | Lyn(h) | 12 |
| CK2 | 96 | 91 | Abl(T315I)(h) | 13 |
| CSK | 86 | 56 | TrkB(h) | 14 |
| DYRK1-alpha | 86 | 83 | cSRC(h) | 16 |
| DYRK3 | 99 | 78 | EphB2(h) | 16 |
| EF2K | 78 | 62 | Rsk1(h) | 23 |
| EphA2 | 81 | 25 | Flt3(h) | 24 |
| EphB3 | 54 | 4 | SIK(h) | 25 |
| FGFR1 | 74 | 10 | Pyk2(h) | 27 |
| GSK3-beta | 57 | 19 | Hck(h) | 28 |
| HIPK2 | 68 | 23 | FAK(h) | 30 |
| IGF1-R | 82 | 2 | Axl(h) | 40 |
| IKK-beta | 78 | 82 | KDR(h) | 41 |
| IKK-epsilon | 91 | 75 | Met(h) | 46 |
| IR | 67 | 37 | Tie2(h) | 46 |
| IRR | 69 | 72 | EGFR(h) | 48 |
| JNK1-alpha-1 | 75 | 14 | IRAK4(h) | 52 |
| LCK | 54 | 14 | Tie2(R849W)(h) | 57 |
| MAPK1 | 91 | 78 | ALK(h) | 59 |
| MAPK2 | 79 | 90 | MSK2(h) | 60 |
| MAPK8 | 61 | 9 | CHK2(h) | 64 |
| MAPKAP-K1-alpha | 56 | 12 | AMPK(r) | 65 |
| MAPKAP-K1-beta | 68 | 19 | Fms(h) | 82 |
| MAPKAP-K2 | 100 | 88 | CaMKIV(h) | 83 |
| MARK3 | 73 | 74 | p70S6K(h) | 83 |
| MELK | 101 | 36 | FGFR4(h) | 87 |
| MKK1 | 71 | 13 | PDGFRα(h) | 87 |
| MNK-1 | 95 | 98 | Plk1(h) | 87 |
| MNK-2-alpha | 81 | 82 | ROCK-II(h) | 92 |
| MSK1 | 96 | 77 | ZIPK(h) | 95 |
| MST2 | 61 | 8 | CDK2/cyclinA(h) | 96 |
| MST4 | 89 | 59 | DDR2(h) | 96 |
| Nek2a | 82 | 66 | NEK2(h) | 96 |
| NEK6 | not tested | 93 | PKCα(h) | 100 |
| PAK4 | 81 | 38 | CHK1(h) | 101 |
| PAK5 | 92 | 72 | Plk3(h) | 104 |
| PAK6 | 90 | 81 | c-RAF(h) | 107 |
| PBK | 89 | 99 | ROCK-I(h) | 109 |
| PDK1 | 91 | 73 | JAK2(h) | 111 |
| Pim-1 | 65 | 61 | cKit(D816V)(h) | 112 |
| PIM-2 | 85 | 70 | PDGFRβ(h) | 112 |
| Pim-3 | 84 | 63 | PDK1(h) | 112 |
| PKA | 82 | 72 | CDK2/cyclinE(h) | 133 |
| PKB-alpha | 85 | 93 | | |
| PKB-beta | 85 | 101 | | |
| PKC-alpha | 57 | 56 | | |
| PKC-zeta | 104 | 99 | | |
| PKD2 | 78 | 73 | | |
| PLK1 | 63 | 4 | | |
| PLK1 | 92 | 12 | | |
| PRAK | 80 | 84 | | |
| PRK2 | 97 | 43 | | |
| ROCK-II | 79 | 75 | | |
| S6K1 | 74 | 94 | | |
| SAPK2-alpha | 76 | 89 | | |
| SAPK2-beta | 83 | 81 | | |
| SAPK3 | 87 | 72 | | |
| SAPK4 | 79 | 44 | | |
| SGK | 87 | 82 | | |
| smMLCK | 92 | 39 | | |
| SRC | 58 | 14 | | |
| SRPK1 | 83 | 65 | | |
| Syk | 84 | 52 | | |

TABLE 3-continued

Inhibition of Other Kinases by Specific Compounds of the Invention
At a Concentration of 1 μM (numbers shown are % inhibition)

| | | |
|---|---|---|
| TBK1 | 97 | 100 |
| VEGFR | 49 | 15 |
| YES1 | 49 | 9 | a

| | Example 10 @ 1 μM Compound G | Example 11 @ 1 μM Compound H | Example 20 @ 1 μM Compound I | Example 27 @ 1 μM Compound J | Example 24 @ 1 μM Compound K |
|---|---|---|---|---|---|
| Abl(h) | 101 | 92 | 79 | 3 | −4 |
| Abl(T315I)(h) | 47 | 95 | 34 | 1 | 0 |
| ALK(h) | 8 | 81 | 60 | 77 | 32 |
| AMPK(r) | 86 | 97 | 81 | 71 | 68 |
| Aurora-A(h) | 1 | 95 | 4 | 1 | 2 |
| Axl(h) | 10 | 105 | 40 | 63 | 48 |
| CaMKIV(h) | 66 | 119 | 103 | 111 | 100 |
| CDK2/cyclinE(h) | 23 | 92 | 69 | 60 | 100 |
| cKit(D816V)(h) | 96 | 102 | 112 | 95 | 97 |
| EGFR(h) | 53 | 113 | 67 | 34 | −2 |
| EphB2(h) | 5 | 115 | 27 | 67 | 17 |
| FAK(h) | 3 | 77 | 11 | 41 | 30 |
| FGFR4(h) | 128 | 100 | 102 | 96 | 50 |
| Flt3(D835Y)(h) | 7 | 110 | 8 | 12 | 3 |
| Flt3(h) | 65 | 102 | 16 | 66 | 21 |
| Hck(h) | 13 | 92 | 23 | 13 | 6 |
| IRAK4(h) | 3 | 90 | 12 | 12 | 19 |
| JAK2(h) | 95 | 121 | 46 | 62 | 60 |
| KDR(h) | 32 | 101 | 8 | 7 | 8 |
| Lyn(m) | 8 | 99 | 27 | 13 | 2 |
| Met(h) | 41 | 125 | 60 | 69 | 63 |
| MSK2(h) | 3 | 89 | 48 | 65 | 81 |
| NEK2(h) | 49 | 98 | 103 | 113 | 101 |
| PDGFRβ(h) | 149 | 93 | 110 | 115 | 95 |
| PDK1(h) | 96 | 98 | 80 | 86 | 108 |
| PKCα(h) | 90 | 94 | 107 | 102 | 103 |
| Pyk2(h) | 13 | 93 | 15 | 34 | 31 |
| Ret(h) | 7 | 56 | 11 | 4 | 1 |
| ROCK-I(h) | 96 | −2 | 96 | 104 | 93 |
| ROCK-II(h) | 90 | 102 | 99 | 110 | 120 |
| Rsk1(h) | 13 | 79 | 24 | 38 | 30 |
| Tie2(h) | 101 | 91 | 8 | 2 | 8 |
| Tie2(R849W)(h) | 41 | 103 | 14 | 17 | 28 |
| TrkA(h) | 0 | 8 | 1 | 1 | 5 |
| TrkB(h) | 1 | 32 | 5 | 5 | 1 |
| ZAP-70(h) | 118 | 124 | 122 | 125 | 112 |
| ZIPK(h) | 118 | 84 | 93 | 97 | 109 | b

| | Example 26 @ 1 μM Compound L | Example 21 @ 10 μM Compound M | Example 6 @ 1 μM Compound N | Example 5 @ 1 μM Compound O | Example 3 @ 1 μM Compound P |
|---|---|---|---|---|---|
| Abl(h) | −1 | 44 | 99 | 105 | 105 |
| Abl(T315I)(h) | 2 | 38 | 89 | 103 | 92 |
| ALK(h) | 88 | 57 | 101 | 97 | 86 |
| AMPK(r) | 79 | 57 | 51 | 58 | 92 |
| Aurora-A(h) | 0 | 2 | 3 | 7 | 11 |
| Axl(h) | 55 | 66 | 78 | 96 | 107 |
| CaMKIV(h) | 11 | 76 | 99 | 97 | 140 |
| CDK2/cyclinE(h) | 15 | 89 | 107 | 109 | 114 |
| cKit(D816V)(h) | 112 | 104 | 96 | 103 | 77 |
| EGFR(h) | 57 | 49 | 67 | 63 | 120 |
| EphB2(h) | 112 | 8 | 80 | 94 | 94 |
| FAK(h) | 35 | 7 | 81 | 91 | 86 |
| FGFR4(h) | 53 | 81 | 96 | 94 | 122 |
| Flt3(D835Y)(h) | 57 | 2 | 33 | 63 | 77 |
| Flt3(h) | 93 | 2 | 116 | 117 | 98 |
| Hck(h) | 10 | 39 | 110 | 123 | 101 |
| IRAK4(h) | 43 | 31 | 52 | 81 | 82 |
| JAK2(h) | 16 | 48 | 108 | 94 | 89 |
| KDR(h) | 8 | 10 | 62 | 70 | 95 |
| Lyn(m) | 111 | 36 | 93 | 108 | 104 |
| Met(h) | 9 | 30 | 122 | 114 | 115 |
| MSK2(h) | 2 | 75 | 60 | 56 | 136 |
| NEK2(h) | 79 | 92 | 107 | 110 | 95 |

TABLE 3-continued

Inhibition of Other Kinases by Specific Compounds of the Invention
At a Concentration of 1 μM (numbers shown are % inhibition)

| | | | | | |
|---|---|---|---|---|---|
| PDGFRβ(h) | 58 | 104 | 107 | 117 | 110 |
| PDK1(h) | 88 | 78 | 90 | 92 | 102 |
| PKCα(h) | 81 | 91 | 90 | 84 | 70 |
| Pyk2(h) | 99 | 11 | 110 | 122 | 94 |
| Ret(h) | 50 | 35 | 12 | 52 | 78 |
| ROCK-I(h) | 2 | 98 | 99 | 106 | 101 |
| ROCK-II(h) | 94 | 94 | 97 | 105 | 80 |
| Rsk1(h) | 41 | 31 | 53 | 71 | 78 |
| Tie2(h) | 44 | 33 | 119 | 104 | 99 |
| Tie2(R849W)(h) | 26 | 35 | 91 | 92 | 93 |
| TrkA(h) | 1 | 15 | 50 | 60 | 58 |
| TrkB(h) | 3 | 18 | 90 | 85 | 83 |
| ZAP-70(h) | 112 | 94 | 125 | 122 | 109 |
| ZIPK(h) | 106 | 86 | 112 | 110 | 118 |

All publications and patent applications cited in this specification hereby are incorporated by reference. Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit and scope of the invention.

We claim:

1. A compound of the Formula I:

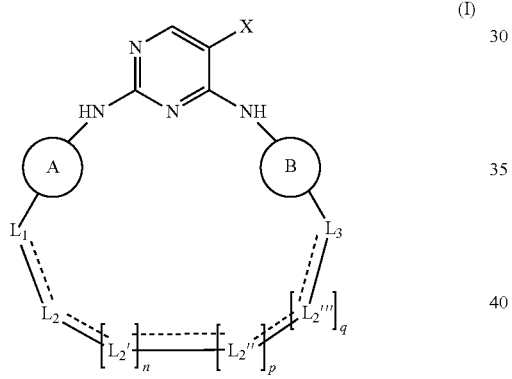

(I)

wherein:
X is F;

is aryl;

is cyclopentane, optionally substituted by carboxamide and dihydroxyethyl;

- - - represents the presence or absence of a double bond;
$L_1$ is O;
$L_2$ is $CH_2$;
$L_{2'}$, and $L_3$ each independently, is CHOH;
n is 1;
p and q, each independently, is 0 or 1; or a pharmaceutically acceptable salt, tautomer, enantiomer or racemic mix thereof.

2. The compound of claim 1 wherein X is F and

is phenyl, which is unsubstituted or substituted by CN, OH, F or 4-methyl-piperazine.

3. A pharmaceutical composition comprising a compound of Formula I according to claim 1, and a physiologically acceptable carrier, diluent, or excipient.

4. A kit comprising separate packets, the first having a therapeutically effective amount of a pharmaceutical composition according to claim 3, and the second having a therapeutically effective amount of a pharmaceutical composition comprising a further pharmaceutically active ingredient.

5. The compound of claim 1 selected from the group consisting of:
(16Z)-4-fluoro-14,19-dioxa-2,6,8,26-tetraazatetracyclo[18.2.2.1~3,7~0.1~9,13~]hexacosa-3(26),4,6,9(25),10,12,16-heptaene; and
(16E)-4-fluoro-14,19-dioxa-2,6,8,26-tetraazatetracyclo[18.2.2.1~3,7~0.1~9,13~]hexacosa-3(26),4,6,9(25),10,12,16-heptaene:
or a pharmaceutically acceptable salt, tautomer, enantiomer or racemic mix thereof.

* * * * *